(12) United States Patent
Hashimoto et al.

(10) Patent No.: US 11,667,924 B2
(45) Date of Patent: *Jun. 6, 2023

(54) INCREASING LEVELS OF NICOTINIC ALKALOIDS IN PLANTS

(71) Applicant: 22nd Century Limited, LLC, Williamsville, NY (US)

(72) Inventors: Takashi Hashimoto, Nara-ken (JP); Masataka Kajikawa, Nara (JP)

(73) Assignee: 22ND CENTURY LIMITED, LLC, Buffalo, NY (US)

( * ) Notice: Subject to any disclaimer, the term of this patent is extended or adjusted under 35 U.S.C. 154(b) by 116 days.

This patent is subject to a terminal disclaimer.

(21) Appl. No.: 17/141,030

(22) Filed: Jan. 4, 2021

(65) Prior Publication Data

US 2021/0317465 A1   Oct. 14, 2021

Related U.S. Application Data

(60) Continuation of application No. 16/258,393, filed on Jan. 25, 2019, now Pat. No. 10,907,170, which is a division of application No. 15/411,721, filed on Jan. 20, 2017, now Pat. No. 10,190,129, which is a division of application No. 11/520,036, filed on Sep. 13, 2006, now Pat. No. 9,551,003.

(51) Int. Cl.
| | |
|---|---|
| C12N 15/82 | (2006.01) |
| A24B 13/00 | (2006.01) |
| A24D 1/00 | (2020.01) |
| A61K 31/465 | (2006.01) |

(52) U.S. Cl.
CPC .......... *C12N 15/8243* (2013.01); *A24B 13/00* (2013.01); *A24D 1/00* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 4,407,956 A | 10/1983 | Howell | |
| 5,459,252 A | 10/1995 | Conkling et al. | |
| 5,466,785 A | 11/1995 | De Framond | |
| 5,633,363 A | 5/1997 | Colbert et al. | |
| 5,803,081 A | 9/1998 | O'Donnell, Jr. et al. | |
| 5,837,848 A | 11/1998 | Ey et al. | |
| 5,837,876 A | 11/1998 | Conkling et al. | |
| 5,852,041 A | 12/1998 | Cosford et al. | |
| 6,018,099 A | 1/2000 | De Framond | |
| 6,054,637 A * | 4/2000 | Boller ............ C12Y 302/01039 800/278 |
| 6,135,121 A | 10/2000 | Williams | |
| 6,423,520 B1 | 7/2002 | Conkling et al. | |
| 6,586,661 B1 | 7/2003 | Conkling et al. | |
| 6,805,134 B2 | 10/2004 | Peele | |
| 6,895,974 B2 | 5/2005 | Peele | |
| 6,907,887 B2 | 6/2005 | Conkling | |
| 6,959,712 B2 | 11/2005 | Bereman et al. | |
| 8,097,710 B2 | 1/2012 | Baulcombe et al. | |
| 8,791,329 B2 | 7/2014 | Hashimoto | |
| 8,987,555 B2 | 3/2015 | Hashimoto | |
| 9,029,656 B2 | 5/2015 | Hashimoto | |
| 9,551,003 B2 * | 1/2017 | Hashimoto .......... A61K 31/465 |
| 9,719,103 B2 * | 8/2017 | Hashimoto ........... A24B 13/02 |
| 9,834,780 B2 | 12/2017 | Hashimoto et al. | |
| 9,856,487 B2 | 1/2018 | Hashimoto et al. | |
| 10,190,129 B2 * | 1/2019 | Hashimoto ........... A24B 13/00 |
| 10,368,573 B2 | 8/2019 | Hashimoto | |
| 10,829,774 B2 * | 11/2020 | Hashimoto .............. A24D 1/00 |
| 10,907,170 B2 * | 2/2021 | Hashimoto ........ C12N 15/8243 |
| 2003/0106105 A1 | 6/2003 | Hoffmann et al. | |
| 2003/0221213 A1 | 11/2003 | Rommens et al. | |
| 2004/0107455 A1 | 6/2004 | Rommens et al. | |
| 2004/0143874 A1 | 7/2004 | Moller et al. | |
| 2005/0010974 A1 | 1/2005 | Milligan et al. | |
| 2005/0034365 A1 | 1/2005 | Li et al. | |
| 2005/0072047 A1 | 4/2005 | Conkling et al. | |
| 2005/0097633 A1 | 5/2005 | Diehn et al. | |
| 2005/0223442 A1 | 10/2005 | Xu | |
| 2006/0041949 A1 | 2/2006 | Xu et al. | |

FOREIGN PATENT DOCUMENTS

| | | |
|---|---|---|
| KR | 10200419301 | 3/2004 |
| WO | WO 98/56923 | 10/1998 |
| WO | WO 00/52168 | 9/2000 |
| WO | WO 01/59086 A2 | 8/2001 |
| WO | WO 02/38588 A2 | 5/2002 |

(Continued)

OTHER PUBLICATIONS

Hibi et al (1994, Plant Cell 6:723-735).*
Office Action issued in related U.S. Appl. No. 14/444,511, dated Sep. 28, 2016.
Office Action issued in related U.S. Appl. No. 14/444,511, dated Jun. 15, 2016.
Office Action issued in related Canadian Patent Application No. 2872521, dated Nov. 13, 2015.
Office Action issued in related U.S. Appl. No. 13/082,593, dated Feb. 25, 2014.
Office Action issued in related U.S. Appl. No. 11/579,661, dated Feb. 21, 2014.

(Continued)

*Primary Examiner* — Anne Kubelik
(74) *Attorney, Agent, or Firm* — Foley & Lardner LLP

(57) ABSTRACT

Four genes, A622, NBB1, PMT, and QPT, can be influenced for increasing nicotinic alkaloid levels in *Nicotiana* plants, as well as for synthesizing nicotinic alkaloids in non-nicotine producing plants and cells. In particular, overexpressing one or more of A622, NBB1, PMT, and QPT may be used to increase nicotine and nicotinic alkaloid levels in tobacco plants. Non-nicotine producing cells can be engineered to produce nicotine and related compounds by overexpressing A622 and NBB1.

10 Claims, 21 Drawing Sheets

Specification includes a Sequence Listing.

(56) References Cited

FOREIGN PATENT DOCUMENTS

| WO | WO 02/066625 | | 8/2002 |
|---|---|---|---|
| WO | WO 02/100199 | A2 | 12/2002 |
| WO | WO 03/013226 | A2 | 2/2003 |
| WO | WO 2004/076625 | A2 | 10/2004 |
| WO | WO 2005/018307 | A1 | 3/2005 |
| WO | WO 2006/091194 | A1 | 8/2006 |
| WO | WO 2006/109197 | A2 | 10/2006 |

OTHER PUBLICATIONS

Goossens, A. et al. "A functional genomics approach toawrd the understanding of secondary metabolism in plant cells", PNAS, Jul. 8, 2003, vol. 100, No. 14, pp. 8595-8600.
KR Application No. 10-2007-7022315, Notice of Non-Final Rejection dated Jul. 16, 2013.
Office Action in AU Appln No. 2012203977 dated Dec. 18, 2013.
Office Action in CA Appln No. 2,599,302 dated Jan. 9, 2014.
Office Action in CN Appln No. 201210252031.7 dated Oct. 24, 2013.
Office Action in U.S. Appl. No. 11/520,036 dated May 21, 2010.
Office Action in U.S. Appl. No. 11/579,661 dated Oct. 7, 2013.
Rymerson, R.T. et al. "Immunogenicity of the capsid protein VP2 from porcine parvovirus expressed in low alkaloid transgenic tobacco", Molecular Breeding, May 4, 2003; 11(4):267-276.
Database EMBL Nicotiana tabacum mRNA for A622, Jul. 6, 1994, Hibi et al., XP002429627 retrieved from EBI Database accession No. D28505 Abstract.
Database UniProt Isoflavone reductase-like protein A622, Jul. 5, 2004, Shoji et al., XP002429628 retrieved from EBI Database accession No. Q76LW3, Abstract.
Chinese Office Action 200680010544X dated Sep. 16, 2010.
Naruhiro Hibi et al., "Gene Expression in Tobacco Low-Nicotine Mutants", The Plant Cell vol. 6, 723-735, May 1994.
Jed E. Rose, "The Role of Upper Airway Stimulation in Smoking", Nicotine Replacement: A Critical Evaluation, pp. 95-106, 1988.
C.W. Bacon et al., "Chemical Changes in Tobacco during Flue-Curing", Industrial and Engineering Chemistry, vol. 44, No. 2, pp. 292-296, Feb. 1952.
Dietrich Hoffmann et al., "Origin in Tobacco Smoke of N'-Nitrosonornicotine, a Tobacco-Specific Carcinogen: Brief Communication", J. Natl. Cancer Inst. vol. 58, No. 6, Jun. 1977, pp. 1841-1844.
Mirjana V. Djordjevic et al., "Tobacco-Specific Nitrosamine Accumulation and Distribution in Flue-Cured Tobacco Alkaloid Isolines", J. Agric. Food Chem., 1989, 37, 752-756.
Lei Zhang et al., "Engineering tropane biosynthetic pathway in Hyosyamus niger hairy root cultures", PNAS, vol. 101, No. 17, pp. 6786-6791.
Joseph Sambrook et al., "Chapter 7: Extraction, Purification, and Analysis of mRNA from Eukaryotic Cells", Molecular Cloning A Laboratory Manual vol. 1, Third Edition, 2001.
Heinz Dittrich et al., "Molecular cloning, expression, and induction of berberine bridge enzyme, an enzyme essential to the formation of benzophenanthridine alkaloids in the response of plants to pathogenic attack", Proc. Natl. Acad. Sci. USA, vol. 88, pp. 9969-9973, Nov. 1991.
Clay J. Carter et al., "Tobacco Nectarin V Is a Flavin-Containing Berberine Bridge Enzyme-Like Protein with Glucose Oxidase Activity", Plant Physiology, Jan. 2004, vol. 134, pp. 460-469.
Takeshi Kanegae et al., "Species-Dependent Expression of the Hyoscyamine 6β-Hydroxylase Gene in the Pericycle", Plant Physiol. (1994) 105: 483-490.
Naruhiro Hibi et al., "Gene Expression in Tobacco Low-Nicotine Mutants", The Plant Cell, vol. 6, pp. 723-735, May 1994.
Maria A. Restrepo et al., "Nuclear Transport of Plant Potyviral Proteins", The Plant Cell, vol. 2, 987-998, Oct. 1990.

Kazuhito Akama et al., "Efficient transformation of Arabidopsis thaliana: comparison of the efficiencies with various organs, plant ecotypes and Agrobacterium strains", Plant Cell Reports (1992) 12: 7-11.
Steven J. Clough et al., "Floral dip: a simplified method for Agrobacterium-mediated transformation of Arabidopsis thaliana", The Plant Journal (1998) 16(6), pp. 735-743.
David B. Archer et al., "Strategies for improving heterologous protein production from filamentous fungi", Antonie van Leeuwenhoek 65: 245-250, 1994.
Manfred Gossen et al., "Tight control of gene expression in mammalian cells by tetracycline-responsive promoters", Proc. Natl. Acad. Sci. USA, vol. 89, pp. 5547-5551, 1992.
Stephen P. Mayfield et al., "Expression of human antibodies in eukaryotic micro-algae", Vaccine, 23, (2005), 1828-1832.
Nicole Bechtold et al., "In planta Agrobacterium mediated gene transfer by infiltration of adult Arabidopsis thaliana plants", C.R. Acad. Sci. Paris, Sciences de la vie/Life sciences, 1993:316, 1194-1199.
Jerzy Paszkowski et al., "Direct gene transfer to plants", The EMBO Journal, vol. 3, No. 12, pp. 2717-2722, 1984.
Laszlo Sagi et al., "Transient gene expression in electroporated banana (Musa spp., cv. 'bluggoe', ABB group) protoplasts isolated from regenerable embryogenetic cell suspensions", Plant Cell Reports, (1994) 13: 262-266.
R. Nagel et al., "Electroporation of binary Ti plasmid vector into Agrobacterium tumefaciens and Agrobacterium rhizogenes", FEMS Microbiology Letters, 67 (1990), 325-328.
Wim Broothaerts et al., "Gene transfer to plants by diverse species of bacteria", Nature, vol. 433, Feb. 10, 2005, pp. 629-633.
Horst Lörz et al., "Gene transfer to cereal cells mediated by protoplast transformation", Mol. Gen Genet (1985), 199: 178-182.
A. de la Peña et al., "Transgenic rye plants obtained by injecting DNA into young floral tillers", Nature, vol. 325, Jan. 15, 1987, pp. 274-276.
Carol. A. Rhodes et al., "Genetically Transformed Maize Plants from Protoplasts", Science, vol. 240, Apr. 8, 1988, pp. 204-207.
Ko Shimamoto et al., "Fertile transgenic rice plants regenerated from transformed protoplasts", Nature, vol. 338, Mar. 16, 1989, pp. 274-276.
Naruhiro Hibi et al., "Putrescine N-Methyltransferase in Cultured Roots of Hyoscyamus albus", Plant Physiol. (1992), 100, 826-835.
Yoshiko Miyagawa et al., "Evaluation of the Defense System in Chloroplasts to Photooxidative Stress Caused by Paraquat Using Transgenic Tobacco Plants Expressing Catalase from Escherichia coli ", Plant Cell Physiol. 41(3): 311-320 (2000).
R.C. Leegood, "16: Carbon Metabolism", Photosynthesis and Production in a Changing Environment A Field and Laboratory Manual, Edited by D.O. Hall et al.,(1993), pp. 247-267.
Claudia Voelckel et al., "Anti-sense expression of putrescine N-methyltransferase confirms defensive role of nicotine in Nocotiana sylvestris against Manduca sexta", Chemoecology 11: 121-126 (2001).
Dietrich Hoffmann et al., "The Changing Cigarette: Chemical Studies and Bioassays", Smoking and Tobacco Control Monograph No. 13, Chapter 5, Nov. 19, 2001, pp. 159-192.
H.C. Pillsbury et al., "TOBACCO Tar and Nicotine in Cigarette Smoke", Journal of the AOAC, vol. 52, No. 3, 1969, pp. 458-462.
Gio B. Gori et al., "Analytical Cigarette Yields as Predictors of Smoke Bioavailability", Regulatory Toxicology and Pharmacology 5, 314-326 (1985).
Deborah G. Reed et al., "The A and B loci of Nicotiana tabacum have non-equivalent effects on the mRNA levels of four alkaloid biosynthetic genes", Plant Science 167 (2004) 1123-1130.
Akira Katoh et al., "Analysis of expression sequence tags from Nicotiana sylvestris", Proc. Japan Acad. 79, No. 6, Ser. B (2003), pp. 151-154.
Fumihiko Sato et al., "Metabolic engineering of plant alkaloid biosynthesis", PNAS, Jan. 2, 2001, vol. 98, No. 1, pp. 367-372.
Fumiyo Saitoh et al., "The Alkaloid Contents of Sixty Nicotiana Species", Phytochemistry, vol. 24, No. 3, pp. 477-480, 1985.

(56) References Cited

OTHER PUBLICATIONS

Takashi Hashimoto et al., "Intraspecific variability of the tandem repeats in *Nicotiana putrescine* N-methyltransferases", Plant Molecular Biology, 37: 25-37, 1998.
Dean E. Riechers et al., "Structure and expression of the gene family encoding putrescine N-methyltransferase in *Nicotiana tabacum*: new clues to the evolutionary origin of cultivated tobacco", Plant Molcular Biology 41: 387-401, 1999.
Elisabeth Moyano et al., "Alkaloid production in *Duboisia hybrid* hairy root cultures overexpressing the pmt gene", Phytochemistry 59 (2002) 697-702.
Grit Rothe et al., "Alkaloids in plants and root cultures of *Atropa belladonna* overexpressing putrescine N-methyltransferase", Journal of Experimental Botany, vol. 54, No. 390, pp. 2065-2070, Sep. 2003.
Elisabet Moyano et al., "Effect of pmt gene overexpression on tropane alkaloid production in transformed root cultures of *Datura metal* and *Hyosyamus muticus*", Jouranl fo Experimental Botany, vol. 54, No. 381, pp. 203-211, Jan. 2003.
TOBACCO Production Chemistry & Technology, Edited by D. Layten Davis et al., 1999, pp. 45-46.
Isabel Murillo et al., "Engineering photoassimilate partitioning in tobacco plants improves growth and productivity and provides pathogen resistance", The Plant Journal (2003) 36, 330-341.
Masahiro Tamoi et al., "Contribution of Fructose-1,6-bisphosphatase and Sedoheptulose-1,7-bisphosphatase to the Photosynthetic Rate and Carbon Flow in the Calvin Cycle in Transgenic Plants", Plant Cell Physiol. 47(3): 380-390 (2006).
Yoshiko Miyagawa et al., "Overexpression of a cyanobacterial fructose-1,6-/sedoheptulose-1, 7-bisphosphatase in tobacco enhances photosynthesis and growth", Nature Biotechnolgoy, vol. 19, Oct. 2001, pp. 965-969.
Mark J. Zoller et al., "Oligonucleotide-directed mutagenesis using M13-derived vectors: an efficient and general procedure for the production of point mutations in any fragment of DNA", Nucleic Acids Research, vol. 10, No. 20, 1982, pp. 6487-6500.
Stephen F. Altschul et al., "Gapped BLAST and PSI-BLAST: a new generation of protein database search programs", Nucleic Acids Research, 1997, vol. 23, No. 17, pp. 3389-3402.
Francis C. Hsu et al., "Phloem Mobility of Xenobiotics VI. A Phloem-Mobile Pro-nematicide Based on Oxamyl Exhibiting Root-Specific Activation in Transgenic Tobacco", Pestic. Sci. 1995, 44, pp. 9-19.
Ishwan Hwang et al., "An *Arabidopsis thaliana* root-specific kinase homolog is induced by dehydration, ABA, and NaCI", The Plant Journal (1995), 8(1), 37-43.
Tsubasa Shoji et al., "Jasmonate Induction of Putrescine N-Methyltransferase Genes in the Root of *Nicotiana sylvestris*", Plant Cell Physiol. 41(7): 831-839 (2000).
Charles J. Thompson et al., "Characterization of the herbicide-resistance gene bar from *Streptomyces hygroscopicus*", The EMBO Journal, vol. 6, No. 9, pp. 2519-2523, 1987.
Peter R. Beetham et al., A tool for functional plant genomics: Chimeric RNA/DNA oligonucleotides cause in vivo gene-specific mutations, Proc. Natl. Acad. Sci. USA, vol. 96, pp. 8774-8778, Jul. 1999.
Tong Zhu et al., "Targeted manipulation of maize genes in vivo using chimeric RNA/DNA oligonucleotides", Proc. Natl. Acad. Sci. USA, vol. 96, pp. 8768-8773, Jul. 1999.
Chantal David et al., "Conservation of T-DNA in Plants Regenerated from Hairy Root Cultures", Bio/Technology, Jan. 1984, pp. 73-76.
K-M. Oksman-Caldentey et al., "Chapter 13: Regulation of Tropane Alkaloid Metabolism in Plants and Plant Cell Cultures", Metabolic Engineering of Plant Secondary Metabolism, Kluwar Academic Publishers, 2000, pp. 253-281.
Steven J. Sinclair et al., "Molecular characterization of puinolinate phosphoribosyltransferase (QPRTase) in Nicotiana", Plant Molecular Biology, 44: 603-617, 2000.

Naruhiro Hibi et al., "Gene Expression in Tobacco Low-Nicotine Mutants", The Plant Cell, vol. 6, May 1994, pp. 723-735.
Yupynn Chintapakorn et al., "Antisense-mediated down-regulation of putrescine N-methyltransferase activity in transgenic *Nicotiana tabacum* L. can lead to elevated levels of anatabine at the expense of nicotine", Plant Molecular Biology 53: 87-105, 2003.
Anke Steppuhn et al., "Nicotine's Defensive Function in Nature", PLoS Biology, Aug. 2004, vol. 2, Issue 8, 1074-1080.
A.K. Armitage et al., "Evaluation of a low to middle tar/medium nicotine cigarette designed to maintain nicotine delivery to the smoker", Psychopharmacology (1988) 96: 47-453.
Karl-Olov Fagenström, "Effects of a Nicotine-Enriched Cigarette on Nicotine Titration, Daily Cigarette Consuption, and Levels of Carbon Monoxide, Cotinine, and Nicotine", Psychopharmacology (1982) 77: 164-167.
G. Woodman et al., "The separate effects of tar and nicotine on the cigarette smoking manoeuvre", Eur J Respir Dis, (1987) 70, pp. 316-321.
Kathleen Stratton et al., "Clearing the Smoke Assessing the Science Base for Tobacco Harm Reduction", Committee to Assess the Science Base for Tobacco Harm Reduction, Board on Health Promotion and Disease Prevention, Institute of Medicine, 2001.
Emily Singer, "The Upside to Nicotine?", Technology Review: MIT's Magazine of Innovation, vol. 109, No. 3, Jul.-Aug. 2006.
S.L. Beaucage et al., "Deoxynucleoside Phosphoramidites—A New Class of Key Intermediates for Deoxypolynucleotide Synthesis", Tetrahedron Letters, vol. 22, No. 20, pp. 1859-1862, 1981.
M.D. Matteucci et al., "Synthesis of Deoxyoligonucleotides on a Polymer Support", J. Am. Chem. Soc., 1981, 103, 3185-3191.
Stephen S. Hecht et al., "Tobacco-Specific Nitrosamines: Occurrence, Formation, Carcinogenicity, and Metabolism", Accounts of Chemical Research, 1979 American Chemical Society, vol. 12, pp. 92-98.
T.C. Tso, "Production, Physiology, and Biochemistry of Tobacco Plant", 1990, Ideals Inc.
L.P. Bush et al., "Biosynthesis and metabolism of nicotine and related alkaloids", Nicotine and Related Alkaloids: Absorption Distribution Metabolism and Excretion, 1993, pp. 1-30.
TOBACCO Production, Chemistry and Technology, 1999, Coresta Blackwell Science Ltd.
François-Xavier Felpin et al., "Efficient Enantiomeric Synthesis of Pyrrolidine and Piperidine Alkaloids from Tobacco", J. Org. Chem. 2001, 66, 6305-6312.
Dietrich Hoffmann et al., "Tobacco-Specific N-Nitrosamines and Areca-Derived N-Nitrosamines: Chemistry, Biochemistry, Carcinogenicity, and Relevance to Humans", Journal of Toxicology and Environmental Health, 41: 1-52, 1994.
Tsubasa Shoji et al., "Ethylene Suppresses Jasmonate-Induced Gene Expression in Nicotine Bio-synthesis", Plant Cell Physiol. 41(9): 1072-1076, (2000).
Tsubasa Shoji et al., "Expression patterns of two tobacco isoflavone reductase-like genes and their possible roles in secondary metabolism in tobacco", Plant Molecular Biology 50: 427-440, 2002.
Karen A. Cane et al., "Molecular analysis of alkaloid metabolism in AABB v. aabb genotype *Nicotiana tabacum* in response to wounding of aerial tissues and methyl jasmonate treatment of cultured roots", Functional Plant Biology, 2005, 32, 305-320.
Steven J. Sinclair et al., "Analysis of wound-induced gene expression in Nicotiana species with contrasting alkaloid profiles", Functional Plant Biology, 2004, 31, 721-729.
Paul D. Legg et al., "Inheritance of Per Cent Total Alkaloids in *Nicotiana tabacum* L. II. Genetic Effects Two Loci in Burley 21 X LA Burley 21 Populations", Can. J. Genet. Cytol. 13: 287-291, 1971.
Naruhiro Hibi et al., "Gene Expression in Tobacco Low-Nicotine Mutants", The Plant Cell, vol. 6, pp. 723-735, May 1994.
Office Action issued in related U.S. Appl. No. 14/444,511, dated Apr. 28, 2017.
Notice of Allowance issued in related U.S. Appl. No. 14/685,361, dated Aug. 7, 2017.
Notice of Allowance issued in related U.S. Appl. No. 14/444,511, dated Aug. 23, 2017.

(56) References Cited

OTHER PUBLICATIONS

Supplemental Notice of Allowance issued in related U.S. Appl. No. 14/444,511, dated Sep. 14, 2017.
Supplemental Notice of Allowance issued in related U.S. Appl. No. 14/685,361, dated Oct. 4, 2017.
Non-Final Office Action issued in related U.S. Appl. No. 15/828,868, dated Jan. 30, 2018.
Non-Final Office Action issued in related U.S. Appl. No. 15/828,875, dated Jan. 30, 2018.
Notice of Allowance issued in related U.S. Appl. No. 15/828,868, dated May 29, 2018.
Notice of Allowance issued in related U.S. Appl. No. 15/828,875, dated May 18, 2018.
Non-Final Office Action issued in related U.S. Appl. No. 15/422,455, dated Feb. 22, 2018.
Non-Final Office Action issued in related U.S. Appl. No. 15/422,460, dated Feb. 22, 2018.
Corrected Notice of Allowance issued in related U.S. Appl. No. 15/828,868, dated Jun. 27, 2018.
Corrected Notice of Allowance issued in related U.S. Appl. No. 15/828,875, dated Jun. 27, 2018.
Notice of Allowance issued in related U.S. Appl. No. 15/422,460, dated Jun. 20, 2018.
Corrected Notice of Allowance issued in related U.S. Appl. No. 15/828,868, dated Jul. 30, 2018.
Corrected Notice of Allowance issued in related U.S. Appl. No. 15/828,875, dated Jul. 30, 2018.
Notice of Allowance issued in co-pending U.S. Appl. No. 15/422,460, dated Aug. 3, 2018.
Office Action issued in co-pending U.S. Appl. No. 15/858,599, dated Oct. 4, 2018.
Notice of Allowance issued in related U.S. Appl. No. 15/422,455, dated Sep. 26, 2018.
Dym, et al., "Sequence-structure analysis of FAD-containing proteins," *Prot. Sci.*, vol. 10, pp. 1712-1728 (2001).
Weiner, et al., NADP+ Binding to Dehydrogenases, IN: Handbook of Proteins, vol. 1, pp. 626-632 (2007).
Guo et al., "Protein Tolerance to Random Amino Acid Change," *Proc. Natl. Acad. Sci.*, vol. 101, pp. 9205-9210 (2004).
Kajikawa et al., "Vacuole-Localized Berberine Bridge Enzyme-Like Proteins Are Required for a Late Step of Nicotine Biosynthesis in Tobacco," *Plant Physiol.*, vol. 155, pp. 2010-2022 (2011).
Office Action issued in co-pending Chinese Patent Application No. 2016107552030, dated Jan. 2, 2019.
Office Action issued in co-pending U.S. Appl. No. 16/258,445, dated Jan. 16, 2020.
Extended Search Report issued in European Patent Application No. 19177939, dated Oct. 15, 2019.
Junker, et al., "Evolution of the Key Alkaloid Enzyme Putrescine N-methyltransferase from Spermidine Synthase," *Frontiers in Plant Science*, vol. 4, 11 pages (Jan. 2013).
Office Action issued in co-pending U.S. Appl. No. 16/258,445, dated Apr. 24, 2020.
Notice of Allowance issued in co-pending U.S. Appl. No. 16/258,445, dated Jul. 7, 2020.
Biastoff et al., "Putrescine N-methyltransferase—The start for alkaloids," Phytochemistry, vol. 70, 2009, pp. 1708-1718.
GenBank T07969, 2001, https://www.ncbi.nlm.nih.gov/protein/7484602?report=genpept.
Lewis et al., "Transgenic and Mutation-Based Suppression of a Berberine Bridge Enzyme-Like (BBL) Gene Family Reduces Alkaloid Content in Field-Grown Tobacco," PLOS ONE, DOI:10.1371/journal.pone.0117273, 2015 (17 pages).

* cited by examiner

Figure 2

Alignment of NBB1 with Eschscholzia californica berberine bridge enzyme (EcBBE)

Phylogenetic tree constructed using the sequences of NBB1 polypeptide and plant BBE-like proteins

Figure 4A  T-DNA region of pTobRD2-DEST

Figure 4B  T-DNA region of pTobRD2-NBB1ox

Figure 4C  T-DNA region of pTobRD2-A622ox

Figure 4D  T-DNA region of pTobRD2-A622ox-NBB1ox

Figure 4E  T-DNA region of pBI101H-E2113-DEST

Figure 4F  T-DNA region of pEI235SΩ-NBB1

Figure 5A Immunoblot analysis of NBB1 in tobacco hairy roots

Figure 5B Immunoblot analysis of A622 in tobacco hairy roots

Nicotine alkaloid contents in hairy roots of TobRD2-NBB1 (TN), TobRD2-A622 (TA), TobRD2-NBB1-A622 (TNA)

Transgenic *A. belladonna* Expressing NBB1 and A622

**Nicotine synthesis in transgenic *A. belladonna* hairy roots expressing NBB1 and A622**

MS profile of nicotine synthesized in *A. belladonna* hairy roots expressing A622 and NBB1

MS profile of peak 5 in E2 line

MS profile of nicotine standard

Figure 11A  T-DNA region of pA622pro-DEST

Figure 11B  T-DNA region of pA622pro-PMTox

Figure 11C  T-DNA region of pTobRD2-PMTox

Figure 11D  T-DNA region of pA622pro-QPTox

Figure 11E  T-DNA region of pTobRD2-QPTox

Figure 11F  T-DNA region of pA622pro-PMTox-QPTox

Figure 11G  T-DNA region of pTobRD2-PMTox-QPTox

Nicotine content in leaf of tobacco plants transformed with A622pro-PMTox (AP-1 to AP-

Figure 13

Nicotine content in leaf of tobacco plants transformed with TobRD2-PMTox (TP-1 to TP-14). TG-1 to TG-3 are control plants transformed with TobRD2-GUS.

Nicotine content in leaf of tobacco plants transformed with A622pro-QPTox (AQ-1 to AQ-15). AG-1 to AG-4 are control plants transformed with A622-GUS.

Nicotine content in leaf of tobacco plants transformed with TobRD2-QPTox (TQ-1 to TQ-14). TG-1 to TG-3 are control plants transformed with TobRD2-GUS.

Figure 16

Nicotine content in leaf of tobacco plants transformed with A622pro-PMTox-QPTox (APQ-1 to APQ-27). AG-1 to AG-3 are control plants transformed with A622-GUS.

Figure 17

Nicotine content in leaf of tobacco plants transformed with pTobRD2-PMTox-QPTox (TP

Figure 18A T-DNA region of pGWB2

Figure 18B T-DNA region of p35S-NBB1

Figure 18C T-DNA region of p35S-PMT

Immunoblot analysis of *Arabidopsis thaliana* lines transformed with 35S-A622-35S-NBB1-35S-PMT cassettes

Figure 21A Confirmation of the presence of *A622* and *NBB1 in* recombinant bacmids

Figure 21B Detection of A622 and NBB1 in infected insect cell Sf9 cells and Ni-NTA column eluates

SEQUENCE LISTING

<160> NUMBER OF SEQ ID NOS: 34

<210> SEQ ID NO 1
<211> LENGTH: 1749
<212> TYPE: DNA
<213> ORGANISM: Nicotiana tabacum

<400> SEQUENCE: 1

```
acgcgggag  aaatacatac  aacatgtttc  cgctcataat  tctgatcagc  ttttcacttg     60
cttccttgtc  tgaaactgct  actggagctg  ttacaaatct  ttcagcctgc  ttaatcaacc    120
acaatgtcca  taacttctct  atttaccccca  caagtagaaa  ttacttaaac  ttgctccact   180
```

-continued

```
tctcccttca aaatcttcgc tttgctgcac ctttcatgcc gaaaccaacc ttcattatcc      240
taccaagcag taaggaggag ctcgtgagca ccatttttg  ttgcagaaaa gcatcttatg      300
aaatcagagt aaggtgcggc ggacacagtt acgaaggaac ttcttacgtt tcctttgacg      360
cttctccatt cgtgatcgtt gacttgatga aattagacga cgtttcagta gatttggatt      420
ctgaaacagc ttgggctcag gcggcgcaa  caattggcca aatttattat gccattgcca      480
aggtaagtga cgttcatgca ttttcagcag gttcggacc  aacagtagga tctggaggtc      540
atatttcagg tggtggattt ggactttat  ctagaaaatt cggacttgct gctgataatg      600
tcgttgatgc tcttcttatt gatgctgatg acggttatt  agaccgaaaa gccatgggcg      660
aagacgtgtt tgggcaatc  agaggtggcg gcggtggaaa ttggggcatt gtttatgcct      720
ggaaaattcg attactcaaa gtgcctaaaa tcgtaacaac ttgtatgatc tataggcctg      780
gatccaaaca atacgtggct caaatacttg agaaatggca atagttact  ccaaatttgg      840 tcgatgattt tactctagga gtactgctga gacctgcaga tctacccgcg gatatgaaat      900
atggtaatac tactcctatt gaaatatttc cccaattcaa tgcactttat ttgggtccaa      960
aaactgaagt tctttccata tcgaatgaga catttccgga gctaggcgtt aagaatgatg     1020
agtgcaagga aatgacttgg gtagagtcag cacttttctt ctccgaatta gctgacgtta     1080 acggaactc  gactggtgat atctcccgtc tgaaagaacg ttacatggac ggaaaaggtt     1140
ttttcaaagg caaaacggac tacgtgaaga agccagtttc aatggatggg atgctaacat     1200
ttcttgtgga actcgagaaa aacccgaagg gatatcttgt ctttgatcct tatggcggag     1260
ccatggacaa gattagtgat caagctattg cttctccctca tagaaaaggt aaccttttcg     1320
cgattcagta tctagcacag tggaatgaag aggacgatta catgagcgac gtttacatgg     1380
agtggataag aggattttac aatacaatga cgcccttgt  ttcaagctcg ccaaggggag     1440
cttatatcaa ctacttggat atggatcttg gagtgaatat ggtcgacgac tacttattgc     1500
gaaatgctag tagcagtagt ccttcttcct ctgttgatgc tgtggagaga gctagagcgt     1560
ggggtgagat gtatttcttg cataactatg ataggttggt taaagctaag acacaaattg     1620
atccactaaa tgtttttcga catgaacaga gtattcctcc tatgcttggt tcaacgcaag     1680
agcacaagta tagcagtgaa tgagatttaa aatgtactac cttgagagag attccgttgt     1740
tagttttcc                                                             1749
```

<210> SEQ ID NO 2
<211> LENGTH: 559
<212> TYPE: PRT
<213> ORGANISM: Nicotiana tabacum

<400> SEQUENCE: 2

```
Met Phe Pro Leu Ile Ile Leu Ile Ser Phe Ser Leu Ala Ser Leu Ser
1               5                   10                  15

Glu Thr Ala Thr Gly Ala Val Thr Asn Leu Ser Ala Cys Leu Ile Asn
            20                  25                  30

His Asn Val His Asn Phe Ser Ile Tyr Pro Thr Ser Arg Asn Tyr Phe
        35                  40                  45

Asn Leu Leu His Phe Ser Leu Gln Asn Leu Arg Phe Ala Ala Pro Phe
    50                  55                  60

Met Pro Lys Pro Thr Phe Ile Ile Leu Pro Ser Ser Lys Glu Glu Leu
65                  70                  75                  80

Val Ser Thr Ile Phe Cys Cys Arg Lys Ala Ser Tyr Glu Ile Arg Val
```

```
                        85                  90                  95
Arg Cys Gly Gly His Ser Tyr Glu Gly Thr Ser Tyr Val Ser Phe Asp
                100                 105                 110

Ala Ser Pro Phe Val Ile Val Asp Leu Met Lys Leu Asp Asp Val Ser
            115                 120                 125

Val Asp Leu Asp Ser Glu Thr Ala Trp Ala Gln Gly Gly Ala Thr Ile
        130                 135                 140

Gly Gln Ile Tyr Tyr Ala Ile Ala Lys Val Ser Asp Val His Ala Phe
145                 150                 155                 160

Ser Ala Gly Ser Gly Pro Thr Val Gly Ser Gly Gly His Ile Ser Gly
                165                 170                 175

Gly Gly Phe Gly Leu Leu Ser Arg Lys Phe Gly Leu Ala Ala Asp Asn
            180                 185                 190

Val Val Asp Ala Leu Leu Ile Asp Ala Asp Gly Arg Leu Leu Asp Arg
        195                 200                 205

Lys Ala Met Gly Glu Asp Val Phe Trp Ala Ile Arg Gly Gly Gly Gly
210                 215                 220

Gly Asn Trp Gly Ile Val Tyr Ala Trp Lys Ile Arg Leu Leu Lys Val
225                 230                 235                 240

Pro Lys Ile Val Thr Thr Cys Met Ile Tyr Arg Pro Gly Ser Lys Gln
                245                 250                 255

Tyr Val Ala Gln Ile Leu Glu Lys Trp Gln Ile Val Thr Pro Asn Leu
            260                 265                 270

Val Asp Asp Phe Thr Leu Gly Val Leu Leu Arg Pro Ala Asp Leu Pro
        275                 280                 285

Ala Asp Met Lys Tyr Gly Asn Thr Thr Pro Ile Glu Ile Phe Pro Gln
        290                 295                 300

Phe Asn Ala Leu Tyr Leu Gly Pro Lys Thr Glu Val Leu Ser Ile Ser
305                 310                 315                 320

Asn Glu Thr Phe Pro Glu Leu Gly Val Lys Asn Asp Glu Cys Lys Glu
                325                 330                 335

Met Thr Trp Val Glu Ser Ala Leu Phe Phe Ser Glu Leu Ala Asp Val
            340                 345                 350

Asn Gly Asn Ser Thr Gly Asp Ile Ser Arg Leu Lys Glu Arg Tyr Met
        355                 360                 365

Asp Gly Lys Gly Phe Phe Lys Gly Lys Thr Asp Tyr Val Lys Lys Pro
        370                 375                 380

Val Ser Met Asp Gly Met Leu Thr Phe Leu Val Glu Leu Glu Lys Asn
385                 390                 395                 400

Pro Lys Gly Tyr Leu Val Phe Asp Pro Tyr Gly Gly Ala Met Asp Lys
                405                 410                 415

Ile Ser Asp Gln Ala Ile Ala Phe Pro His Arg Lys Gly Asn Leu Phe
            420                 425                 430

Ala Ile Gln Tyr Leu Ala Gln Trp Asn Glu Glu Asp Asp Tyr Met Ser
        435                 440                 445

Asp Val Tyr Met Glu Trp Ile Arg Gly Phe Tyr Asn Thr Met Thr Pro
        450                 455                 460

Phe Val Ser Ser Ser Pro Arg Gly Ala Tyr Ile Asn Tyr Leu Asp Met
465                 470                 475                 480

Asp Leu Gly Val Asn Met Val Asp Asp Tyr Leu Leu Arg Asn Ala Ser
                485                 490                 495

Ser Ser Ser Pro Ser Ser Val Asp Ala Val Glu Arg Ala Arg Ala
            500                 505                 510
```

Trp Gly Glu Met Tyr Phe Leu His Asn Tyr Asp Arg Leu Val Lys Ala
            515                 520                 525

Lys Thr Gln Ile Asp Pro Leu Asn Val Phe Arg His Glu Gln Ser Ile
        530                 535                 540

Pro Pro Met Leu Gly Ser Thr Gln Glu His Lys Tyr Ser Ser Glu
545                 550                 555

<210> SEQ ID NO 3
<211> LENGTH: 1179
<212> TYPE: DNA
<213> ORGANISM: Nicotiana tabacum

<400> SEQUENCE: 3

| | | | | | |
|---|---|---|---|---|---|
| aaaaatccga | tttaattcct | agtttctagc | ccctccacct | taacccgaag | ctacttttt | 60 |
| tcttcccta | ggagtaaaat | ggttgtatca | gagaaaagca | agatcttaat | aattggaggc | 120 |
| acaggctaca | taggaaaata | cttggtggag | acaagtgcaa | aatctgggca | tccaactttc | 180 |
| gctcttatca | gagaaagcac | actcaaaaac | cccgagaaat | caaaactcat | cgacacattc | 240 |
| aagagttatg | gggttacgct | acttttttgga | gatatatcca | atcaagagag | cttactcaag | 300 |
| gcaatcaagc | aagttgatgt | ggtgatttcc | actgtcggag | gacagcaatt | tactgatcaa | 360 |
| gtgaacatca | tcaaagcaat | taaagaagct | ggaaatatca | agagatttct | tccttcagaa | 420 |
| tttggatttg | atgtggatca | tgctcgtgca | attgaaccag | ctgcatcact | cttcgctcta | 480 |
| aaggtaagaa | tcaggaggat | gatagaggca | gaaggaattc | catacacata | tgtaatctgc | 540 |
| aattggtttg | cagatttctt | cttgcccaac | ttggggcagt | tagaggccaa | aaccctcct | 600 |
| agagacaaag | ttgtcatttt | tggcgatgga | aatcccaaag | caatatatgt | gaaggaagaa | 660 |
| gacatagcga | catacactat | cgaagcagta | gatgatccac | ggacattgaa | taagactctt | 720 |
| cacatgagac | cacctgccaa | tattctatcc | ttcaacgaga | tagtgtcctt | gtgggaggac | 780 |
| aaaattggga | gaccctcga | gaagttatat | ctatcagagg | aagatattct | ccagattgta | 840 |
| caagagggac | ctctgccatt | aaggactaat | ttggccatat | gccattcagt | ttttgttaat | 900 |
| ggagattctg | caaactttga | ggttcagcct | cctacaggtg | tcgaagccac | tgagctatat | 960 |
| ccaaaagtga | atacacaac | cgtcgacgag | ttctacaaca | aatttgtcta | gtttgtcgat | 1020 |
| atcaatctgc | ggtgactcta | tcaaacttgt | tgtttctatg | aatctattga | gtgtaattgc | 1080 |
| aataattttc | gcttcagtgc | ttttgcaact | gaaatgtact | agctagttga | acgctagcta | 1140 |
| aattctttac | tgttgttttc | tattttcgt | cttattcca | | | 1179 |

<210> SEQ ID NO 4
<211> LENGTH: 310
<212> TYPE: PRT
<213> ORGANISM: Nicotiana tabacum

<400> SEQUENCE: 4

Met Val Val Ser Glu Lys Ser Lys Ile Leu Ile Gly Gly Thr Gly
1               5                   10                  15

Tyr Ile Gly Lys Tyr Leu Val Glu Thr Ser Ala Lys Ser Gly His Pro
            20                  25                  30

Thr Phe Ala Leu Ile Arg Glu Ser Thr Leu Lys Asn Pro Glu Lys Ser
        35                  40                  45

Lys Leu Ile Asp Thr Phe Lys Ser Tyr Gly Val Thr Leu Leu Phe Gly
    50                  55                  60

Asp Ile Ser Asn Gln Glu Ser Leu Leu Lys Ala Ile Lys Gln Val Asp

```
              65                  70                  75                  80
Val Val Ile Ser Thr Val Gly Gly Gln Gln Phe Thr Asp Gln Val Asn
                    85                  90                  95

Ile Ile Lys Ala Ile Lys Glu Ala Gly Asn Ile Lys Arg Phe Leu Pro
                100                 105                 110

Ser Glu Phe Gly Phe Asp Val Asp His Ala Arg Ala Ile Glu Pro Ala
                115                 120                 125

Ala Ser Leu Phe Ala Leu Lys Val Arg Ile Arg Arg Met Ile Glu Ala
130                 135                 140

Glu Gly Ile Pro Tyr Thr Tyr Val Ile Cys Asn Trp Phe Ala Asp Phe
145                 150                 155                 160

Phe Leu Pro Asn Leu Gly Gln Leu Glu Ala Lys Thr Pro Pro Arg Asp
                165                 170                 175

Lys Val Val Ile Phe Gly Asp Gly Asn Pro Lys Ala Ile Tyr Val Lys
                180                 185                 190

Glu Glu Asp Ile Ala Thr Tyr Thr Ile Glu Ala Val Asp Asp Pro Arg
                195                 200                 205

Thr Leu Asn Lys Thr Leu His Met Arg Pro Pro Ala Asn Ile Leu Ser
210                 215                 220

Phe Asn Glu Ile Val Ser Leu Trp Glu Asp Lys Ile Gly Lys Thr Leu
225                 230                 235                 240

Glu Lys Leu Tyr Leu Ser Glu Glu Asp Ile Leu Gln Ile Val Gln Glu
                245                 250                 255

Gly Pro Leu Pro Leu Arg Thr Asn Leu Ala Ile Cys His Ser Val Phe
                260                 265                 270

Val Asn Gly Asp Ser Ala Asn Phe Glu Val Gln Pro Pro Thr Gly Val
                275                 280                 285

Glu Ala Thr Glu Leu Tyr Pro Lys Val Lys Tyr Thr Thr Val Asp Glu
                290                 295                 300

Phe Tyr Asn Lys Phe Val
305                 310

<210> SEQ ID NO 5
<211> LENGTH: 1399
<212> TYPE: DNA
<213> ORGANISM: Nicotiana tabacum

<400> SEQUENCE: 5
caaaaactat tttccacaaa attcatttca caacccccccc aaaaaaaaac catgtttaga      60
gctattcctt tcactgctac agtgcatcct tatgcaatta cagctccaag gttggtggtg     120
aaaatgtcag caatagccac caagaataca agagtggagt cattagaggt gaaaccacca     180
gcacacccaa cttatgattt aaaggaagtt atgaaacttg cactctctga agatgctggg     240
aatttaggag atgtgacttg taggcgacaa attcctcttg atatggaatc cgatgctcat     300
tttctagcaa aggaagacgg gatcatagca ggaattgcac ttgctgagat gatattcgcg     360
gaagttgatc cttcattaaa ggtggagtgg tatgtaaatg atggcgataa agttcataaa     420
ggcttgaaat ttggcaaagt acaaggaaac gcttacaaca ttgttatagc tgagagggtt     480
gttctcaatt ttatgcaaag aatgagtgga atagctacac taactaagga atggcagat     540
gctgcacacc ctgcttacat cttggagact aggaaaactg ctcctggatt acgtttggtg     600
gataaatggg cggtattgat cggtgggggg aagaatcaca gaatgggctt atttgatatg     660
gtaatgataa aagacaatca catatctgct gctggaggtg tcggcaaagc tctaaaatct     720
```

-continued

```
gtggatcagt atttggagca aaataaactt caaataggggg ttgaggttga aaccaggaca    780
attgaagaag tacgtgaggt tctagactat gcatctcaaa caaagacttc gttgactagg    840
ataatgctgg acaatatggt tgttccatta tctaacggag atattgatgt atccatgctt    900
aaggaggctg tagaattgat caatgggagg tttgatacgg aggcttcagg aaatgttacc    960
cttgaaacag tacacaagat tggacaaact ggtgttacct acatttctag tggtgccctg   1020
acgcattccg tgaaagcact tgacatttcc ctgaagatcg atacagagct cgcccttgaa   1080
gttggaaggc gtacaaaacg agcatgagcg ccattacttc tgctataggg ttggagtaaa   1140
agcagctgaa tagctgaaag gtgcaaataa gaatcatttt actagttgtc aaacaaaaga   1200
tccttcactg tgtaatcaaa caaaaagatg taaattgctg gaatatctca gatggctctt   1260
ttccaacctt attgcttgag ttggtaattt cattatagct ttgttttcat gtttcatgga   1320
atttgttaca atgaaaatac ttgatttata agtttggtgt atgtaaaatt ctgtgttact   1380
tcaaatattt tgagatgtt                                                 1399
```

<210> SEQ ID NO 6
<211> LENGTH: 351
<212> TYPE: PRT
<213> ORGANISM: Nicotiana tabacum

<400> SEQUENCE: 6

```
Met Phe Arg Ala Ile Pro Phe Thr Ala Thr Val His Pro Tyr Ala Ile
1               5                   10                  15

Thr Ala Pro Arg Leu Val Val Lys Met Ser Ala Ile Ala Thr Lys Asn
            20                  25                  30

Thr Arg Val Glu Ser Leu Glu Val Lys Pro Pro Ala His Pro Thr Tyr
        35                  40                  45

Asp Leu Lys Glu Val Met Lys Leu Ala Leu Ser Glu Asp Ala Gly Asn
    50                  55                  60

Leu Gly Asp Val Thr Cys Lys Ala Thr Ile Pro Leu Asp Met Glu Ser
65                  70                  75                  80

Asp Ala His Phe Leu Ala Lys Glu Asp Gly Ile Ile Ala Gly Ile Ala
                85                  90                  95

Leu Ala Glu Met Ile Phe Ala Glu Val Asp Pro Ser Leu Lys Val Glu
            100                 105                 110

Trp Tyr Val Asn Asp Gly Asp Lys Val His Lys Gly Leu Lys Phe Gly
        115                 120                 125

Lys Val Gln Gly Asn Ala Tyr Asn Ile Val Ile Ala Glu Arg Val Val
    130                 135                 140

Leu Asn Phe Met Gln Arg Met Ser Gly Ile Ala Thr Leu Thr Lys Glu
145                 150                 155                 160

Met Ala Asp Ala Ala His Pro Ala Tyr Ile Leu Glu Thr Arg Lys Thr
                165                 170                 175

Ala Pro Gly Leu Arg Leu Val Asp Lys Trp Ala Val Leu Ile Gly Gly
            180                 185                 190

Gly Lys Asn His Arg Met Gly Leu Phe Asp Met Val Met Ile Lys Asp
        195                 200                 205

Asn His Ile Ser Ala Ala Gly Gly Val Gly Lys Ala Leu Lys Ser Val
    210                 215                 220

Asp Gln Tyr Leu Glu Gln Asn Lys Leu Gln Ile Gly Val Glu Val Glu
225                 230                 235                 240

Thr Arg Thr Ile Glu Glu Val Arg Glu Val Leu Asp Tyr Ala Ser Gln
                245                 250                 255
```

```
            Thr Lys Thr Ser Leu Thr Arg Ile Met Leu Asp Asn Met Val Val Pro
                    260                 265                 270

Leu Ser Asn Gly Asp Ile Asp Val Ser Met Leu Lys Glu Ala Val Glu
                    275                 280                 285

Leu Ile Asn Gly Arg Phe Asp Thr Glu Ala Ser Gly Asn Val Thr Leu
                    290                 295                 300

Glu Thr Val His Lys Ile Gly Gln Thr Gly Val Thr Tyr Ile Ser Ser
            305                 310                 315                 320

Gly Ala Leu Thr His Ser Val Lys Ala Leu Asp Ile Ser Leu Lys Ile
                            325                 330                 335

Asp Thr Glu Leu Ala Leu Glu Val Gly Arg Arg Thr Lys Arg Ala
                        340                 345                 350

<210> SEQ ID NO 7
<211> LENGTH: 1386
<212> TYPE: DNA
<213> ORGANISM: Nicotiana tabacum

<400> SEQUENCE: 7
ggaaaataca aaccataata ctttctcttc ttcaatttgt ttagtttaat tttgaaaatg      60
gaagtcatat ctaccaacac aaatggctct accatcttca agaatggtgc cattcccatg     120
aacggccacc aaaatggcac ttctgaacac ctcaacggct accagaatgg cacttccaaa     180
caccaaaacg ggcaccagaa tggcactttc gaacatcgga acggccacca gaatgggaca     240
tccgaacaac agaacgggac aatcagccat gacaatggca acgagctact gggaagctcc     300
gactctatta agcctggctg gttttcagag tttagcgcat atggccaggt gaagcattc     360 tcacttaagg ttgagaagtt actattccag gggaagtctg attaccaaga tgtcatgctc     420
tttgagtcag caacttatgg aaggttctg actttggatg gagcaattca acatacagag     480
aatggtggat ttccatacac tgaaatgatt gttcatctac cacttggttc catcccaaac     540
ccaaaaaagg ttttgatcat cggcggagga attggtttta cattattcga aatgcttcgt     600
tatccttcaa tcgaaaaaat tgacattgtt gagatcgatg acgtggtagt tgatgtatcc     660
agaaaatttt tcccttatct ggcagctaat tttaacgatc ctcgtgtaac cctagttctc     720
ggagatggag ctgcatttgt aaaggctgca caagcgggat attatgatgc tattatagtg     780
gactcttctg atcccattgg tccagcaaaa gatttgtttg agaggccatt ctttgaggca     840
gtagccaaag cccttaggcc aggaggagtt gtatgcacac aggctgaaag catttggctt     900
catatgcata ttattaagca aatcattgct aactgtcgtc aagtctttaa gggttctgtc     960
aactatgctt ggacaaccgc tccaacatat cccaccggtg tgatcggtta tgctctgc    1020 tctactgaag ggccagaagt tgacttcaag aatccagtaa atccaattga caaagagaca    1080
actcaagtca gtccaaatt aggacctctc aagttctaca actctgatat tcacaaagca    1140
gcattcattt taccatcttt cgccagaagt atgatcgagt cttaatcaag tgaataatga    1200
acactggtag tacaatcatt ggaccaagat cgagtcttaa tcaagtgaat aaataagtga    1260
aatgcgacgt attgtaggag aattctgcag taattatcat aatttccaat tcacaatcat    1320
tgtaaaattc tttctctgtg gtgtttcgta ctttaatata aattttcctg ctgaagtttt    1380
gaatcg                                                              1386

<210> SEQ ID NO 8
<211> LENGTH: 375
<212> TYPE: PRT
```

<213> ORGANISM: Nicotiana tabacum

<400> SEQUENCE: 8

```
Met Glu Val Ile Ser Thr Asn Thr Asn Gly Ser Thr Ile Phe Lys Asn
1               5                   10                  15

Gly Ala Ile Pro Met Asn Gly His Gln Asn Gly Thr Ser Glu His Leu
            20                  25                  30

Asn Gly Tyr Gln Asn Gly Thr Ser Lys His Gln Asn Gly His Gln Asn
        35                  40                  45

Gly Thr Phe Glu His Arg Asn Gly His Gln Asn Gly Thr Ser Glu Gln
    50                  55                  60

Gln Asn Gly Thr Ile Ser His Asp Asn Gly Asn Glu Leu Leu Gly Ser
65                  70                  75                  80

Ser Asp Ser Ile Lys Pro Gly Trp Phe Ser Glu Phe Ser Ala Leu Trp
                85                  90                  95

Pro Gly Glu Ala Phe Ser Leu Lys Val Glu Lys Leu Leu Phe Gln Gly
            100                 105                 110

Lys Ser Asp Tyr Gln Asp Val Met Leu Phe Glu Ser Ala Thr Tyr Gly
        115                 120                 125

Lys Val Leu Thr Leu Asp Gly Ala Ile Gln His Thr Glu Asn Gly Gly
    130                 135                 140

Phe Pro Tyr Thr Glu Met Ile Val His Leu Pro Leu Gly Ser Ile Pro
145                 150                 155                 160

Asn Pro Lys Lys Val Leu Ile Ile Gly Gly Gly Ile Gly Phe Thr Leu
                165                 170                 175

Phe Glu Met Leu Arg Tyr Pro Ser Ile Glu Lys Ile Asp Ile Val Glu
            180                 185                 190

Ile Asp Asp Val Val Asp Val Ser Arg Lys Phe Phe Pro Tyr Leu
        195                 200                 205

Ala Ala Asn Phe Asn Asp Pro Arg Val Thr Leu Val Leu Gly Asp Gly
    210                 215                 220

Ala Ala Phe Val Lys Ala Ala Gln Ala Gly Tyr Tyr Asp Ala Ile Ile
225                 230                 235                 240

Val Asp Ser Ser Asp Pro Ile Gly Pro Ala Lys Asp Leu Phe Glu Arg
                245                 250                 255

Pro Phe Phe Glu Ala Val Ala Lys Ala Leu Arg Pro Gly Gly Val Val
            260                 265                 270

Cys Thr Gln Ala Glu Ser Ile Trp Leu His Met His Ile Ile Lys Gln
        275                 280                 285

Ile Ile Ala Asn Cys Arg Gln Val Phe Lys Gly Ser Val Asn Tyr Ala
    290                 295                 300

Trp Thr Thr Ala Pro Thr Tyr Pro Thr Gly Val Ile Gly Tyr Met Leu
305                 310                 315                 320

Cys Ser Thr Glu Gly Pro Glu Val Asp Phe Lys Asn Pro Val Asn Pro
                325                 330                 335

Ile Asp Lys Glu Thr Thr Gln Val Lys Ser Lys Leu Gly Pro Leu Lys
            340                 345                 350

Phe Tyr Asn Ser Asp Ile His Lys Ala Ala Phe Ile Leu Pro Ser Phe
        355                 360                 365

Ala Arg Ser Met Ile Glu Ser
    370                 375
```

<210> SEQ ID NO 9
<211> LENGTH: 1680

<212> TYPE: DNA
<213> ORGANISM: Nicotiana tabacum

<400> SEQUENCE: 9

```
atgtttccgc tcataattct gatcagcttt tcacttgctt ccttgtctga aactgctact    60
ggagctgtta caaatctttc agcctgctta atcaaccaca atgtccataa cttctctatt   120
taccccacaa gtagaaatta ctttaacttg ctccacttct cccttcaaaa tcttcgcttt   180
gctgcacctt tcatgccgaa accaaccttc attatcctac caagcagtaa ggaggagctc   240
gtgagcacca ttttttgttg cagaaaagca tcttatgaaa tcagagtaag gtgcggcgga   300
cacagttacg aaggaacttc ttacgtttcc tttgacgctt ctccattcgt gatcgttgac   360
ttgatgaaat tagacgacgt ttcagtagat ttggattctg aaacagcttg gctcagggc    420
ggcgcaacaa ttggccaaat ttattatgcc attgccaagg taagtgacgt tcatgcattt   480
tcagcaggtt cgggaccaac agtaggatct ggaggtcata tttcaggtgg tggatttgga   540
cttttatcta gaaaattcgg acttgctgct gataatgtcg ttgatgctct tcttattgat   600
gctgatggac ggttattaga ccgaaaagcc atgggcgaag acgtgttttg gcaatcaga    660
ggtggcggcg gtgaaaattg gggcattgtt tatgcctgga aaattcgatt actcaaagtg   720
cctaaaatcg taacaacttg tatgatctat aggcctggat ccaaacaata cgtggctcaa   780
atacttgaga atggcaaat agttactcca aatttggtcg atgattttac tctaggagta    840
ctgctgagac ctgcagatct acccgcggat atgaaatatg gtaatactac tcctattgaa   900
atatttcccc aattcaatgc actttatttg ggtccaaaaa ctgaagttct ttccatatcg   960
aatgagacat ttccggagct aggcgttaag aatgatgagt gcaaggaaat gacttgggta  1020
gagtcagcac ttttcttctc cgaattagct gacgttaacg ggaactcgac tggtgatatc  1080
tcccgtctga agaacgttac catggacgga aaaggttttt tcaaaggcaa aacggactac  1140
gtgaagaagc cagtttcaat ggatgggatg ctaacatttc ttgtggaact cgagaaaaac  1200
ccgaagggat atcttgtctt tgatccttat ggcggagcca tggacaagat tagtgatcaa  1260
gctattgctt tccctcatag aaaaggtaac cttttcgcga ttcagtatct agcacagtgg  1320
aatgaagagg acgattacat gagcgacgtt tacatggagt ggataagagg atttacaat   1380
acaatgacgc cctttgtttc aagctcgcca aggggagctt atatcaacta cttggatatg  1440
gatcttggag tgaatatggt cgacgactac ttattgcgaa atgctagtag cagtagtcct  1500
tcttcctctg ttgatgctgt ggagagagct agagcgtggg gtgagatgta tttcttgcat  1560
aactatgata ggttggttaa agctaagaca caaattgatc cactaaatgt ttttcgacat  1620
gaacagagta ttcctcctat gcttggttca acgcaagagc acaagtatag cagtgaatga  1680
```

<210> SEQ ID NO 10
<211> LENGTH: 933
<212> TYPE: DNA
<213> ORGANISM: Nicotiana tabacum

<400> SEQUENCE: 10

```
atggttgtat cagagaaaag caagatctta ataattggag gcacaggcta cataggaaaa     60
tacttggtgg agacaagtgc aaaatctggg catccaactt cgctcttat cagagaaagc    120
acactcaaaa accccgagaa atcaaaactc atcgacacat tcaagagtta tggggttacg    180
ctactttttg gagatatatc caatcaagag agcttactca aggcaatcaa gcaagttgat    240
gtggtgattt ccactgtcgg aggacagcaa tttactgatc aagtgaacat catcaaagca    300
```

| | |
|---|---|
| attaaagaag ctggaaatat caagagattt cttccttcag aatttggatt tgatgtggat | 360 |
| catgctcgtg caattgaacc agctgcatca ctcttcgctc taaaggtaag aatcaggagg | 420 |
| atgatagagg cagaaggaat tccatacaca tatgtaatct gcaattggtt tgcagatttc | 480 |
| ttcttgccca acttggggca gttagaggcc aaaacccctc ctagagacaa agttgtcatt | 540 |
| tttggcgatg gaaatcccaa agcaatatat gtgaaggaag aagacatagc gacatacact | 600 |
| atcgaagcag tagatgatcc acggacattg aataagactc ttcacatgag accacctgcc | 660 |
| aatattctat ccttcaacga gatagtgtcc ttgtgggagg acaaaattgg gaagaccctc | 720 |
| gagaagttat atctatcaga ggaagatatt ctccagattg tacaagaggg acctctgcca | 780 |
| ttaaggacta atttggccat atgccattca gttttttgtta atggagattc tgcaaacttt | 840 |
| gaggttcagc ctcctacagg tgtcgaagcc actgagctat atccaaaagt gaaatacaca | 900 |
| accgtcgacg agttctacaa caaatttgtc tag | 933 |

<210> SEQ ID NO 11
<211> LENGTH: 1056
<212> TYPE: DNA
<213> ORGANISM: Nicotiana tabacum

<400> SEQUENCE: 11

| | |
|---|---|
| atgtttagag ctattccttt cactgctaca gtgcatcctt atgcaattac agctccaagg | 60 |
| ttggtggtga aaatgtcagc aatagccacc aagaatacaa gagtggagtc attagaggtg | 120 |
| aaaccaccag cacacccaac ttatgattta aaggaagtta tgaaacttgc actctctgaa | 180 |
| gatgctggga atttaggaga tgtgacttgt aaggcgacaa ttcctcttga tatggaatcc | 240 |
| gatgctcatt ttctagcaaa ggaagacggg atcatagcag gaattgcact tgctgagatg | 300 |
| atattcgcgg aagttgatcc ttcattaaag gtggagtggt atgtaaatga tggcgataaa | 360 |
| gttcataaag gcttgaaatt tggcaaagta caaggaaacg cttacaacat tgttatagct | 420 |
| gagagggttg ttctcaattt tatgcaaaga atgagtggaa tagctacact aactaaggaa | 480 |
| atggcagatg ctgcacaccc tgcttacatc ttggagacta ggaaaactgc tcctggatta | 540 |
| cgtttggtgg ataaatgggc ggtattgatc ggtgggggga agaatcacag aatgggctta | 600 |
| tttgatatgg taatgataaa agacaatcac atatctgctg ctggaggtgt cggcaaagct | 660 |
| ctaaaatctg tggatcagta tttggagcaa aataaacttc aaataggggt tgaggttgaa | 720 |
| accaggacaa ttgaagaagt acgtgaggtt ctagactatg catctcaaac aaagacttcg | 780 |
| ttgactagga taatgctgga caatatggtt gttccattat ctaacggaga tattgatgta | 840 |
| tccatgctta aggaggctgt agaattgatc aatgggaggt ttgatacgga ggcttcagga | 900 |
| aatgttaccc ttgaaacagt acacaagatt ggacaaactg tgttaccta catttctagt | 960 |
| ggtgccctga cgcattccgt gaaagcactt gacatttccc tgaagatcga tacagagctc | 1020 |
| gcccttgaag atggaaggcg tacaaaacga gcatga | 1056 |

<210> SEQ ID NO 12
<211> LENGTH: 1128
<212> TYPE: DNA
<213> ORGANISM: Nicotiana tabacum

<400> SEQUENCE: 12

| | |
|---|---|
| atggaagtca tatctaccaa cacaaatggc tctaccatct tcaagaatgg tgccattccc | 60 |
| atgaacggcc accaaaatgg cacttctgaa cacctcaacg gctaccagaa tggcacttcc | 120 |
| aaacaccaaa acgggcacca gaatggcact ttcgaacatc ggaacggcca ccagaatggg | 180 |

```
acatccgaac aacagaacgg gacaatcagc catgacaatg gcaacgagct actgggaagc    240
tccgactcta ttaagcctgg ctggttttca gagtttagcg cattatggcc aggtgaagca    300
ttctcactta aggttgagaa gttactattc caggggaagt ctgattacca agatgtcatg    360
ctctttgagt cagcaactta tgggaaggtt ctgactttgg atggagcaat tcaacataca    420
gagaatggtg gatttccata cactgaaatg attgttcatc taccacttgg ttccatccca    480
aacccaaaaa aggttttgat catcggcgga ggaattggtt ttacattatt cgaaatgctt    540
cgttatcctt caatcgaaaa aattgacatt gttgagatcg atgacgtggt agttgatgta    600
tccagaaaat ttttcccctta tctggcagct aatttttaacg atcctcgtgt aaccctagtt    660
ctcggagatg gagctgcatt tgtaaaggct gcacaagcgg gatattatga tgctattata    720
gtggactctt ctgatcccat tggtccagca aaagatttgt ttgagaggcc attctttgag    780
gcagtagcca aagcccttag gccaggagga gttgtatgca cacaggctga aagcatttgg    840
cttcatatgc atattattaa gcaaatcatt gctaactgtc gtcaagtctt taagggttct    900
gtcaactatg cttggacaac cgctccaaca tatcccaccg gtgtgatcgg ttatatgctc    960
tgctctactg aagggccaga agttgacttc aagaatccag taaatccaat tgacaaagag    1020
acaactcaag tcaagtccaa attaggacct ctcaagttct acaactctga tattcacaaa    1080
gcagcattca ttttaccatc tttcgccaga agtatgatcg agtcttaa                 1128
```

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaaaactaa caacggaatc tct                                             23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gatcaagcta ttgctttccc t                                               21

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaaaagcagg ctcaccatgt ttccgctcat aattctg                              37

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
agaaagctgg gttcattcac tgctatactt gtgc                                34

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggggacaagt ttgtacaaaa aagcaggct                                      29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggggaccact ttgtacaaga aagctgggt                                      29

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaagcttgga aacatattca atacattgta g                                   31

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctagattct actactattt tataagtg                                       28

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaaagcagg cttcgaagga gatagaacca tggttgtatc agagaaaagc a             51

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 22
agaaagctgg gtcctagaca aatttgttgt agaactcgtc g                            41

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaagcttag atctctctta tgtttcatg                                          29

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tctagattta ctcctagggg aagaaaaaaa gtagc                                   35

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aaaaagcagg ctcaaaaatg gaagtcatat c                                       31

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agaaagctgg gtttaagact cgatcatact tc                                      32

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caccatgttt agagctattc c                                                  21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 28
tcatgctcgt tttgtacgcc                                                    20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acccttcctc tatataagga ag                                                 22

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgagcccaag ctgtttcaga atcc                                               24

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acccttcctc tatataagga ag                                                 22

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgctaaactc tgaaaaccag c                                                  21

<210> SEQ ID NO 33
<211> LENGTH: 538
<212> TYPE: PRT
<213> ORGANISM: Eschscholzia californica

<400> SEQUENCE: 33

Met Glu Asn Lys Thr Pro Ile Phe Phe Ser Leu Ser Ile Phe Leu Ser
1               5                   10                  15

Leu Leu Asn Cys Ala Leu Gly Gly Asn Asp Leu Leu Ser Cys Leu Thr
            20                  25                  30

Phe Asn Gly Val Arg Asn His Thr Val Phe Ser Ala Asp Ser Asp Ser
        35                  40                  45

Asp Phe Asn Arg Phe Leu His Leu Ser Ile Gln Asn Pro Leu Phe Gln
    50                  55                  60

Asn Ser Leu Ile Ser Lys Pro Ser Ala Ile Ile Leu Pro Gly Ser Lys
65                  70                  75                  80

-continued

```
Glu Glu Leu Ser Asn Thr Ile Arg Cys Ile Arg Lys Gly Ser Trp Thr
                85                  90                  95

Ile Arg Leu Arg Ser Gly Gly His Ser Tyr Glu Gly Leu Ser Tyr Thr
            100                 105                 110

Ser Asp Thr Pro Phe Ile Leu Ile Asp Leu Met Asn Leu Asn Arg Val
        115                 120                 125

Ser Ile Asp Leu Glu Ser Glu Thr Ala Trp Val Glu Ser Gly Ser Thr
130                 135                 140

Leu Gly Glu Leu Tyr Tyr Ala Ile Thr Glu Ser Ser Lys Leu Gly
145                 150                 155                 160

Phe Thr Ala Gly Trp Cys Pro Thr Val Gly Thr Gly His Ile Ser
                165                 170                 175

Gly Gly Gly Phe Gly Met Met Ser Arg Lys Tyr Gly Leu Ala Ala Asp
            180                 185                 190

Asn Val Val Asp Ala Ile Leu Ile Asp Ala Asn Gly Ala Ile Leu Asp
        195                 200                 205

Arg Gln Ala Met Gly Glu Asp Val Phe Trp Ala Ile Arg Gly Gly Gly
210                 215                 220

Gly Gly Val Trp Gly Ala Ile Tyr Ala Trp Lys Ile Lys Leu Leu Pro
225                 230                 235                 240

Val Pro Glu Lys Val Thr Val Phe Arg Val Thr Lys Asn Val Ala Ile
                245                 250                 255

Asp Glu Ala Thr Ser Leu Leu His Lys Trp Gln Phe Val Ala Glu Glu
            260                 265                 270

Leu Glu Glu Asp Phe Thr Leu Ser Val Leu Gly Gly Ala Asp Glu Lys
        275                 280                 285

Gln Val Trp Leu Thr Met Leu Gly Phe His Phe Gly Leu Lys Thr Val
290                 295                 300

Ala Lys Ser Thr Phe Asp Leu Leu Phe Pro Glu Leu Gly Leu Val Glu
305                 310                 315                 320

Glu Asp Tyr Leu Glu Met Ser Trp Gly Glu Ser Phe Ala Tyr Leu Ala
                325                 330                 335

Gly Leu Glu Thr Val Ser Gln Leu Asn Asn Arg Phe Leu Lys Phe Asp
            340                 345                 350

Glu Arg Ala Phe Lys Thr Lys Val Asp Leu Thr Lys Glu Pro Leu Pro
        355                 360                 365

Ser Lys Ala Phe Tyr Gly Leu Leu Glu Arg Leu Ser Lys Glu Pro Asn
        370                 375                 380

Gly Phe Ile Ala Leu Asn Gly Phe Gly Gly Gln Met Ser Lys Ile Ser
385                 390                 395                 400

Ser Asp Phe Thr Pro Phe Pro His Arg Ser Gly Thr Arg Leu Met Val
                405                 410                 415

Glu Tyr Ile Val Ala Trp Asn Gln Ser Glu Gln Lys Lys Lys Thr Glu
            420                 425                 430

Phe Leu Asp Trp Leu Glu Lys Val Tyr Glu Phe Met Lys Pro Phe Val
        435                 440                 445

Ser Lys Asn Pro Arg Leu Gly Tyr Val Asn His Ile Asp Leu Asp Leu
        450                 455                 460

Gly Gly Ile Asp Trp Gly Asn Lys Thr Val Val Asn Asn Ala Ile Glu
465                 470                 475                 480

Ile Ser Arg Ser Trp Gly Glu Ser Tyr Phe Leu Ser Asn Tyr Glu Arg
                485                 490                 495

Leu Ile Arg Ala Lys Thr Leu Ile Asp Pro Asn Asn Val Phe Asn His
```

```
                500             505             510
Pro Gln Ser Ile Pro Pro Met Ala Asn Phe Asp Tyr Leu Glu Lys Thr
        515                 520                 525

Leu Gly Ser Asp Gly Gly Glu Val Val Ile
    530                 535

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5
```

INCREASING LEVELS OF NICOTINIC ALKALOIDS IN PLANTS

CROSS-REFERENCE TO RELATED APPLICATIONS

This application is a continuation of U.S. patent application Ser. No. 16/258,393, filed Jan. 25, 2019, which is a divisional of U.S. patent application Ser. No. 15/411,721, filed Jan. 20, 2017, now U.S. Pat. No. 10,190,129, which is a divisional of U.S. patent application Ser. No. 11/520,036, filed Sep. 13, 2006, now U.S. Pat. No. 9,551,003. The contents of these applications are incorporated herein by reference in their entirety.

SEQUENCE LISTING

The instant application contains a Sequence Listing which has been submitted electronically in ASCII format and is hereby incorporated by reference in its entirety.

FIELD OF THE INVENTION

The present invention relates to the field of molecular biology and regulation of nicotinic alkaloid synthesis. Thus, the invention relates, inter alia, to methodology and constructs for increasing the level of nicotinic alkaloids in a Nicotiana plant, and to cells that are genetically engineered to produce nicotinic alkaloids and related compounds, when they would not do so otherwise.

BACKGROUND OF THE INVENTION

Presently, several nicotine biosynthesis enzymes are known. For example, the tobacco quinolate phosphoribosyl transferase (QPT) gene has been cloned, see U.S. Pat. No. 6,423,520 and Sinclair et al., *Plant Mol. Biol.* 44: 603-17 (2000), and its suppression provides significant nicotine reductions in transgenic tobacco plants. Xie et al., *Recent Advances in Tobacco Science* 30: 17-37 (2004). Likewise, suppression of an endogenous putrescine methyl transferase (PMT) sequence has been shown to reduce nicotine levels but increase anatabine levels by about 2-to-6-fold. Hibi et al., *Plant Cell* 6: 723-35 (1994); Chintapakorn and Hamill, *Plant Mol. Biol.* 53:87-105 (2003); Steppuhn et al. *PLoS Biol* 2:8:e217:1074-1080 (2004).

While previous research efforts have focused on using nicotine biosynthesis enzymes for reducing nicotine in plants, very little research has addressed the role of nicotine biosynthesis enzymes in increasing nicotinic alkaloid synthesis. This lack of up-regulation data may be attributed to the fact that overexpressing a known nicotinic alkaloid biosynthesis gene, such as PMT, or QPT, will not necessarily increase plant production and accumulation of secondary metabolites. That is, it does not necessarily follow that because down-regulating a nicotinic alkaloid biosynthesis gene reduces alkaloid production and accumulation, overexpressing the same nicotinic alkaloid biosynthesis gene will increase nicotinic alkaloid production and accumulation.

Due to the paucity of research, there is a need for identifying genes that increase nicotine biosynthesis and accumulation. For example, because nicotinic alkaloids play an important role in protecting plants against insects and herbivores, it is likely to be advantageous to increase nicotinic alkaloid synthesis in a host plant. From an herbivory perspective, increased nicotine synthesis and accumulation would provide an environmentally acceptable means for mediating plant-pest interactions.

From the cigarette industry's perspective, where nicotine is the physically and psychologically active component in cigarette smoke, it may be advantageous to increase nicotine content in tobacco by genetic engineering. Research studies demonstrate that when supplementary nicotine is physically added to cigarette tobacco from an outside source, smokers inhale less of the more harmful components of smoke such as tar and carbon monoxide. See Armitage et al., *Psychopharmacology* 96: 447-53 (1988), Fagerström, *Psychopharmacology* 77: 164-67 (1982), Russell, *Nicotine and Public Health* 15: 265-84 (2000), and Woodman et al., *European Journal of Respiratory Disease* 70: 316-21 (1987). Likewise, a report by The Institute of Medicine of the U.S. on potential reduced-exposure products (PREPs) concluded that "retaining nicotine at pleasurable or addictive levels while reducing the more toxic components of tobacco is another general strategy for harm reduction." See CLEARING THE SMOKE, ASSESSING THE SCIENCE BASE FOR TOBACCO HARM REDUCTION, IOM at page 29 (2001); commonly referred to as the "IOM Report" by the tobacco industry.

In addition to the more traditional applications for increased nicotine products, such as cigarettes and other tobacco products, recent pharmacological studies suggest a therapeutic role for nicotine and related compounds. For example, several research groups are presently studying drugs that target nicotine receptors as a means for treating cognitive impairments, such as Alzheimer's disease, schizophrenia, and age-related memory loss. Singer, "The Upside to Nicotine," *Technology Review* (Jul. 28, 2006). Acetylcholine receptor ligands, such as nicotine, have been demonstrated to have effects on attention, cognition, appetite, substance abuse, memory, extra pyramidal function, cardiovascular function, pain, and gastrointestinal motility and function. U.S. Pat. No. 5,852,041. Thus, there are therapeutic benefits of nicotine and related compounds, and thus there is a need for improved methods for producing them.

Accordingly, there is a continuing need to identify additional genes whose expression can be affected to increase nicotinic alkaloid content in plants, in particular, nicotine in *N. tabacum* plants, as well as produce nicotine and related compounds in non-nicotine producing cells.

SUMMARY OF THE INVENTION

Four genes, A622, NBB1, PMT and QPT, can be influenced for increasing nicotinic alkaloid levels in *Nicotiana* plants, as well as synthesizing nicotinic alkaloids and related compounds in non-nicotine producing cells.

In one aspect, the invention provides a method for increasing nicotinic alkaloids, such as nicotine, in a *Nicotiana* plant, by overexpressing at least one of A622 and NBB1 relative to a control plant. In one embodiment, A622 is overexpressed. In another embodiment, NBB1 is overexpressed. In another embodiment, A622 and NBB1 are overexpressed. In a further embodiment, A622 and NBB1 are overexpressed and at least one of QPT and PMT is overexpressed. In a still further embodiment, QPT and A622 are overexpressed.

In another embodiment, an increased nicotine plant, and products there from, are produced by any method overexpressing one or more of A622, NBB1, PMT, and QPT. In a further embodiment, products are selected from the group consisting of a cigarette, a pharmaceutical, and a nutraceutical.

In another aspect, the invention provides a method for producing nicotinic alkaloids, comprising expressing NBB1 and A622 heterologously in a plant or cell that otherwise does not produce nicotinic alkaloids. In one embodiment, NBB1 and A622 expression occurs in a cell selected from the group consisting of a bacterial, yeast, filamentous fungi, algae, mammalian, and insect cell.

In another embodiment, an increased nicotinic alkaloid plant is produced by expressing NBB1 and A622 heterologously in a plant or cell that otherwise does not produce nicotinic alkaloids. In another embodiment, a nicotinic alkaloid product is produced by expressing NBB1 and A622 heterologously in a plant or cell that otherwise does not produce nicotinic alkaloids.

In another aspect, there is provided a method for the commercial production of a nicotinic alkaloid, comprising (a) providing a plurality of cells expressing A622 and NBB1 and (b) obtaining said nicotinic alkaloid from said plurality.

In another aspect, the invention provides a method for increasing nicotine in a plant, comprising overexpressing PMT and QPT relative to a control plant. In one embodiment, an increased nicotine plant is produced. In another embodiment, an increased nicotine product in produced.

In another aspect, the invention provides a method of producing NBB1 enzyme, comprising transforming a cell with an isolated nucleic molecule encoding NBB1 and growing the transformed cell under conditions whereby NBB1 enzyme is produced. In one embodiment, the transformed cell is selected from the group consisting of bacteria, yeast, filamentous fungi, algae, green plants, and mammalian cells.

In another aspect, the invention provides a method for increasing nicotine and yield in a *Nicotiana* plant, comprising a) crossing an increased-nicotine *Nicotiana* plant with a high yielding *Nicotiana* plant; and b) selecting an increased-nicotine and yield *Nicotiana* progeny plant. In one embodiment, an increased nicotine and yield plant is produced.

In one embodiment, the increased-nicotine plant is produced by: a) transforming a *Nicotiana* plant with a construct comprising, in the 5' to 3' direction, a promoter operably linked to a heterologous nucleic acid encoding an enzyme that increases nicotine synthesis; b) regenerating transgenic *Nicotiana* plants from the transformed plant; and c) selecting a transgenic *Nicotiana* plant having increased-nicotine content relative to a control plant. In a further embodiment, the nucleic acid is selected from the group consisting of QPT, PMT, A622, and NBB1.

In another aspect, the invention provides a method for increasing nicotine and yield in a *Nicotiana* plant, comprising: (a) transforming a *Nicotiana* plant with (i) a first construct comprising, in the 5' to 3' direction, a promoter operably linked to a heterologous nucleic acid encoding an enzyme that increases nicotine synthesis; and (ii) a second construct comprising, in the 5' to 3' direction, a promoter operably linked to a heterologous nucleic acid encoding an enzyme that increases yield; (b) regenerating transgenic *Nicotiana* plants from the transformed plant; and (c) selecting a transgenic *Nicotiana* plant having increased-nicotine content and increased yield relative to a control plant.

In one embodiment, the first construct comprises a nucleic acid encoding an enzyme selected from the group consisting of QPT, PMT, A622, and NBB1. In another embodiment, an increased nicotine and yield plant is produced.

In another aspect, the invention provides a method for increasing nicotine in *N. tabacum*, comprising overexpressing PMT relative to a control plant.

BRIEF DESCRIPTION OF THE DRAWINGS

FIG. 2: Alignment of NBB1 with *Eschscholzia californica* berberine bridge enzyme (EcBBE)(SEQ ID Nos: 2 and 33).
FIG. 13: Nicotine content in leaf of tobacco plants transformed with TobRD2-PMTox (TP-1 to TP-14). TG-1 to TG-3 are control plants transformed with TobRD2-GUS
FIG. 16: Nicotine content in leaf of tobacco plants transformed with A622pro-PMTox-QPTox (APQ-1 to APQ-27). AG-1 to AG-3 are control plants transformed with A622-GUS
FIG. 17: Nicotine content in leaf of tobacco plants transformed with pTobRD2-PMTox-QPTox (TPQ-1 to TPQ-24). TG-1 to TG-3 are control plants transformed with TobRD2-GUS

DETAILED DESCRIPTION OF THE INVENTION

Figure 1:
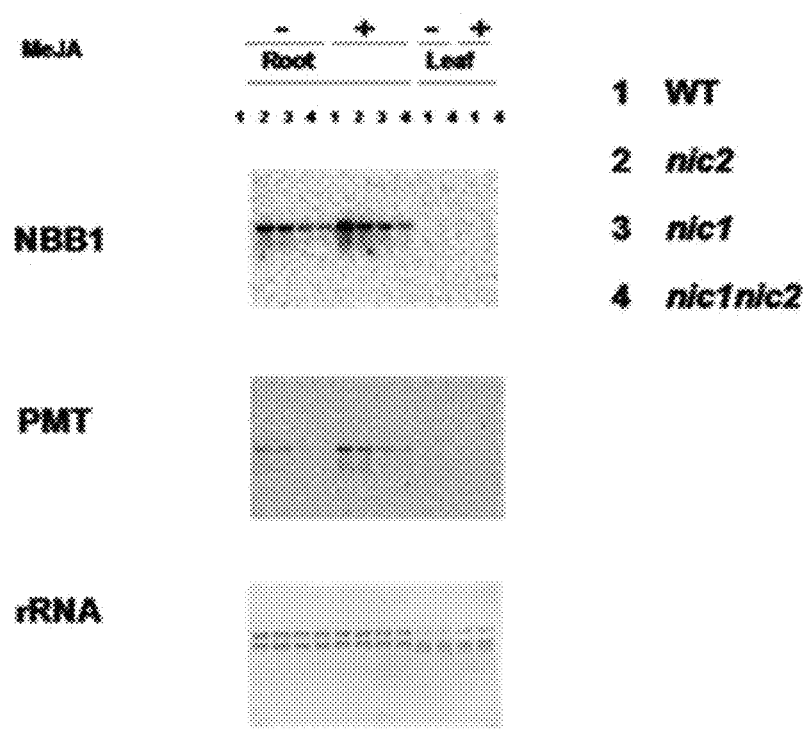
FIG. 1: RNA blot analysis of NBB1 expression

The present invention relates to increasing nicotinic alkaloids in *Nicotiana* plants, as well as to producing nicotinic alkaloids in cells that would not do so otherwise. As described below, the present inventors realized that four genes, A622, NBB1, QPT and PMT, can be influenced to achieve an increase of nicotinic alkaloid levels in *Nicotiana* plants. That is, overexpressing any of these four genes increases *Nicotiana* nicotinic alkaloids. Further increases in *Nicotiana* nicotinic alkaloids can be achieved by simultaneously overexpressing at least two of the four genes, such as QPT and PMT. A622 and NBB1 can be introduced into non-nicotine producing plants or cells, thereby to effect their production of nicotine or related compounds.

In addition to providing methodology for increasing nicotinic alkaloids in *Nicotiana*, the invention also provides for concurrently increasing nicotinic alkaloids and yield in *Nicotiana*. Pursuant to this aspect of the invention, increased nicotinic alkaloids and yield can be achieved by a combination of genetic engineering techniques and conventional breeding.

All technical terms employed in this specification are commonly used in biochemistry, molecular biology and agriculture; hence, they are understood by those skilled in the field to which this invention belongs. Those technical terms can be found, for example in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, 5$^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997; PRODUCTION, CHEMISTRY AND TECHNOLOGY, D. L. Davis and M. T. Nielson (eds.) Coresta, 1999 (commonly referred to as "IOM Report").

Methodology involving plant biology techniques are described here and also are described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, for example, in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, 2$^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, Mass. Methods for chemical synthesis of nucleic acids are discussed, for example, in Beaucage & Caruthers, *Tetra. Letts.* 22: 1859-62 (1981), and Matteucci & Caruthers, *J. Am. Chem. Soc.* 103: 3185 (1981).

Restriction enzyme digestions, phosphorylations, ligations, and transformations were done as described in Sambrook et al., MOLECULAR CLONING: A LABORATORY MANUAL, 2nd ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. It is therefore understood that modifications in the DNA sequences encoding A622 and NBB1, respectively, which do not substantially affect the functional properties of either enzyme are contemplated.

I. Increasing Nicotinic Alkaloids in *Nicotiana* by Overexpressing at Least One of A622 and NBB1

Although A622 and NBB1 were previously identified, before the present invention the field was wholly unaware that overexpressing at least one of A622 or NBB1 in a *Nicotiana* plant increases nicotinic alkaloid content. Accordingly, the present invention encompasses both methodology and constructs for increasing nicotinic alkaloid content in a *Nicotiana* plant, by overexpressing at least one of A622 or NBB1. Overexpressing both A622 and NBB1 further increases nicotinic alkaloids levels in a *Nicotiana* plant.

In the present description, an "alkaloid" is a nitrogen-containing basic compound found in plants and produced by secondary metabolism. A "nicotinic alkaloid" is nicotine or an alkaloid that is structurally related to nicotine. In the case of tobacco, nicotinic alkaloid content and total alkaloid content are used synonymously.

Illustrative major *Nicotiana* nicotinic alkaloids include but are not limited to nicotine, nornicotine, anatabine, and anabasine. Illustrative minor *Nicotiana* alkaloids include but are not limited to anatalline, N-methylanatabine, N-methylanabasine, myosmine, anabaseine, N'-formylnornicotine, nicotyrine, and cotinine. Other minor nicotinic alkaloids in tobacco are reported, for example, in Hecht, S. S. et al., *Accounts of Chemical Research* 12: 92-98 (1979); Tso, T. C., PRODUCTION, PHYSIOLOGY AND BIOCHEMISTRY OF TOBACCO PLANT, Ideals Inc. (Beltsville, Md.), 1990.

Many other pyridyl bases plus many derivatives of nornicotine, anatabine, and anabasine are nicotinic alkaloids that have been reported to be present in tobacco and for purposes of the invention shall be included within minor *Nicotiana* alkaloids. Most of these so-called minor nicotinic alkaloids are present in less than 50 µg/g (dry weight basis) and many others are present in nanogram amounts. Bush, L. P., et al., "Biosynthesis and metabolism in nicotine and related alkaloids" in NICOTINE AND RELATED ALKALOIDS, J. W. Gorrod & J. Wahren (eds.) Chapman & Hall, London (1993); Bush, L. P., et al., "Alkaloid Biosynthesis" in TOBACCO PRODUCTION, CHEMISTRY AND TECHNOLOGY, D. L. Davis and M. T. Nielson (eds.) Coresta, 1999. The chemical structures of several nicotinic alkaloids are presented, for example, in Felpin et al., *J. Org. Chem.* 66: 6305-312 (2001).

Nicotine is the primary alkaloid in *N. tabacum*, as in 50 to 60 percent of other of *Nicotiana* species. Depending on the variety, about 85 to about 95 percent of total alkaloids in *N. tabacum* is nicotine. Bush et al. (1999), supra; Hoffmann et al., *Journal of Toxicology and Environmental Health* 41: 1-52 (1994). Based on alkaloid accumulation in the leaves, nornicotine, anatabine, and anabasine are the other foremost alkaloids in *N. tabacum*. Anatabine is usually not the primary alkaloid in any *Nicotiana* species but does accumulate to relatively higher amounts in three species; anabasine is the primary alkaloid in four species. Nornicotine is the primary alkaloid in 30 to 40 percent of *Nicotiana* species.

In this description, "expression" denotes the production of the protein product encoded by a nucleotide sequence. "Overexpression" refers to the production of a protein product in a transgenic organism that exceeds levels of production in a normal or non-genetically engineered organism. As in conventional in the art, nucleotide sequences are denoted by italicized font (e.g. *PMT*), whereas polypeptide sequences are not italicized (e.g. PMT)

A622

It has been reported that A622 exhibits the same expression pattern as PMT. Shoji et al., *Plant Cell Physiol.* 41: 1072-76 (2000a), and *Plant Mol. Biol.* 50: 427-40 (2002). Both A622 and PMT are expressed specifically in roots, particularly in the cortex and endodermis of the apical parts of the roots and root hairs. Moreover, A622 and PMT have a common pattern of expression in response to NIC regulation and methyl-jasmonate stimulus. A622 is induced in the roots of *Nicotiana tabacum* in response to wounding of aerial tissues. Cane et al., *Func. Plant Biol.* 32: 305-20 (2005). In *N. glauca*, A622 is induced in wounded leaves under conditions that result in QPT induction. Sinclair et al., *Func. Plant Biol.* 31: 721-29 (2004).

NIC1 and NIC2 loci are two independent genetic loci in *N. tabacum*, formerly designated as A and B. Mutations nic1 and nic2 reduce expression levels of nicotine biosynthesis enzymes and nicotine content, generally the nicotine content of wild type>homozygous nic2>homozygous nic1>homozygous nic1 and homozygous nic2 plants. Legg & Collins, *Can. J. Cyto.* 13: 287 (1971); Hibi et al., *Plant Cell* 6: 723-35 (1994); Reed & Jelesko, *Plant Science* 167: 1123 (2004). In this description, "nic1nic2" denotes tobacco genotypes that are homozygous for both the nic1 and the nic2 mutations.

The nucleic acid sequence of A662 (SEQ ID NO: 3) has been determined. Hibi et al. (1994), supra. The protein A622 (SEQ ID NO: 4), encoded by this nucleic acid sequence, resembles isoflavone reductases (IFR) and contains an NADPH-binding motif. A622 shows homology to TP7, a tobacco phenylcoumaran benzylic ether reductase (PCBER) involved in lignin biosynthesis. Shoji et al. (2002), supra. No PCBER activity was observed, however, when A622 expressed in *E. coli* was assayed with two different substrates.

Based on co-regulation of A622 and PMT and the similarity of A622 to IFR, A622 was proposed to function as a reductase in the final steps of nicotinic alkaloid synthesis. Hibi et al. (1994); Shoji, et al. (2000a). No IFR activity was observed, however, when the protein was expressed in bacteria (id.). Heretofore there was no understanding that overexpressing A622 increases nicotine levels.

"A622 expression" refers to biosynthesis of a gene product encoded by SEQ ID NO: 3. "A622 overexpression" denotes an increasing of A622 expression. A622 overexpression affects an increase in nicotinic alkaloid content for a plant or cell in which the overexpression occurs. A622 overexpression includes the biosynthesis of a gene product encoded by the following: full-length A622 nucleic acid sequence disclosed in Hibi et al. (1994), supra (SEQ ID NO: 3), SEQ ID NO: 3B, and all A622 polynucleotide variants.

NBB1

The NBB1 sequence was identified as a cDNA prepared from a *Nicotiana sylvestris*-derived cDNA library, pursuant to the protocol of Katoh et al., *Proc. Japan Acad.* 79 (Ser. B): 151-54 (2003). Like A622, NBB1 is controlled by the nicotine biosynthesis regulatory loci, NIC1 and NIC2. NBB1 and PMT have the same pattern of expression in tobacco plants. That NBB1 is involved in nicotine biosynthesis is indicated by the fact that NBB1, like PMT and A622, is under the control of the NIC genes and exhibits a similar pattern of expression.

The nucleic acid sequence of NBB1 (SEQ ID NO: 1) has been determined and encodes the polypeptide sequence set forth in SEQ ID NO: 2. "NBB1 expression" refers to biosynthesis of a gene product encoded by SEQ ID NO: 1. "NBB1 overexpression" denotes an increasing of NBB1 expression. NBB1 overexpression affects an increase in nicotinic alkaloid content for a plant or cell in which the overexpression occurs. NBB1 overexpression includes biosynthesis of a gene product encoded by the following: SEQ ID NO: 1, SEQ ID NO: 1B, and all NBB1 polynucleotide variants.

II. Increasing Nicotinic Alkaloids in *N. tabacum* by Overexpressing PMT

The only previous report demonstrating overexpression of a nicotinic biosynthesis gene in any *Nicotiana* species was in *N. sylvestris*, where PMT overexpression resulted in a modest 40% increase in leaf nicotine. Sato et al., *Proc. Nat'l Acad. Sci. USA* 98: 367-72 (2001). While overexpressing a nicotinic alkaloid biosynthesis gene in one plant species, such as *N. sylvestris*, results in an increased accumulation of secondary metabolites, it does not necessarily follow that similar accumulation of secondary metabolites will occur in a related species, such as *N. tabacum*. Saitoh et al., *Phytochemistry* 24: 477-80 (1985). This is especially relevant for PMT overexpression, since *N. tabacum* contains five expressed PMT genes and *N. sylvestris* contains three expressed PMT genes. Hashimoto et al., *Plant Mol. Biol.* 37: 25-37 (1998); Reichers & Timko, *Plant Mol. Biol.* 41: 387-401 (1999). Indeed, when the PMT gene from *N. tabacum* was overexpressed in *Duboisia* hairy root cultures, the levels of nicotine, hyoscyamine, and scopolamine did not increase significantly. Moyano et al., *Phytochemistry* 59, 697-702 (2002). Likewise, overexpressing the same PMT gene in transgenic plants and hairy root cultures of *Atropa belladonna* did not affect hyoscyamine and scopolamine levels. Sato et al., *Proc. Nat'l Acad. Sci. USA* 98: 367-72 (2001); Rothe et al., *J. Exp. Bot.* 54: 2065-070 (2003).

In *Solanaceous* species, such as tobacco, it seems that the same alkaloid biosynthesis pathway in two related plant species can be differently regulated and overexpression of a given gene does not necessarily lead to a similar accumulation pattern of secondary metabolites. Moyano et al., *J. Exp. Bot.* 54: 203-11 (2003). For example, when sixty *Nicotiana* species were analyzed, there was considerable variation in total alkaloid content and alkaloid profile amongst the species. Saitoh et al., *Phytochemistry* 24: 477-80 (1985). For instance, while *N. sylvestris* had the highest dry weight content of total alkaloids (the sum of nicotine, nornicotine, anabasine and anatabine) at 29,600 μg/g or 2.96 percent, *N. alata* contained the lowest at 20 μg/g or 0.002 percent. The ratio of nicotine to total alkaloid in the leaves of *N. sylvestris* was about 80 percent versus about 95 percent for *N. tabacum* L. Id. Also, the ratio of nornicotine to total alkaloid in *N. sylvestris* leaves was 19.1 percent versus 3 percent for *N. tabacum* L. Id. Based on these large variations among the sixty *Nicotiana* species, Saitoh et al. conclude, "The amount and ratio of total and individual alkaloids present in a plant depend on the species. No clear-cut correlation between alkaloid pattern and classification of the genus *Nicotiana* seems to exist." Id. at page 477.

Accordingly, the instant invention provides methodology and constructs for increasing nicotinic alkaloids in *N. tabacum* by overexpressing PMT.

The nucleic acid sequence of PMT (SEQ ID NO: 7) has been determined and encodes the polypeptide sequence set forth in SEQ ID NO: 8. "PMT expression" refers to biosynthesis of a gene product encoded by SEQ ID NO: 7. "PMT overexpression" denotes an increasing of PMT expression. PMT overexpression affects an increase in nicotinic alkaloid content for a plant or cell in which the overexpression occurs. PMT overexpression includes the biosynthesis of a gene product encoded by the following: full-length PMT nucleic acid sequence disclosed in Hibi et al. (1994), supra (SEQ ID NO: 7), SEQ ID NO: 7B, and all PMT polynucleotide variants.

III. Increasing Nicotinic Alkaloids in *Nicotiana* by Overexpressing QPT and PMT Until now there was no knowledge that overexpressing QPT and PMT synergistically increases nicotinic alkaloids. That is, further increases in nicotine levels can be achieved by overexpressing QPT and PMT, as compared with overexpressing QPT or PMT alone. Pursuant to this aspect of the invention, a nucleic acid construct comprising both QPT and PMT is introduced into a *Nicotiana* plant cell.

The nucleic acid sequence of QPT (SEQ ID NO: 5) has been determined and encodes the polypeptide sequence set forth in SEQ ID NO: 6. "QPT expression" refers to biosynthesis of a gene product encoded by SEQ ID NO: 5. "QPT overexpression" denotes an increasing of QPT expression. QPT overexpression affects an increase in nicotinic alkaloid content for a plant or cell in which the overexpression occurs. QPT overexpression includes the biosynthesis of a gene product encoded by the following: full-length QPT nucleic acid sequence disclosed in U.S. Pat. No. 6,423,520 (SEQ ID NO: 5), SEQ ID NO: 5B, and all QPT polynucleotide variants.

IV. Increasing Nicotinic Alkaloids in *Nicotiana* by Overexpressing at Least Two or More of A622, NBB1, QPT, and PMT While it is well-recognized that QPT plays a role in nicotine biosynthesis, see WO 98/56923, the present invention contemplates further increases in nicotine synthesis by overexpressing at least two or more of A622, NBB1, QPT, and PMT in *Nicotiana*. Pursuant to this aspect of the invention, a nucleic acid construct comprising at least two of A622, NBB1, QPT, and PMT is introduced into a *Nicotiana* plant cell. An illustrative nucleic acid construct may comprise both QPT and A622.

V. Increasing *Nicotiana* Nicotinic Alkaloids and Yield

Increased nicotine plants of the invention may be produced by conventional breeding or crossing, as described by Wernsman et al., in 2 PRINCIPLES OF CULTIVAR DEVELOPMENT: CROP SPECIES (Macmillan 1997). For example, a stable genetically engineered transformant, regenerated from tobacco material that contains a suitable transgene, is employed to introgress a high-nicotine trait into a desirable commercially acceptable genetic background, thereby obtaining a tobacco cultivar or variety that combines a high nicotine level with said desirable background.

Similarly, for example, a genetically engineered plant overexpressing QPT and A622 may be produced by crossing a transgenic plant overexpressing QPT with a transgenic plant overexpressing A622. Following successive rounds of crossing and selection, a genetically engineered plant having overexpressing QPT and A622 can be selected.

While any desirable gene can be introgressed into a high-nicotine variety, there is a critical need for introducing a high nicotine trait into a high-yielding tobacco background. Several studies indicate that "Yield improvements have been hampered by the negative relationship that exists with nicotine concentration." PRODUCTION, CHEMISTRY AND TECHNOLOGY, D. L. Davis and M. T. Nielson (eds.) Coresta at page 46 (1999). In his reflections of tobacco breeding, Dr. Earl Wernsman asserts "continued selection for yield alone will soon result in a population whose nicotine concentration in cured leaf is so low that the tobaccos are unacceptable to industry" Wernsman, *Recent Advances in Tobacco Science* 25: 5-35 (1999). He postulates that "genetic methods of up-regulating nicotine synthesis may be needed to permit additional increases in yielding ability while maintaining nicotine concentration" Id.

Accordingly, the present invention provides a means for correcting the "negative correlation" between yield and nicotine content in *Nicotiana* plants by overexpressing a gene encoding a nicotine biosynthesis enzyme in a high-yielding *Nicotiana* plant. Exemplary nicotine biosynthesis enzymes include but are not limited to QPTase, PMTase, A622, NBB1, arginine decarboxylase (ADC), methylputrescine oxidase (MPO), NADH dehydrogenase, ornithine decarboxylase (ODC), and S-adenosyl-methionine synthetase (SAMS). Increased-nicotine plants resulting there from are then crossed with any desirable commercially acceptable genetic background that maintains high yield. Suitable high-yield *Nicotiana* plants include but are not limited to *Nicotiana tabacum* cultivars K 326, NC71, NC72 and RG81. Following successive rounds of crossing and selection, a genetically engineered plant having increased nicotine and increased yield is accordingly produced.

A further aspect of the invention provides crossing an increased-nicotine plant with an increased-yield plant as another strategy for breaking the negative correlation between nicotine content and yield.

"Increased yield genes" encompass any gene whose expression correlates with increased production capacity as reflected by, for example, increased photoassimilate production, increased growth rate, improved vigor, enhanced yield, enhanced $CO_2$ fixation, enhanced biomass, increased seed production, improved storage, enhanced yield, increased disease tolerance, increased insect tolerance, increased water-stress tolerance, enhanced sweetness, improved starch composition, improved sucrose accumulation and export, and improved response to oxidative stress compared with a wild-type control plant.

Likewise, an "increased yield plant" refers to a plant, or any portion thereof, overexpressing an "increased yield gene" and exhibits increased production capacity as reflected by, for example, increased photoassimilate production, increased growth rate, improved vigor, enhanced yield, enhanced $CO_2$ fixation, enhanced biomass, increased seed production, improved storage, enhanced yield, increased disease tolerance, increased insect tolerance, increased water-stress tolerance, enhanced sweetness, improved starch composition, improved sucrose accumulation and export, and improved response to oxidative stress compared with a wild-type control plant.

For example, and in no way limiting the invention, an increased yield plant can be produced by overexpressing a pathogenesis-related (PR) gene. It has been shown that overexpressing a maize PRms gene, in tobacco produced transgenic tobacco plants having enhanced biomass and seed production. Murillo et al., *Plant J.* 36: 330-41 (2003). Likewise, an increased yield plant can be produced by overexpressing a gene encoding a Calvin cycle enzyme. Tamoi et al. *Plant Cell Physiol.* 47(3)380-390 (2006).

Tobacco plants overexpressing, for example, a cyanobacterial fructose-1,6-/sedoheptulose-1,7-bisphosphatase displayed enhanced photosynthetic efficiency and growth efficiency compared with wild-type tobacco. Miyagawa et al., *Nature Biotech.* 19: 965-69 (2001).

The present invention also contemplates producing a plant having increased yield and increased nicotine by overexpressing a gene encoding a nicotine biosynthesis enzyme, such as QPT, PMT, A622, or NBB1, and overexpressing an increased yield gene, such as PRms, fructose-1,6-/sedoheptulose-1,7-bisphosphatase, fructose-1,6-bisphosphatase, and sedoheptulose-1,7-bisphosphatase, sedoheptulose-1,7-bisphosphatase in the same plant or cell.

VI. Producing Nicotinic Alkaloids and Related Compounds in Non-Nicotine Producing Cells A622 and NBB1 can be introduced into a non-nicotine producing plant or cell, thereby producing nicotine or related compounds in an organism or cell that does not produce these compounds otherwise. A variety of products can be produced from these engineered organisms and cells, including nicotine, nicotine analogs, and nicotine biosynthesis enzymes.

A "non-nicotine producing plant" refers to any plant that does not produce nicotine or related nicotinic alkaloids. Illustrative non-nicotine producing plants include but are not limited to *Atropa belladonna* and *Arabidopsis thaliana*.

"Non-nicotine producing cells" refers to cells from any organism that does not produce nicotine or related nicotinic alkaloids. Illustrative cells include but are not limited to plant cells, such as *Atropa belladonna*, *Arabidopsis thaliana*, as well as insect, mammalian, yeast, fungal, algal, or bacterial cells.

A "nicotine analog" has the basic structure of nicotine but may, for example, have different ring substituents. For example, a nicotine analog may substitute a hydrogen (—H) for the methyl group (—$CH_3$) thereby producing nornicotine, which is an analog of nicotine. In addition to sharing a similar structure with nicotine, nicotine analogs may provide similar physiological effects. Cotinine, for example, has been cited for its positive effects on improving concentration and memory and, accordingly, is a nicotine analog. Accordingly, nicotine analogs are defined broadly to cover any and all compounds having similar structural and functional activity to nicotine.

VII. Synthesis of Compounds Using Novel Enzymes

Recently, there has been great interest in synthesizing nicotine analogs that target nicotine receptors and provide therapeutic effects for neurogenerative diseases and cognitive disabilities. For example, Targacept, a pharmaceutical company formed as a spinout from R. J. Reynolds Tobacco Company, endeavors to develop and commercialize nicotine analog drugs based on selective activation of neuronal nicotinic acetylcholine receptors (NNRs). Because the present invention provides a novel nicotine biosynthesis enzyme, there may be value in using NBB1 alone, or NBB1 and A622, for developing novel nicotine analogs. For example, using the inventive methods and constructs, a nicotinic alkaloid analog can be produced by providing a nicotine analog precursor in a cell culture system.

Additionally, the inventive enzymes may be used for in vitro synthesis of nicotine and related compounds. That is, recombinant A622 and NBB1 can be used for the synthesis or partial synthesis of a nicotinic alkaloid and a nicotinic alkaloid analog.

Nicotinic Alkaloid Biosynthesis Sequences

Nicotinic alkaloid biosynthesis genes have been identified in several plant species, exemplified by *Nicotiana* plants. Accordingly, the present invention embraces any nucleic acid, gene, polynucleotide, DNA, RNA, mRNA, or cDNA molecule that is isolated from the genome of a plant species, or produced synthetically, that increases *Nicotiana* nicotinic alkaloid biosynthesis. Additionally, expression of such nicotinic alkaloid biosynthesis sequence produces nicotinic alkaloids in a non-nicotine producing cell, such as an insect cell. The DNA or RNA may be double-stranded or single-stranded. Single-stranded DNA may be the coding strand, also known as the sense strand, or it may be the non-coding strand, also called the anti-sense strand.

It is understood that NBB1, A622, QPT, and PMT include the sequences set forth in SEQ ID NO: 1, 1B, 3, 3B, 5, 5B, 7, and 7B, respectively, as well as nucleic acid molecules comprised of variants of SEQ ID NO: 1, 1B, 3, 3B, 5, 5B, 7, and 7B, with one or more bases deleted, substituted, inserted, or added, which variant codes for a polypeptide with nicotinic alkaloid biosynthesis activity. Accordingly, sequences having "base sequences with one or more bases deleted, substituted, inserted, or added" retain physiological activity even when the encoded amino acid sequence has one or more amino acids substituted, deleted, inserted, or added. Additionally, multiple forms of A622, NBB1, QPTase, and PMTase may exist, which may be due to post-translational modification of a gene product, or to multiple forms of the respective PMT, QPT, A622, or NBB1 genes. Nucleotide sequences that have such modifications and that code for a nicotinic alkaloid biosynthesis enzyme are included within the scope of the present invention.

For example, the poly A tail or 5'- or 3'-end, nontranslation regions may be deleted, and bases may be deleted to the extent that amino acids are deleted. Bases may also be substituted, as long as no frame shift results. Bases also may be "added" to the extent that amino acids are added. It is essential, however, that any such modification does not result in the loss of nicotinic alkaloid biosynthesis enzyme activity. A modified DNA in this context can be obtained by modifying the DNA base sequences of the invention so that amino acids at specific sites are substituted, deleted, inserted, or added by site-specific mutagenesis, for example. Zoller & Smith, *Nucleic Acid Res.* 10: 6487-500 (1982).

A nicotinic alkaloid biosynthesis sequence can be synthesized ab initio from the appropriate bases, for example, by using an appropriate protein sequence disclosed herein as a guide to create a DNA molecule that, though different from the native DNA sequence, results in the production of a protein with the same or similar amino acid sequence. This type of synthetic DNA molecule is useful when introducing a DNA sequence into a non-plant cell, coding for a heterologous protein, that reflects different (non-plant) codon usage frequencies and, if used unmodified, can result in inefficient translation by the host cell.

By "isolated" nucleic acid molecule(s) is intended a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules, according to the present invention, further include such molecules produced synthetically.

"Exogenous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

In contrast, "endogenous nucleic acid" refers to a nucleic acid, gene, polynucleotide, DNA, RNA, mRNA, or cDNA molecule that is present in the genome of a plant or organism that is to be genetically engineered. An endogenous sequence is "native" to, i.e., indigenous to, the plant or organism that is to be genetically engineered.

"Heterologous nucleic acid" refers to a nucleic acid, DNA or RNA, which has been introduced into a cell (or the cell's ancestor) which is not a copy of a sequence naturally found in the cell into which it is introduced. Such heterologous nucleic acid may comprise segments that are a copy of a sequence which is naturally found in the cell into which it has been introduced, or fragments thereof.

A "chimeric nucleic acid" comprises a coding sequence or fragment thereof linked to a transcription initiation region that is different from the transcription initiation region with which it is associated in cells in which the coding sequence occurs naturally.

Unless otherwise indicated, all nucleotide sequences determined by sequencing a DNA molecule herein were determined using an automated DNA sequencer, such as the Model 373 from Applied Biosystems, Inc. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

For the purpose of the invention, two sequences hybridize when they form a double-stranded complex in a hybridization solution of 6×SSC, 0.5% SDS, 5×Denhardt's solution and 100 µg of non-specific carrier DNA. See Ausubel et al., supra, at section 2.9, supplement 27 (1994). Sequences may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

The present application is directed to such nucleic acid molecules which are at least 60%, 65%, 70%, 75%, 80%, 85%, 90%, 95%, 96%, 97%, 98%, 99% or 100% identical to a nucleic acid sequence described in any of SEQ ID NO: 1, 1B, 3, 3B, 5, 5B, 7, and 7B. Preferred are nucleic acid molecules which are at least 95%, 96%, 97%, 98%, 99% or 100% identical to the nucleic acid sequence shown in any of SEQ ID NO: 1, 1B, 3, 3B, 5, 5B, 7, and 7B. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art and can be determined conventionally using publicly available computer programs such as the BLASTN algorithm. See Altschul et al., *Nucleic Acids Res.* 25: 3389-402 (1997).

The present invention further provides nucleic acid molecules comprising the nucleotide sequence of SEQ ID NOs.: 1, 1B, 3, 3B, 5, 5B, 7, and 7B, respectively, which encode an active nicotine biosynthesis enzyme, wherein the enzyme has amino acid sequence that corresponds to SEQ ID NO.: 2, 4, 6, and 8, respectively, and wherein the protein of the invention encompasses amino acid substitutions, additions and deletions that do not alter the function of the nicotine biosynthesis enzyme.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene" such as those described in Maxygen-assigned patents.

Nucleic Acid Constructs

In accordance with one aspect of the invention, a sequence that increases nicotinic alkaloid biosynthesis is incorporated into a nucleic acid construct that is suitable for plant or cell transformation. Thus, such a nucleic acid construct can be used to overexpress at least one of A622, NBB1, PMT, and QPT in a plant, as well as express A622 and NBB1, for example, in a non-nicotine producing cell.

Recombinant nucleic acid constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence then is cloned into a vector containing suitable regulatory elements, such as upstream promoter and downstream terminator sequences.

An important aspect of the present invention is the use of nucleic acid constructs wherein a nicotinic alkaloid biosynthesis-encoding sequence is operably linked to one or more regulatory sequences, which drive expression of the nicotinic alkaloid biosynthesis-encoding sequence in certain cell types, organs, or tissues without unduly affecting normal development or physiology.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell to increase expression of A622, NBB1, PMTase, or QPTase may be constitutive promoters, such as the cauliflower mosaic virus (CaMV) 35S promoter, or tissue-specific, tissue-preferred, cell type-specific, and inducible promoters. Preferred promoters include promoters which are active in root tissues, such as the tobacco RB7promoter (Hsu et al. *Pestic. Sci.* 44: 9-19 (1995); U.S. Pat. No. 5,459,252), maize promoter CRWAQ81 (US published patent application 20050097633); the *Arabidopsis* ARSK1 promoter (Hwang and Goodman, *Plant J* 8:37-43 (1995)), the maize MR7 promoter (U.S. Pat. No. 5,837,848), the maize ZRP2 promoter (U.S. Pat. No. 5,633,363), the maize MTL promoter (U.S. Pat. Nos. 5,466,785 and 6,018,099) the maize MRS1, MRS2, MRS3, and MRS4 promoters (U.S. Pat. App. 20050010974), an *Arabidopsis* cryptic promoter (U.S. Pat. App. 20030106105) and promoters that are activated under conditions that result in elevated expression of enzymes involved in nicotine biosynthesis such as the tobacco RD2 promoter (U.S. Pat. No. 5,837,876), PMT promoters (Shoji T. et al., *Plant Cell Physiol.* 41: 831-39 (2000b); WO 2002/038588) or an A622 promoter (Shoji T. et al., *Plant Mol Biol.* 50: 427-40 (2002)).

The vectors of the invention may also contain termination sequences, which are positioned downstream of the nucleic acid molecules of the invention, such that transcription of mRNA is terminated, and polyA sequences added. Exemplary of such terminators are the cauliflower mosaic virus (CaMV) 35S terminator and the nopaline synthase gene (Tnos) terminator. The expression vector also may contain enhancers, start codons, splicing signal sequences, and targeting sequences.

Expression vectors of the invention may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidne kinase, xanthine-guanine phospho-ribosyltransferase, glyphosate and glufosinate resistance, and amino-glycoside 3'-O-phosphotranserase (kanamycin, neomycin and G418 resistance). These markers may include resistance to G418, hygromycin, bleomycin, kanamycin, and gentamicin. The construct may also contain the selectable marker gene Bar that confers resistance to herbicidal phosphinothricin analogs like ammonium gluphosinate. Thompson et al., *EMBO J.* 9: 2519-23 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

Plants for Genetic Engineering

The present invention comprehends the genetic manipulation of a *Nicotiana* plant for increasing nicotinic alkaloid synthesis via introducing a polynucleotide sequence that encodes an enzyme in the pathway for nicotinic alkaloid synthesis. Additionally, the invention provides methods for producing nicotinic alkaloids and related compounds in non-nicotine producing plants, such as *Arabidopsis thaliana* and *Atropa belladonna*.

"Genetically engineered" (GE) encompasses any methodology for introducing a nucleic acid or specific mutation into a host organism. For example, a tobacco plant is genetically engineered when it is transformed with a polynucleotide sequence that increases expression of a gene, such as A622 or NBB1, and thereby increases nicotine levels. In contrast, a tobacco plant that is not transformed with a polynucleotide sequence is a control plant and is referred to as a "non-transformed" plant.

In the present context, the "genetically engineered" category includes "transgenic" plants and cells (see definition, infra), as well as plants and cells produced by means of targeted mutagenesis effected, for example, through the use of chimeric RNA/DNA oligonucleotides, as described by Beetham et al., *Proc. Nat'l. Acad. Sci. USA* 96: 8774-8778 (1999) and Zhu et al., loc. cit. at 8768-8773, or so-called "recombinagenic olionucleobases," as described in PCT application WO 03/013226. Likewise, a genetically engineered plant or cell may be produced by the introduction of a modified virus, which, in turn, causes a genetic modification in the host, with results similar to those produced in a transgenic plant, as described herein. See, e.g., U.S. Pat. No. 4,407,956. Additionally, a genetically engineered plant or cell may be the product of any native approach (i.e., involving no foreign nucleotide sequences), implemented by introducing only nucleic acid sequences derived from the host species or from a sexually compatible species. See, e.g., U.S. published application No. 2004/0107455.

"Plant" is a term that encompasses whole plants, plant organs (e.g. leaves, stems, roots, etc.), seeds, differentiated or undifferentiated plant cells, and progeny of the same.

Plant material includes, without limitation, seeds suspension cultures, embryos, meristematic regions, callus tissues, leaves, roots, shoots, stems, fruit, gametophytes, sporophytes, pollen, and microspores. The class of plants which can be used in the present invention is generally as broad as the class of higher plants amenable to genetic engineering techniques, including both monocotyledonous and dicotyledonous plants, as well as gymnosperms. A preferred nicotine-producing plant includes *Nicotiana, Duboisia, Anthocericis* and *Salpiglessis* genera in the *Solanaceae* or the *Eclipta* and *Zinnia* genera in the *Compositae*.

"Tobacco" refers to any plant in the *Nicotiana* genus that produces nicotinic alkaloids. Tobacco also refers to products comprising material produced by a *Nicotiana* plant, and therefore includes, for example, expanded tobacco, reconstituted tobacco, cigarettes, cigars, chewing tobacco or forms of smokeless tobacco, snuff and snus made from GE increased-nicotine tobacco. Examples of *Nicotiana* species include but are not limited to the following: *Nicotiana acaulis, Nicotiana acuminata, Nicotiana acuminata* var. *multiflora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana hybrid, Nicotiana ingulba, Nicotiana kawakamii, Nicotiana knightiana, Nicotiana langsdorffii, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *hesperis, Nicotiana otophora, Nicotiana paniculata, Nicotiana pauciflora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *ingulba, Nicotiana rotundifolia, Nicotiana rustica, Nicotiana setchellii, Nicotiana simulans, Nicotiana solanifolia, Nicotiana spegazzinii, Nicotiana stocktonii, Nicotiana suaveolens, Nicotiana sylvestris, N. tabacum, Nicotiana thyrsiflora, Nicotiana tomentosa, Nicotiana tomentosiformis, Nicotiana trigonophylla, Nicotiana umbratica, Nicotiana undulata, Nicotiana velutina, Nicotiana wigandioides*, and *Nicotianaxsanderae*.

In the present description, "tobacco hairy roots" refers to tobacco roots that have T-DNA from an Ri plasmid of *Agrobacterium rhizogenes* integrated in the genome and grow in culture without supplementation of auxin and other phytohormones. Tobacco hairy roots produce nicotinic alkaloids as roots of a tobacco plant do. These types of roots are characterized by fast growth, frequent branching, plagiotropism, and the ability to synthesize the same compounds as the roots of the intact plant. David et al., *Biotechnology* 2: 73-76.(1984). Roots of *Solanaceae* plants are the main site of tropane alkaloid biosynthesis, and hence hairy root cultures also are capable of accumulating high levels of these metabolites. For example, see Oksman-Caldentey & Arroo, "Regulation of tropane alkaloid metabolism in plants and plant cell cultures," in METABOLIC ENGINEERING OF PLANT SECONDARY METABOLISM 253-81 (Kluwer Academic Publishers, 2000).

Non-Nicotine Producing Cells for Genetic Engineering

The invention contemplates genetically engineering "non-nicotine producing cells" with a nucleic acid sequence encoding an enzyme involved in the production of nicotinic alkaloids. Non-nicotine producing cells refer to a cell from any organism that does not produce nicotine. Illustrative cells include but are not limited to plant cells, such as *Atropa belladonna, Arabidopsis thaliana*, as well as insect, mammalian, yeast, fungal, algal, or bacterial cells. Suitable host cells are discussed further in Goeddel, GENE EXPRESSION TECHNOLOGY: METHODS IN ENZYMOLOGY 185, Academic Press, San Diego, Calif. (1990).

"Insect cell" refers to any insect cell that can be transformed with a gene encoding a nicotine biosynthesis enzyme and is capable of expressing in recoverable amounts the enzyme or its products. Illustrative insect cells include Sf9 cells (ATCC CRL 1711).

"Fungal cell" refers to any fungal cell that can be transformed with a gene encoding a nicotine biosynthesis enzyme and is capable of expressing in recoverable amounts the enzyme or its products. Illustrative fungal cells include yeast cells such as *Saccharomyces cerivisae* (Baldari, et al., 1987. EMBO J. 6: 229-234) and *Pichia pastoris* (e.g. *P. pastoris* KM714 available from Invitrogen). Cells of filamentous fungi such as *Aspergillus* and *Trichoderma* may also be used. Archer, et al., *Antonie van Leeuwenhoek* 65: 245-250 (2004).

"Bacterial cell" refers to any bacterial cell that can be transformed with a gene encoding a nicotinic alkaloid biosynthesis enzyme and is capable of expressing in recoverable amounts the enzyme or its products. Illustrative bacterial cells include *E. coli*, such as *E. coli* strain M15/rep4, which is available commercially from QIAGEN.

"Mammalian cell" refers to any mammalian cell that can be transformed with a gene encoding a nicotine biosynthesis enzyme and is capable of expressing in recoverable amounts the enzyme or its products. Illustrative mammalian cells include Chinese hamster ovary cells (CHO) or COS cells. Mammalian cells may also include a fertilized oocyte or an embryonic stem cell into which nicotinic alkaloid biosynthesis enzyme-coding sequences have been introduced. Such host cells can then be used to create non-human transgenic animals. Examples of systems for regulated expression of proteins in mammalian cells include Clontech's Tet-Off and Tet-On gene expression systems and similar systems. Gossen and Bujard, *Proc. Natl. Acad. Sci. USA* 89: 55475551 (1992).

"Algae cell" refers to any algae species that can be transformed with a gene encoding a nicotine biosynthesis enzyme without adversely affecting normal algae development or physiology. Illustrative algae cells include *Chlamydomonas reinhardtii* (Mayfield and Franklin, *Vaccine* 23: 1828-1832 (2005).

Because production of nicotinic alkaloids in an insect cell could adversely affect insect growth and development, an inducible expression system may mitigate adverse affects. For example, insect cells may be first grown under non-inducing conditions to a desired state and then expression of the enzyme is induced.

Additionally, cells expressing nicotinic alkaloid biosynthesis genes may be supplied with precursors to increase substrate availability for nicotinic alkaloid synthesis. Cells may be supplied with analogs of precursors which may be incorporated into analogs of naturally occurring nicotinic alkaloids.

Transformation and Selection

While nicotine is the major alkaloid in *N. tabacum* and some other species in the *Nicotiana* genus, other plants have nicotine-producing ability, including, for example, *Duboisia, Anthocericis* and *Salpiglessis* genera in the *Solanaceae*, and *Eclipta* and *Zinnia* genera in the *Compositae*. Using the inventive constructs and methods, nicotine may be produced in non-nicotine producing plants, such as *Atropa belladonna* and *Arabidopsis thaliana*, and cells, such as insect, fungal, and bacterial cells.

For the purposes of this description, a plant or non-nicotine producing cell, such as a fungal cell, may be transformed with a plasmid comprising one or more sequences, each operably linked to a promoter. For example, an illustrative vector may comprise a QPT sequence operably linked to a promoter. Likewise, the plasmid may comprise a QPT sequence operably linked to a promoter and an A622 sequence operably linked to a promoter. Alternatively, a plant or non-nicotine producing cell may be transformed with more than one plasmid. For example, a plant or non-nicotine producing cell may be transformed with a first plasmid comprising a QPT sequence operably linked to a promoter, which is distinct from a second plasmid comprising an A622 or NBB1 sequence. Of course, the first and second plasmids or portions thereof are introduced into the same cell.

Plant Transformation

"Transgenic plant" refers to a plant that comprises a nucleic acid sequence that also is present per se in another organism or species or that is optimized, relative to host codon usage, from another organism or species. Both monocotyledonous and dicotyledonous angiosperm or gymnosperm plant cells may be transformed in various ways known to the art. For example, see Klein et al., *Biotechnology* 4: 583-590 (1993); Bechtold et al., *C. R. Acad. Sci. Paris* 316:1194-1199 (1993); Bent et al., *Mol. Gen. Genet.* 204: 383-396 (1986); Paszowski et al., *EMBO J.* 3: 2717-2722 (1984); Sagi et al., *Plant Cell Rep.* 13: 262-266 (1994). *Agrobacterium* species such as *A. tumefaciens* and *A. rhizogenes* can be used, for example, in accordance with Nagel et al., *Microbiol Lett* 67: 325 (1990). Additionally, plants may be transformed by *Rhizobium, Sinorhizobium* or *Mesorhizobium* transformation. Broothaerts et al., *Nature* 433:629-633 (2005).

For example, *Agrobacterium* may be transformed with a plant expression vector via, e.g., electroporation, after which the *Agrobacterium* is introduced to plant cells via, e.g., the well known leaf-disk method. Additional methods for accomplishing this include, but are not limited to, electroporation, particle gun bombardment, calcium phosphate precipitation, and polyethylene glycol fusion, transfer into germinating pollen grains, direct transformation (Lorz et al., *Mol. Genet.* 199: 179-182 (1985)), and other methods known to the art. If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U. S. published application No. 2004/0143874.

Transgenic plants without marker genes may be produced using a second plasmid comprising a nucleic acid encoding the marker, distinct from a first plasmid that comprises an A622 or NBB1 sequence. The first and second plasmids or portions thereof are introduced into the same plant cell, such that the selectable marker gene that is transiently expressed, transformed plant cells are identified, and transformed plants are obtained in which the A622 or NBB1 sequence is stably integrated into the genome and the selectable marker gene is not stably integrated. See U. S. published application No. 2003/0221213. The first plasmid that comprises an A622 or NBB1 sequence may optionally be a binary vector with a T-DNA region that is completely made up of nucleic acid sequences present in wild-type non-transgenic *N. tabacum* or sexually compatible *Nicotiana* species.

The *Agrobacterium* transformation methods discussed above are known to be useful for transforming dicots. Additionally, de la Pena et al., *Nature* 325: 274-276 (1987), Rhodes et al., *Science* 240: 204-207 (1988), and Shimamato et al., *Nature* 328: 274-276 (1989) have transformed cereal monocots using *Agrobacterium*. Also see Bechtold et al., *C.R. Acad. Sci. Paris* 316 (1994), illustrating vacuum infiltration for *Agrobacterium*-mediated transformation.

Methods of regenerating a transgenic plant from a transformed cell or culture vary according to the plant species but are based on known methodology. For example, methods for regenerating of transgenic tobacco plants are well-known. Genetically engineered plants are selected that have increased expression of at least one of A622, NBB1, PMT, and QPT. Additionally, the inventive genetically engineered plants may have increased nicotine levels and yield.

Non-Nicotine Producing Cell Transformation

Constructs according to the invention may be used to transform any cell, using a suitable transformation technique, such as *Agrobacterium*-mediated transformation for plant cells, particle bombardment, electroporation, and polyethylene glycol fusion, calcium phosphate transfection, DEAE-dextran mediated transfection, or cationic lipid-mediated transfection.

Non-nicotine producing cells may be transformed with nucleic acid constructs of the present invention without the use of a selectable or visible marker and transgenic organisms may be identified by detecting the presence of the introduced construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, transformed cells may be identified by recognizing differences in the growth rate or a morphological feature of a transformed cell compared to the growth rate or a morphological feature of a non-transformed cell that is cultured under similar conditions. See WO 2004/076625.

For the purposes of the present description, genetically engineered cells are selected that express A622 and NBB1 heterologously.

Quantifying Nicotinic Alkaloid Content

Genetically engineered plants and cells are characterized by increased nicotinic alkaloid content. Similarly, transformed non-nicotine producing cells are characterized by nicotinic alkaloid production.

In describing a plant of the invention, the phrase "increased nicotine or nicotinic alkaloid content" refers to an increase in the amount of nicotinic alkaloid in the plant or cell when compared with a non-transformed control plant or cell. "Increased nicotine plant" encompasses a genetically engineered plant that has an increase in nicotine content greater than 10%, and preferably greater than 50%, 100%, or 200% of the nicotine content of a control plant of the same species or variety.

A successfully transformed non-nicotine producing cell is characterized by nicotinic alkaloid synthesis. For example, a transformed non-nicotine producing cell may produce nicotine, whereas a non-transformed control cell does not.

A quantitative increase in nicotinic alkaloid levels can be assayed by several methods, as for example by quantification based on gas-liquid chromatography, high performance liquid chromatography, radio-immunoassays, and enzyme-linked immunosorbent assays. In the present invention, nicotinic alkaloid levels were measured by gas-liquid chromatography equipped with a capillary column and an FID detector, as described in Hibi et al., Plant Physiology 100: 826-35 (1992).

Quantifying Yield

Genetically engineered plants and cells of the invention are characterized by increased nicotinic alkaloid content and yield. Nicotinic alkaloid production in the genetically engineered plants is preferably achieved by expressing a nicotine biosynthesis pathway gene, such as A622, NBB1, PMT, or QPT.

In describing a plant of the invention, the phrase "increased yield" or "high yielding" refers to an increase in the amount of yield of a plant or crop of said plant when compared to an increased-nicotine control plant or crop of said plant. "Increased yield plant" encompasses a genetically engineered plant that yields the same as a plant or crop or said plant as an increased-nicotine plant or crop of said plant, preferably greater than 110%, and more preferably greater than 125% of the yield of a nicotine-enriched control plant of the same species or variety.

A quantitative increase in photosynthetic efficiency can be assayed by several methods, as for example by quantifying photosynthetic rates, such as gas exchange and $CO_2$ fixation, and chlorophyll florescence. Miyagawa et al., *Plant Cell Physiol.* 41, 311-320 (2000). Photosynthetic rates may also be quantified by measuring metabolite and carbohydrate levels as described by Leegood, Carbon Metabolism In *Photosynthesis and production in a changing environment: a field and laboratory manual* (eds Hall, Scurlock, Bolhar-Nordenkampf, Leegood, & Long) 247-267 (Chapman & Hall, London; 1993). Alternatively, photosynthetic activity may be calculated based on enzyme activity, such as Rubisco activity. Portis, A. R. *J. Exp. Bot.* 46:1285-1291 (1995).

Of course, increased yield can be determined by measuring more readily discernible characteristics, including but not limited to plant height, weight, leaf size, time to flowering, number of seeds produced, and seed weight.

Increased-Nicotine Products

The present invention provides a genetically engineered plant having increased-nicotine levels, as well as a genetically engineered non-nicotine producing cell that produces nicotine or related compounds, where said cell is derived from an organism that does not produce nicotine. A variety of products may be made from such a genetically engineered plant. Likewise, products can be made from cells that are genetically engineered for production of nicotine or related compounds.

Herbivore-Resistant Plant

Nicotine serves as a natural pesticide which helps protect tobacco plants from damage by pests. It has been show that conventionally bred or transgenic low-nicotine tobacco have increased susceptibility to insect damage. Legg, P. D., et al., *Can. J. Cyto.*, 13:287-291 (1971); Voelckel, C., et al., *Chemoecology* 11:121-126 (2001); Steppuhn, A., et al., *PLoS Biol*, 2(8): e217: 1074-1080 (2004). Using the inventive methods and constructs, increased-nicotine plants may be produced that have increased resistance to insect and other pest damage. Similarly, increased pest resistance may achieved in non-nicotine producing plants, such as *A. belladonna* and *A. thaliana*, that are genetically engineered according to the present invention to produce nicotine.

Increased-Nicotine Tobacco Products

The inventive constructs and methods may be used to produce, for example, cigarettes, cigars, and other traditional tobacco products such as snuff and snus. Additionally, increased-nicotine cigarettes may be produced that have reduced-exposure to smoke components, such as tar, yet have similar or increased nicotine deliveries as conventional cigarettes.

In the present description, an increased-nicotine tobacco product may be in the form of leaf tobacco, shredded tobacco, cut rag tobacco, ground tobacco, reconstituted tobacco, expanded or puffed tobacco and tobacco fractions including, for example, nicotine. An increased-nicotine tobacco product may include cigarettes, cigars, pipe tobaccos, and any form of smokeless tobacco such as snuff, snus, or chewing tobacco.

Blending different tobacco types or cultivars within a tobacco product such as a cigarette is common in tobacco art. It will therefore be appreciated that increased-nicotine tobacco could be blended at any percentage with non-transformed tobacco to obtain any level of desired nicotine content, up to the nicotine content of the increased nicotine tobacco utilized, to manufacture a tobacco product.

Increased nicotine cigarettes are particularly advantageous because studies demonstrate that when nicotine is increased, smokers inhale less tar and carbon monoxide. See Armitage et al., Psychopharmacology 96:447-453 (1988); Fagerström, *Psychopharmacology* 77:164-167 (1982); Russell, *Nicotine and Public Health* 15:265-284 (2000) and Woodman et al., *European Journal of Respiratory Disease* 70:316-321 (1987).

Cigarette smoke is an extremely complex mixture of more than 4,000 different compounds. Green & Rodgman, *Recent Advances in Tobacco Science* 22: 131-304 (1996); IOM Report, page 9 of executive summary. Cigarette smoke is made up of two phases: a particulate phase, which is commonly called "tar" or total particulate matter, and a vapor phase, which contains gases and semi-volatile compounds. A common definition for "tar" is "nicotine-free dry smoke" or "nicotine-free dry particulate matter" (NFDPM) captured by a Cambridge pad when a cigarette is machine smoked. More specifically, "tar" is the total particulate matter isolated from smoke, excluding water and nicotine. Tar makes up less than ten percent of the weight of cigarette smoke. Yet, it is the tar component that contains the majority of the most harmful smoke compounds.

Analytical methods combined with sensitive biological assays have led to the identification of 69 carcinogens in tobacco smoke. See THE CHANGING CIGARETTE: CHEMICAL STUDIES AND BIOASSAYS, Chapter 5, Smoking and Tobacco Control Monograph No. 13 (NIH Pub. No. 02-5074, October 2001). It has become clear to researchers, however, that not all components of cigarette smoke have equal toxicity. Notably, the first U.S. Surgeon General's report on smoking in 1964 came to the conclusion that nicotine was probably not toxic at the levels inhaled by smokers, with the implication that the source of the primary pharmacologic reward to smokers was not of immediate concern. The Surgeon General's 1964 report stated, at page 74, that "[t]here is no acceptable evidence that prolonged exposure to nicotine creates either dangerous functional changes of an objective nature or degenerative diseases."

In fact, the U.S. Food and Drug Administration allows the sale of nicotine replacement products such as patches and chewing gum for use in smoking cessation therapy. These products may deliver more nicotine in one day than a pack of cigarettes. Page 167 of the IOM Report states, "Many studies of nicotine suggest that nicotine is unlikely to be a cancer-causing agent in humans or, at worst, that its carcinogenicity would be trivial compared to that of other components of tobacco. The consideration of nicotine as a carcinogenic agent, if at all, is trivial compared to the risk of other tobacco constituents."

Cigarettes are generally rated by the FTC's (in the U.S.) or ISO's smoking-machine methods which determine, for example, the amount of tar and nicotine generated when a cigarette is smoked by a machine in accordance with standardized conditions. See Pillsbury et al., *J. Assoc. Off. Analytical Chem.* (1969); ISO: 4387 (1991). Most commercial cigarettes generally yield about 10 to 15 parts "tar" to every 1 part nicotine, measured in milligrams, as analyzed in PCT application WO 2005/018307. Many public health officials believe that the current FTC/ISO machine smoking regime is flawed since these methodologies fail to take into account human smoking behavior which is primarily driven by nicotine seeking. In other words, these methods don't consider compensatory smoking. Compensatory smoking or compensation, as it is also called, essentially means over smoking (smoking more intensively) due to the reduced presence of nicotine in tobacco smoke or under smoking (smoking less intensively) due to the increased presence of nicotine. See Benowitz, N. Compensatory Smoking of Low Yield Cigarettes, NCI Monograph 13.

Novel smoking-machine methods are currently being evaluated, especially those that consider compensatory smoking of low-yield brands. An example is a method involving the adjustment of smoking parameters so that brands with lower ISO nicotine yields are machine smoked more intensely. Kozlowski and O'Connor Lancet 355: 2159 (2000). Other proposed methods measure yields of toxins on a per nicotine unit basis or at a defined "target" nicotine yield. This is achieved, for example, by systematically varying puff volume, puff interval, and blockage of ventilation holes until the target nicotine yield is reached. Cigarettes can then be rated on the effort required to get the target nicotine yield as well as on toxin delivery at that yield. Consumers would benefit from these smoking-machine methods since comparisons of specific toxins among different brands could be evaluated.

Studies have suggested that many smokers inhale just as much smoke with most "light" and "ultra-light" cigarettes as full flavor cigarettes (Gori and Lynch, *Regulatory Toxicology and Pharmacology* 5:314-326). Smokers may compensate or smoke lower-yield cigarettes (per the FTC or ISO method) more aggressively (than higher-yield cigarettes) in order to obtain their desired nicotine impact and mouth feel of smoke, which are important sensory properties. Rose, J. E. "The role of upper airway stimulation in smoking," in *Nicotine Replacement: A Critical Evaluation*, p.95-106, 1988.

The manner in which a smoker may compensate include the frequency of puffs per cigarette and volume of smoke inhalation of such puffs, duration of the smoke inhalation being held before exhaling, number of cigarettes smoked within a specified time period, and the percentage of each cigarette that is smoked (how far down the cigarette is smoked).

When the percentage of nicotine per unit of inhaled smoke volume increases, many smokers may compensate and inhale less smoke. Gori G. B., *Virtually Safe Cigarettes. Reviving an opportunity once tragically rejected*. IOS Press. Amsterdam, (2000). The higher the percentage of nicotine in cigarette tobacco, the higher the percentage of nicotine in cigarette smoke. More specifically, the higher the percentage of nicotine in a cigarette's filler, the higher the percentage of nicotine in cigarette smoke. "Filler" means any smokable material that is rolled within a cigarette or cigarette-like device and includes (a) all tobaccos, including but not limited to reconstituted and expanded tobaccos, (b) any non-tobacco substitutes that may accompany (a); (c) tobacco casings, (d) other additives including flavorings that (a), (b) or (c) are supplemented with. A cigarette-like device is any device specifically intended to deliver nicotine through an alternative "smoke" aerosol formed by heating tobacco materials. Characteristics of such devices are that they contain a high content of glycerin or a glycerin substitute with minimal or no combustion pyrolysis. Glycerin when heated, vaporizes rapidly and forms an aerosol that can be inhaled and is very similar in appearance and feel to conventional cigarette smoke.

Therefore, the nicotine content of tobacco filler contained within a cigarette or cigarette-like device, all other factors held constant (including but not limited to, the type of filter, cigarette paper including its porosity, plug wraps, and tipping paper utilized, and the amount of filter ventilation), would roughly have to double for a corresponding two-fold increase of nicotine in mainstream cigarette smoke. Further, the nicotine content of tobacco filler contained within a cigarette or cigarette-like device, all other factors held constant, would roughly have to triple for a corresponding three-fold increase of nicotine in mainstream cigarette smoke. The calculations in this section refer to protonated nicotine in the mainstream smoke of a cigarette augmented with the described increase in nicotine levels and not "free" or "volatile" nicotine.

In one preferred embodiment of the invention a reduced-exposure cigarette is manufactured comprising an increased-nicotine tobacco plant having up to a two-fold increase of nicotine. In another preferred embodiment of the present invention a reduced-exposure cigarette is manufactured comprising an increased-nicotine tobacco having greater than a two-fold increase of nicotine.

The variety testing program conducted through the Agricultural Research Service at North Carolina State University evaluates breeding lines through the Regional Minimum Standards Program and commercial varieties through the North Carolina Official Variety Test (NCOVT). The reported total alkaloid concentration of flue-cured commercial varieties in the NCOVT, Three-Year Average from 2001-2003, range from 2.45 to 3.17 percent. Smith et al., "Variety Information," Chapter 3 in: NORTH CAROLINA OFFICIAL VARIETY TEST (2004), Table 3.1. The three-year average total alkaloid concentration was 2.5 percent for K-326, the cultivar utilized in Examples 4-6 and 9-14. The Spectrometric method is used to measure total alkaloid content of tobacco cultivars in the above NCOVT and for purposes of measuring total alkaloid content of tobacco and increased-nicotine plants of the present invention. USA/Technical Advisory Group ISO/TC 126—Tobacco and tobacco products: ISO/DIS 2881. As disclosed herein including within the figures, it is apparent that some increased-nicotine plants have the capacity to at least double or even more than triple the nicotine accumulation of the wild-type K326 controls. Likewise, in Examples 4 to 6, NBB1 and A622 overexpression produces a two-or even a three-fold increase in nicotine compared with wild-type controls.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. "Flue-cured tobacco" refers to a method of drying tobacco plants in a ventilated barn with heat and is characterized by a unique color, high reducing sugar content, medium to heavy in body and exceptionally smooth smoking properties. Bacon et al., *Ind. Eng. Chem.* 44: 292 (1952).

Tobacco-specific nitrosamines (TSNAs) are a class of carcinogens that are predominantly formed during curing and processing. Hoffman, D., et al., *J. Natl. Cancer Inst.* 58, 1841-4 (1977); Wiernik A et al., *Recent Adv. Tob. Sci*, (1995), 21: 39-80. TSNAs, such as 4-(N-nitrosomethylamino)-1-(3-pyridyl)-1-butanone (NNK), N'-nitrosonornicotine (NNN), N'-nitrosoanatabine (NAT), and N'-nitrosoanabasine (NAB), are formed by N-nitrosation of nicotine and other minor *Nicotiana* alkaloids, such as nornicotine, anatabine, and anabasine.

Increased-nicotine tobacco may contain higher nitrosamines since there is a positive correlation between alkaloid content in tobacco and TSNA accumulation. For example, a significant correlation coefficient between anatabine and NAT was found to be 0.76. Djordjevic et al., *J. Agric. Food Chem.*, 37: 752-56 (1989). However, U.S. Pat. Nos. 5,803,081, 6,135,121, 6,805,134, 6,895,974 and 6,959,712 and U.S. Published Applications 2005/0034365, 2005/0072047, 2005/0223442, 2006/0041949, and PCT published application WO 2006/091194, and others, discuss methodology to reduce tobacco-specific nitrosamines, which can be applied to a tobacco product that utilizes the subject invention.

Accordingly, the present invention provides constructs and methodology for producing cigarettes and other tobacco products containing increased nicotine levels. A desirable reduced-exposure cigarette should deliver a smoker's desired level of nicotine per cigarette as efficiently as possible while maintaining acceptable taste. See WO 05/018307.

Reconstituted Tobacco, Expanded Tobacco and Blending

Increased-nicotine tobacco also may be used to produce reconstituted sheet tobacco (Recon) and expanded tobacco or puffed tobacco. Recon can be produced from the following: tobacco dust, stems, small leaf particles, other byproducts of tobacco processing and cigarette manufacturing, and sometimes straight whole leaf. The recon process, which varies by manufacturer, closely resembles the typical paper making process and entails processing the various tobacco fractions and then cutting the recon sheets into a size and shape that resembles cigarette tobacco (cut-rag tobacco).

In addition, increased-nicotine tobacco may be used, according to the present invention, to produce expanded tobacco, also known as puffed tobacco, which is an important component in many cigarette brands. Expanded tobacco is made through expansion of suitable gases, whereby the tobacco is "puffed," resulting in reduced density and greater filling capacity, which in turn reduces the weight of tobacco used in cigarettes. By using increased-nicotine tobacco as a starting material, cigarettes made with the resultant expanded tobacco will yield reduced ratios of toxic chemicals, such as tar and carbon monoxide, to nicotine.

Increased-nicotine expanded tobacco, increased-nicotine Recon, and increased-nicotine cut-rag tobacco can be blended at any percentage among the three or with any percentages of non-transformed expanded tobacco, non-transformed recon or non-transformed cut-rag to produce cigarette filler containing varying nicotine contents. Any such blend is then incorporated into the cigarette making process according to standard methods known in the art.

Tobacco products other than cigarettes utilizing GE increased-nicotine tobacco are manufactured using any of the tobacco plant material described herein according to standard methods known in the art. In one embodiment, tobacco products are manufactured comprising plant material obtained from increased-nicotine tobacco. The increased-nicotine content can be up to greater than three times that of wild type cultivars.

Nicotinic Alkaloid Enzymes and Analogs

In addition to traditional tobacco products, such as cigarettes and chewing tobacco, the present invention provides methodology for producing nicotine and nicotine analogs, as well as enzymes for synthesis of nicotine and nicotine analogs. These compounds may be produced by genetically engineered nicotine-producing plants and non-nicotine producing cells, as well as in a cell-free/in vitro system.

Because recent studies suggest a role for nicotine receptors in treating a variety of conditions and disorders, such as Alzheimer's disease, schizophrenia, central and autonomic nervous systems dysfunction, and addictions, there is a need for nicotine receptor ligand sources. For example, the inventive methods and constructs may be used for producing nicotinic alkaloids. It has been shown that transgenic hairy root cultures overexpressing PMT provide an effective means for large-scale commercial production of scopolamine, a pharmaceutically important tropane alkaloid. Zhang et al., *Proc. Nat'l Acad. Sci. USA* 101: 6786-91 (2004). Accordingly, large-scale or commercial quantities of nicotinic alkaloids can be produced in tobacco hairy root culture by expressing at least one of A622 and NBB1. Likewise, the present invention contemplates cell culture systems, such as bacterial or insect cell cultures, for producing large-scale or commercial quantities of nicotine by expressing A622 and NBB1.

Additionally, products can be made directly using the activity of NBB1 and A622 enzymes. For example, recombinant NBB1 and A622 enzymes may be used for the synthesis, or partial synthesis, of nicotinic alkaloids or nicotinic alkaloid analogs. Accordingly, large-scale or commercial quantities of A622 and NBB1 can be produced by a variety of methods, including extracting recombinant enzyme from a genetically engineered plant, cell, or culture system, including but not limited to hairy root cultures, insect, bacterial, fungal, plant, algae, and mammalian cell culture, or in vitro.

Specific examples are presented below of methods for identifying sequences encoding enzymes involved in nicotine biosynthesis, as well as for introducing the target gene to produce plant transformants. They are meant to be exemplary and not as limitations on the present invention.

Example 1: Identification of NBB1 as a Gene Regulated by the NIC Loci

A cDNA microarray prepared from a *Nicotiana sylvestris*-derived cDNA library, see Katoh et al., *Proc. Japan Acad.* 79, Ser. B: 151-54 (2003), was used to search for novel genes which are controlled by the nicotine biosynthesis regulatory NIC loci.

*N. sylvestris* cDNAs were amplified by PCR and spotted onto mirror-coated slides (type 7 star, Amersham) using an Amersham Lucidea array spotter. DNA was immobilized on the slide surface by UV crosslinking (120 mJ/m$^2$). *N. tabacum* Burley 21 plantlets (WT and nic1nic2) were grown on half-strength B5 medium supplemented with 1.5% (W/V) sucrose and 0.35% (W/V) gellan gum (Wako) in Agripot containers (Kirin).

Roots of eight-week-old plantlets were harvested, immediately frozen with liquid nitrogen, and kept at −80° C. until use. Total RNA was isolated using Plant RNeasy Mini kit (Qiagen) from the frozen roots, and mRNA was purified using GenElute mRNA Miniprep kit (Sigma). cDNA was synthesized from 0.4 μg of the purified mRNA by using LabelStar Array Kit (Qiagen) in the presence of Cy3 or Cy5-dCTP (Amersham). cDNA hybridization to the microarray slides and post-hybridization washes were performed using a Lucidea SlidePro hybridization machine (Amersham). Microarrays were scanned using an FLA-8000 scanner (Fujifilm). Acquired array images were quantified for signal intensity with ArrayGauge software (Fujifilm). cDNA probes from wild type and nic1nic2 tobacco were labeled with Cy3 and Cy5 in reciprocal pair-wise combinations. Hybridization signals were normalized by accounting for the total signal intensity of dyes. cDNA clones which hybridized to wild-type probes more than twice as strongly compared to nic1nic2 probes were identified, and these included NBB1.

Full-length NBB1 cDNA was obtained by 5'- and 3'-RACE from total RNA of N. tabacum by using a SMART RACE cDNA Amplification Kit (Clontech). The resultant full-length NBB1 cDNA sequence was cloned into pGEM-T vector (Promega) to give pGEMT-NBB1cDNAfull.

The nucleotide sequence of the NBB1 cDNA insert was determined on both strands using an ABI PRISM® 3100 Genetic Analyzer (Applied Biosystems) and a BigDye® Terminator v3.1 Cycle Sequencing Kit (Applied Biosystems). The NBB1 full-length cDNA is set forth in SEQ ID NO: 1. The amino acid sequence encoded by the nucleotide sequence is set forth in SEQ ID NO: 2. The protein sequence includes a FAD-binding motif. A putative vacuolar signal peptide is located at the N-terminus.

Example 2: Characterization of NBB1

NBB1 expression in tobacco plants was investigated by Northern blot analysis.

Plants of Nicotiana tabacum cv. Burley 21 (abbreviated below as WT) and mutant lines in which nic1, nic2 or both nic1 and nic2 mutations had been introduced in the Burley 21 background were grown in vitro for 2 months at 25° C. with 150 μmole photons/m² of light (16 h light, 8 h dark) on ½×B5 medium with 3% sucrose and 0.3% gellan gum. The plants were treated with methyl jasmonate vapor by adding 0.5 mL of 100 μM methyl jasmonate to an Agripot container (Kirin, Tokyo) with a solid medium capacity of 80 cm³ and a gas capacity of 250 cm³ containing the plants. The treatment times were set at 0 h and 24 h. The root parts and leaf parts (2$^{nd}$ through 6$^{th}$ leaves from a plant body with a total of 7 to 10 leaves) were collected from the plant bodies and immediately stored frozen using liquid nitrogen.

RNA was extracted using an RNeasy Midi Kit (Qiagen) according to the manufacturer's protocol. However, polyvinyl pyrrolidine was added to a concentration of 1% to RLT Buffer in the Qiagen kit. The column operation was performed twice to increase the purity of the RNA.

RNA blotting was carried out according to the methods given by Sambrook and Russell (Sambrook, J. et al., Molecular Cloning, Cold Spring Harbor Laboratory, Chapter 7 (2001)).

The sequence fragment from 1278 bp through the end (1759 bp) of the NBB1 nucleotide sequence (SEQ ID NO: 1) was used as the probe template. The template was prepared by amplification from the cDNA clone by PCR using the following primers:

```
primer 1:
                                    (SEQ ID NO: 13)
             GGAAAACTAACAACGGAATCTCT primer 2:
                                    (SEQ ID NO: 14)
             GATCAAGCTATTGCTTTCCCT
```

The probe was labeled with $^{32}$P using a Bcabest labeling kit (Takara) according to the manufacturer's instructions. Hybridization was accomplished using ULTRAhyb (Ambion) as the buffer according to the manufacturer's protocol.

PMT probe was prepared from a PMT sequence cloned into a pcDNAII vector in E. coli (Hibi et al., 1994). The plasmid was extracted and purified from the E. coli using a QIAprep Spin Miniprep Kit (Qiagen), treated with the restriction enzymes XbaI and HindIII by ordinary methods, and the digested DNA was electrophoresed through an agarose gel. DNA fragments of about 1.5 kb were collected using a QIAquick Gel Extraction Kit (Qiagen). The collected DNA fragments were $^{32}$P labeled by the same methods used for the NBB1 probe, and hybridized.

As FIG. 1 shows, NBB1 and PMT have the same pattern of expression in tobacco plants. Evidence that NBB1 is involved in nicotine biosynthesis is that, like PMT, NBB1 is under the control of the NIC genes, and it exhibits a similar pattern of expression to PMT.

Example 3: Phylogenetic Analysis of NBB1

NBB1 polypeptide has 25% identity and 60% homology to the Eschscholzia californica berberine bridge enzyme (BBE). Dittrich et al., Proc. Nat'l Acad. Sci. USA 88: 9969-73 (1991)). An alignment of the NBB1 polypeptide with EcBBE is shown in FIG. 2.

A phylogenetic tree was constructed using the sequences of NBB1 polypeptide and plant BBE-like polypeptides, based on Carter & Thornburg, Plant Physiol. 134: 460-69 (2004). The phylogenetic analysis was performed using neighbor-joining method with the CLUSTAL W program. Numbers indicate bootstrap values from 1,000 replicates. The sequences used were: EcBBE, California poppy BBE (GenBank accession no. AF005655); PsBBE, opium poppy (Papaver somniferum) probable reticuline oxidase (AF025430); BsBBE, barberry (Berberis stolonifera) BBE (AF049347); VuCPRD2, cowpea (Vigna unguiculata) drought-induced protein (AB056448); NspNEC5, Nicotiana sp. Nectarin V (AF503441/AF503442); HaCHOX, sunflower (Helianthus annuus) carbohydrate oxidase (AF472609); LsCHOX, lettuce (Lactuca sativa) carbohydrate oxidase (AF472608); and 27 Arabidopsis genes (At1g01980, At1g11770, At1g26380, At1g26390, At1g26400, At1g26410, At1g26420, At1g30700, At1g30710, At1g30720, At1g30730, At1g30740, At1g30760, At1g34575, At2g34790, At2g34810, At4g20800, At4g20820, At4g20830, At4g20840, At4g20860, At5g44360, At5g44380, At5g44390, At5g44400, At5g44410, and At5g44440).

Figure 3:
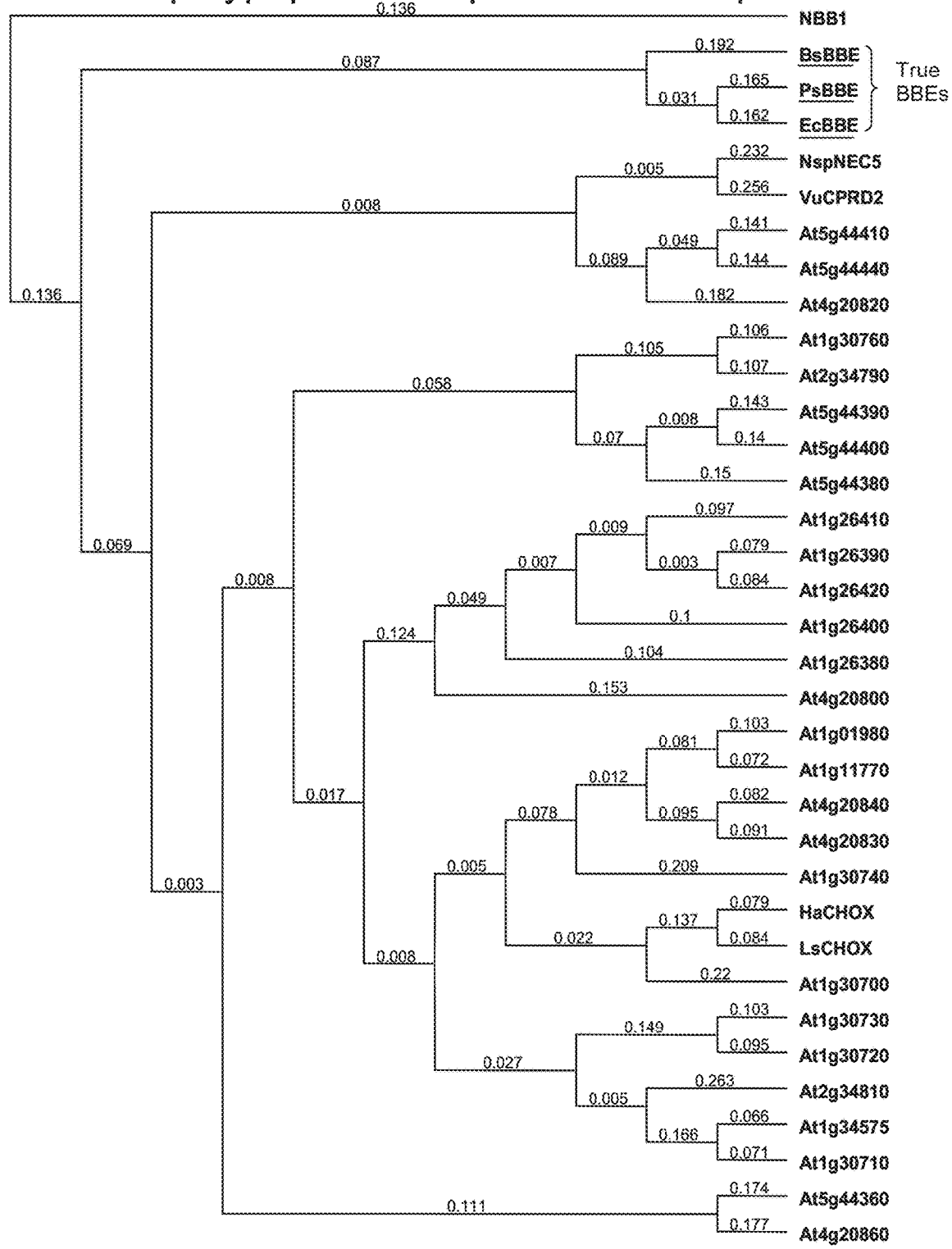
FIG. 3: Phylogenetic tree constructed using the sequences of NBB1 polypeptide and plant BBE-like proteins

The results are shown in FIG. 3. The three known BBEs form a separate clade and are underlined and indicated as "True BBEs." The sequence of NBB1 is not highly similar to any of the BBE or BBE-like proteins, and is separated from the other sequences at the base of the tree. The only other BBE-like protein described from the genus Nicotiana, nectarin V, a protein described in nectar of the a hybrid ornamental Nicotiana langsdorffii×N. sanderae, Carter and Thornburg (2004), clusters with the cowpea drought-induced protein and several putative BBE-like proteins from *Arabidopsis*. Because the nectar of the ornamental tobacco lacks alkaloids and nectarin V has glucose oxidase activity, it was concluded that nectarin V is involved in antimicrobial defense in flowers and is not likely to have any role in alkaloid synthesis. Id.

Example 4: NBB1 Overexpression in Tobacco Hairy Roots

Preparation of NBB1 Overexpression Construct

An attB-NBB1 fragment was amplified by PCR using the pGEMT-NBB1cDNAfull vector of Example 1 as the template and two sets of primers; one set for the NBB1 gene-specific amplification (gene-specific primers) and another set to add the attB sequences (adapter primers). PCR conditions were those recommended by the manufacturer. The GATEWAY entry clone pDONR221-NBB1 was created by a BP recombination reaction between the attB-NBB1 PCR product and pDONR221(Invitrogen).

```
Gene-specific primers
NBB1-attB1
                                    (SEQ ID NO: 15)
5' AAAAAGCAGGCTCACCATGTTTCCGCTCATAATTCTG NBB1-attB2
                                    (SEQ ID NO: 16)
5' AGAAAGCTGGGTTCATTCACTGCTATACTTGTGC Adapter primers
attB1 adapter
                                    (SEQ ID NO: 17)
5' GGGGACAAGTTTGTACAAAAAAGCAGGCT attB2 adapter
                                    (SEQ ID NO: 18)
5' GGGGACCACTTTGTACAAGAAAGCTGGGT
```

Description of pTobRD2-DEST

A TobRD2 promoter region (SEQ ID NO: 5 in WO9705261) of 1,031 bp was amplified using Burley 21 genomic DNA as the template and the TobRD2 promoter-specific primers, and then digested with HindIII and XbaI.

```
TobRD2 promoter-specific primers:
TobRD2-01F
                                    (SEQ ID NO: 19)
5' AAAGCTTGGAAACATATTCAATACATTGTAG
HindIII site is underlined.

TobRD2-02R
                                    (SEQ ID NO: 20)
5' TCTAGATTCTACTACTATTTTATAAGTG
XbaI site is underlined.
```

Figure 4A:
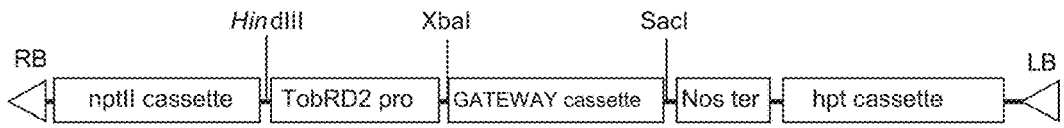
FIG. 4A: T-DNA region of pTobRD2-DEST

The resultant fragment was cloned between the HindIII and XbaI sites of pBI101H (supplied from Dr. Shuji Yokoi of NAIST; ref. *Molecular Breeding* 4: 269-275, 1998) resulting in plasmid pTobRD2-BI101H. A GATEWAY cassette containing attR recombination sites flanking a ccdB gene and a chloramphenicol-resistance gene was cloned between the XbaI and SacI sites of the pTobRD2-BI101H binary vector to produce the binary vector pTobRD2-DEST, which has a T-DNA region containing an NPTII gene expression cassette (Nos promoter-neomycin phosphotransferase II ORF-Nos terminator) and an HPT gene expression cassette (CaMV 35S promoter-hygromycin phosphotransferase ORF-Nos terminator) as selection markers flanking a TobRD2 promoter adjacent to a GATEWAY cassette. A diagram of the T-DNA region of pTobRD2-DEST is shown in FIG. 4A.

Figure 4B:
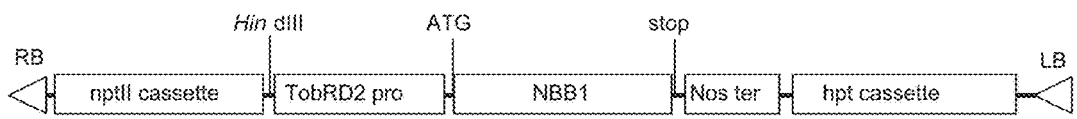
FIG. 4B: T-DNA region of pTobRD2-NBB1ox

The NBB1 ORF was transferred by an LR reaction from the pDONR221-NBB1 vector to a GATEWAY binary vector pTobRD2-DEST, which was designed to express a cloned ORF under the TobRD2 promoter. A diagram of the T-DNA region of the final expression vector, pTobRD2-NBB1 ox, is shown in FIG. 4B.

Production of Transgenic Hairy Roots

The binary vector pTobRD2-NBB1ox was introduced to *Agrobacterium rhizogenes* strain 15834 by electroporation. *Nicotiana tabacum* cv. K326 wild-type plants were transformed by *A. rhizogenes* using a leaf-disc method, basically as described by Kanegae et al., *Plant Physiol.* 105:2:483-90 (1994). Kanamycin resistance (200 mg/L in B5 medium) was used as a selection marker for the pTobRD2-NBB1ox transformed lines (TN lines). Wild-type *A. rhizogenes* was used to produce control hairy root lines (WT lines). Tobacco hairy roots were grown in the B5 liquid medium at 27° C. under the dark condition for two weeks, and then harvested.

Procedure for Analyzing Expression

Figure 5A:
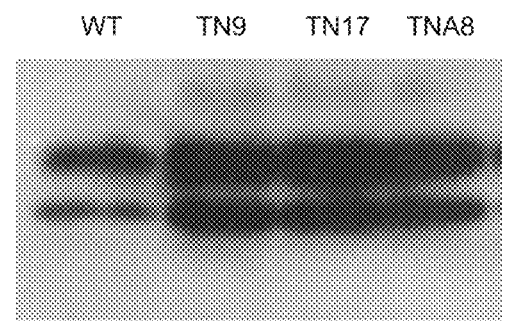
FIG. 5A: Immunoblot analysis of NBB1 in tobacco hairy roots

Expression levels of the NBB1 protein were analyzed by an immunoblot analysis. Hairy roots were frozen in liquid nitrogen, and immediately homogenized using a mortar and pestle in an extraction buffer (100 mM Tris-HCl pH6.8, 4% SDS, 20% glycerol) containing 1 mM phenylmethylsulfonyl fluoride and 200 mM dithiothreitol. After centrifugation of the homogenates, soluble proteins in the supernatant were separated by SDS-PAGE. Immunoblot analysis was performed using an anti-NBB1 rabbit serum. The detailed procedures were reported previously. Shoji et al., *Plant Mol. Biol.*, 50, 427-440 (2002). Immunoblots with anti-NBB1 antiserum show that the transgenic hairy root lines TN9 and TN17 have increased levels of NBB1 protein. See FIG. 5A.

Procedure for Analyzing Alkaloid Levels

Transgenic hairy roots were cultured for two weeks, collected, and freeze dried. 2 ml of 0.1 N sulfuric acid was added to 19 mg of the freeze-dried sample. This suspension was sonicated for 15 minutes, and filtered. Ammonium hydroxide (0.1 ml, 28% $NH_3$; Wako) was added to 1 ml of the filtrate, and the mixture was centrifuged for 10 minutes at 15,000 rpm. A sample of the supernatant (1 ml) was loaded onto an Extrelut-1 column (Merck) and let sit for 5 minutes. Alkaloids were eluted with 6 ml of chloroform. The eluted chloroform fraction was then dried under reduced pressure at 37° C. with an evaporator (Taitec Concentrator TC-8). The dried sample was dissolved in 50 µl of ethanol solution containing 0.1% dodecane. A gas chromatography apparatus (GC-14B, Shimadzu) equipped with a capillary column (Rtx-5Amine column, Restec) and an FID detector was used to analyze the samples. The column temperature was maintained at 100° C. for 10 min, elevated to 150° C. at 25° C./min, held at 150° C. for 1 min, elevated to 170° C. at 1° C./min, held at 170° C. for 2 min, elevated to 300° C. at 30° C./min, and then held at 300° C. for 10 min. Injection and detector temperature was 300° C. A 1 µl sample of the purified alkaloid preparation was injected, and alkaloid contents were measured by the internal standard method.

Figure 6:
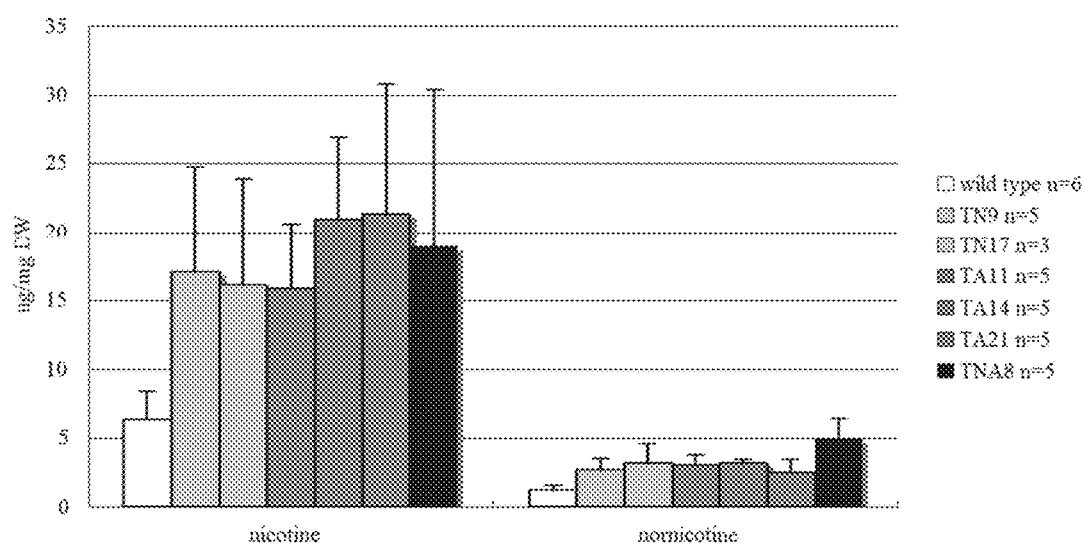
FIG. 6: Nicotine alkaloid contents in hairy roots of TobRD2-NBB1 (TN), TobRD2-A622 (TA), TobRD2-NBB1-A622 (TNA)

The hairy root lines transformed with the NBB1 overexpression vector pTobRD2-NBB1ox (TN9, TN17) have increased levels of nicotine and nornicotine compared to wild type hairy root lines. See FIG. 6.

Example 5: A622 Overexpression in Tobacco Hairy Roots

Preparation of A622 Overexpression Construct

An attB-A622 fragment was amplified using the pcDNAII-A622 vector, per Hibi et al, *Plant Cell* 6: 723-35

(1994), as the template, the A622-specific primers below, and adapter primers, as described above for Example 4.

```
Gene-specific primers
A622-attB1
                                        (SEQ ID NO: 21)
5' AAAAAGCAGGCTTCGAAGGAGATAGAACCATGGTTGTATCAGAGAA

AAGCA

A622-attB2
                                        (SEQ ID NO: 22)
5' AGAAAGCTGGGTCCTAGACAAATTTGTTGTAGAACTCGTCG
```

Figure 4C:
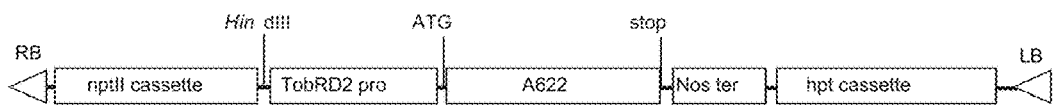
FIG. 4C: T-DNA region of pTobRD2-A622ox

The amplified A622 fragment was cloned into the pDONR221 vector by BP reaction, resulting in pDONR-A622, and then the A622 fragment was transferred from pDONR-A622 to pTobRD2-DEST by an LR reaction. The resultant expression vector was referred to as pTobRD2-A622ox. A diagram of the T-DNA region of pTobRD2-A622ox is shown in FIG. 4C.

Production of Transgenic Hairy Roots

*N. tabacum* cv. K326 wild-type plants were transformed by *A. rhizogenes* 15834 containing the pTobRD2-A622ox vector, as described above for Example 4. Transgenic hairy roots carrying the T-DNA from pTobRD2-A622ox were referred to as TA lines, and cultured as described above in Example 4.

Procedure for Analyzing Expression

Figure 5B:
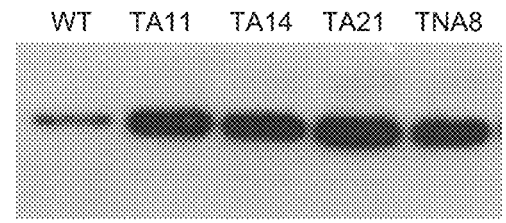
FIG. 5B: Immunoblot analysis of A622 in tobacco hairy roots

Immunoblot analysis was performed as described above in Example 4, except that anti-A622 mouse serum was used for A622 protein detection. Hairy root lines TA11, TA14, TA21 transformed with the A622 overexpression vector have higher levels of A622 protein. See FIG. 5B Procedure for Analysis of Alkaloid Levels Tobacco alkaloids were extracted, purified, and analyzed as described above in Example 4. Hairy root lines TA11, TA14, TA21 transformed with the A622 overexpression vector have higher levels of nicotine and nornicotine. See FIG. 6.

Example 6: NBB1 and A622 Overexpression in Tobacco Hairy Roots

Preparation of A622 and NBB1 Overexpression Construct

Figure 4D:
FIG. 4D: T-DNA region of pTobRD2-A622ox-NBB1 ox

In order to express both A622 and NBB1 proteins from a single T-DNA, the TobRD2-A622 expression cassette and the TobRD2-NBB1 expression cassette were cloned in tandem in a binary vector. The TobRD2-A622 cassette was cut from pTobRD2-A622ox with HindIII, and then cloned into the HindIII site at the 5' end of the TobRD2 promoter in pTobRD2-NBB1 ox. The resultant vector for overexpression of both NBB1 and A622 was referred to as pTobRD2-A622ox-NBB1 ox. A diagram of the T-DNA region of pTobRD2-A622ox-NBB1ox is shown in FIG. 4D.

Production of Transgenic Hairy Roots

*Nicotiana tabacum* cv. K326 wild-type plants were transformed by *A. rhizogenes* 15834 containing the pTobRD2-A622ox-NBB1 ox vector, as described above for Example 4. Transgenic hairy roots carrying the T-DNA from pTobRD2-A622ox-NBB1ox were referred to as TNA lines, and cultured as described above in Example 4.

Procedure for Analyzing Expression

Immunoblot analysis was performed as described above in Example 4, except that both anti-A622 mouse serum and anti-NBB1 rabbit serum were used for protein detection. In the hairy root line TNA8 the expression level of both NBB1 (see FIG. 5A) and A622 (see FIG. 5B) are increased compared to wild type hairy root lines.

Procedure for Analyzing Alkaloid Levels

Tobacco alkaloids were extracted from hairy root line TNA8, purified, and analyzed as described above in Example 4. The levels of nicotine and nornicotine are higher in line TNA8 than in wild type hairy root lines. (See FIG. 6)

Example 7: Transgenic *A. belladonna* Plants Expressing A622 Protein

*Atropa belladonna* produces tropane alkaloids, hyoscyamine and scopolamine, which are derived from the N-methylpyrrolinium cation, but does not contain nicotine alkaloids, possibly due to the absence of NBB1 and A622 genes.

Tobacco A622 cDNA containing an introduced NcoI site at the first ATG was excised from the pcDNAII-A622 vector (Hibi et al. 1994) as an NcoI-BamHI fragment and cloned into pRTL2 (Restrepo et al., *Plant Cell* 2:987-98 (1990)) under the control of a CaMV35S promoter with a duplicated enhancer. This A622 overexpression cassette was excised with HindIII and cloned in a binary vector pGA482 (Amersham) to produce the A622 expression vector pGA-A622.

Production of Transgenic Plants

The binary vector pGA-A622 was introduced to *A. tumefaciens* strain EHA105 by electroporation. *A. belladonna* plants were transformed by *A. tumefaciens* using a leaf-disk method, basically as described by Kanegae et al., (*Plant Physiol.* 105(2):483-90 (1994)). Kanamycin resistance (200 mg/L in MS/B5 medium) was used as a selection marker for the pGA-A622 transformation. Transgenic 35S-A622 plants were regenerated from the leaf discs, grown at 22° C. under continuous light in a growth chamber.

Procedure for Analyzing Expression

Figure 7:
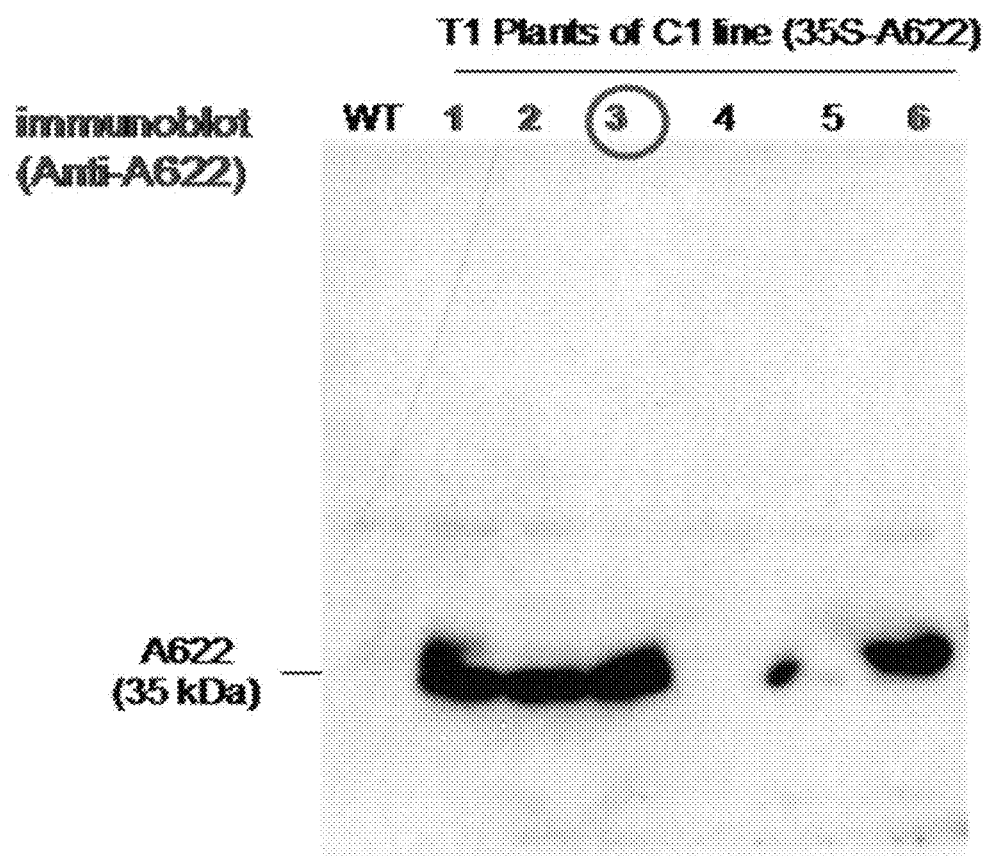
FIG. 7: Expression of A622 Protein in Transgenic *A. belladonna

Total proteins were extracted from leaves of wild-type and 35S-A622 T1 plants, as described above in Example 5. Immunoblot analysis was performed using anti-A622 mouse serum. Leaf tissues of the self-pollinated T1 generation plants that contained high amounts of A622 protein, such as line C1#3 (see FIG. 7), were used for alkaloid analysis.

Procedure for Analysis of Alkaloid Levels

Nicotinic alkaloids in transgenic *A. belladonna* plants were extracted with 1M $H_2SO_4$ and purified basically as described (Hashimoto et al., 1992). Alkaloids were identified by gas chromatography-mass spectrometry (GC-MS) (Hewlett Packard 5890 series II/JEOL MStation JMS700 with HP-5 ms column) after comparison of their mass spectra to those of authentic standards. The column temperature was maintained at 100° C. for 10 min, elevated to 150° C. at 25° C./min, held at 150° C. for 1 min, elevated to 170° C. at 1° C./min, held at 170° C. for 2 min, elevated to 300° C. at 30° C./min, and then held at 300° C. for 10 min. Introduction of A622 alone in *A. belladonna* did not result in accumulation of nicotine or other nicotine alkaloids.

Example 8: Transgenic *A. belladonna* Hairy Roots Expressing NBB1 Protein and A622 Protein Preparation of NBB1 Overexpression Construct To test whether the combination of NBB1 and A622 is sufficient for the coupling reaction of nicotinic alkaloids, we produced transgenic *A. belladonna* hairy roots that express both A622 and NBB1, by transforming leaves of the A622-expressing *Atropa* plants of Example 7 with *A. rhizogenes* strain 15834, which carries an NBB1 expression vector.

Description of pBI101H-E2113-DEST

Figure 4E:
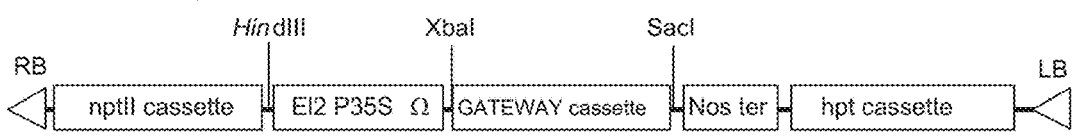
FIG. 4E: T-DNA region of pBI101H-E2113-DEST

The binary vector pBE2113 carrying CaMV35S promoter with a duplicated enhancer (E12) and 5'-upstream sequence of tobacco mosaic virus (Ω) was obtained from Dr. Yuko Ohashi, National Institute of Agrobiological Resources (Tsukuba, Japan), see *Plant Cell Physiol.* 37: 49-59 (1996), and was converted into a GATEWAY destination vector after the GATEWAY cassette, containing attR recombination sites flanking a ccdB gene and a chloramphenicol-resistance gene, was cloned between the XbaI and SacI sites in the vector, which replaced the β-glucronidase gene with the GATEWAY cassette. The resultant destination binary vector was digested with HindIII and SacI, and the HindIII-SacI fragment containing the E12-35S-Ω-GATEWAY cassette was cloned between the HindIII and SacI sites in pBI101H. The resultant destination binary vector was referred to as pBI101H-E2113-DEST. A diagram of the T-DNA region of pBI101H-E2113-DEST is shown in FIG. 4E.

Figure 4F:
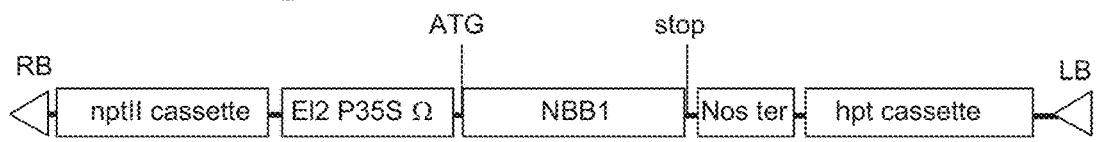
FIG. 4F: T-DNA region of pEII235SΩ-NBB1

NBB1 ORF was transferred from the pDONR221-NBB1-2 vector to the GATEWAY binary vector pBI101H-E2113-DEST by an LR reaction. The expression vector was referred to as pE1235SΩ-NBB1. A diagram of the T-DNA region of pE1235SΩ-NBB1 is shown in FIG. 4F.

Production of Transgenic Hairy Roots

The binary vector pE1235SΩ-NBB1 was introduced to *A. rhizogenes* strain 15834 by electroporation. Leaf tissues of the T1 generation plant containing a 35S-A622 cassette that expresses A662 (line C1#3) were transformed with *A. rhizogenes* carrying pE1235SΩ-NBB1 using a leaf-disc method, basically as described by Kanegae et al. (*Plant Physiol.* 105(2):483-90 (1994)). Hygromycine resistance (30 mg/L in B5 medium) was used as a selection marker. Transgenic hairy roots carrying the T-DNA from pE1235SΩ-NBB1 (line E) and transgenic hairy root infected wild-type *A. rhizogenes* without T-DNA as the control (WT line) were grown in the MS/B5 liquid medium for two weeks and then harvested.

Expression Analysis

Figure 8:
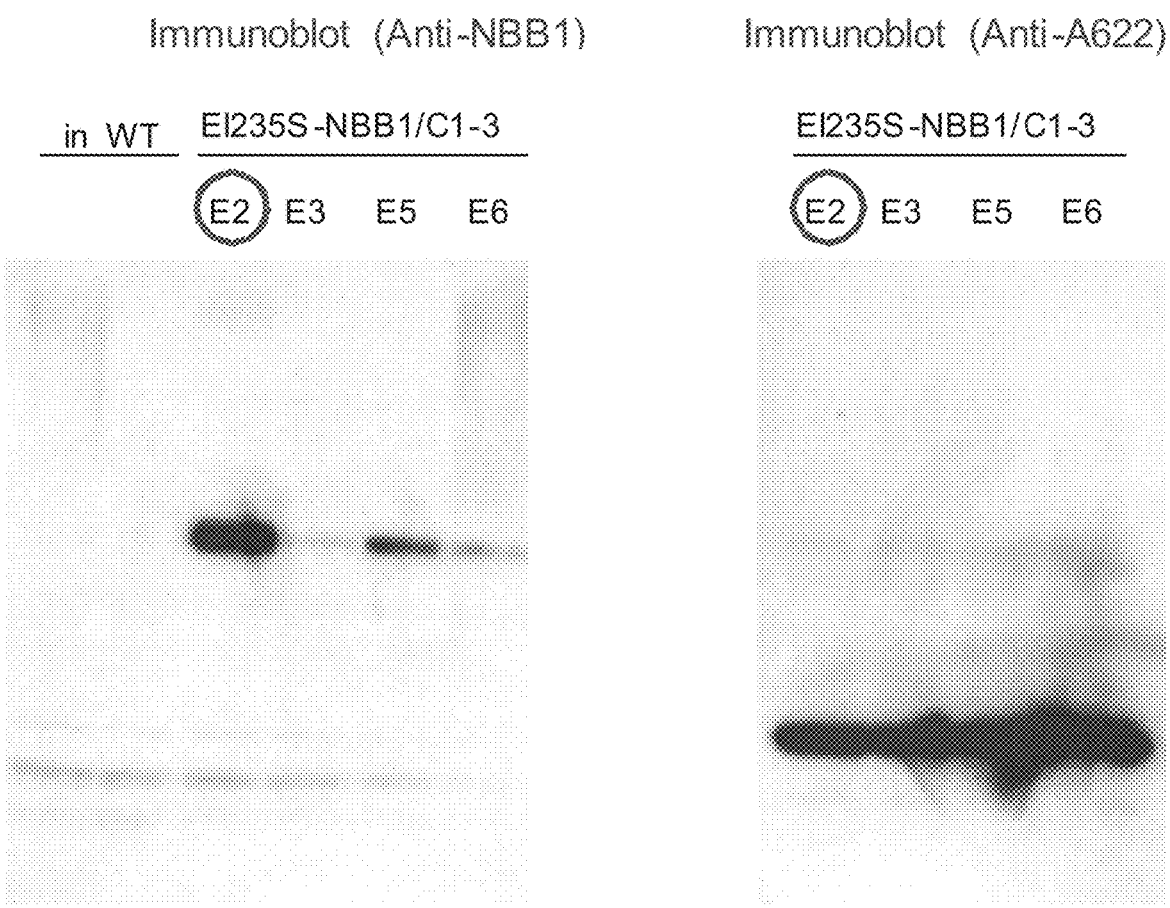
*
FIG. 8: Transgenic *A. belladonna* Expressing NBB1 and A622

Total proteins were extracted and immunoblot analysis was performed as described above in Example 4. Anti-A622 mouse serum was used for A622 protein detection, whereas anti-NBB1 rabbit serum was used for NBB1 protein detection. A transgenic *A. belladonna* hairy root line (E2) expresses high amounts of both NBB1 and A622 proteins (see FIG. 8).

Alkaloid Analysis

The transgenic *A. belladonna* E2 and WT hairy roots were cultured for 3 weeks in 100 ml of MS/B5 liquid medium containing 100 mg/l nicotinic acid. Nicotine alkaloids in E2 and WT hairy roots were extracted with 1M $H_2SO_4$ and purified basically as described (Hashimoto et al., 1992). Alkaloids were identified by gas chromatography-mass spectrometry (GC-MS) (Hewlett Packard 5890 series II/JEOL MStation JMS700 with HP-5 ms column) after comparison of their mass spectra to those of authentic standards. The column temperature was maintained at 100° C. for 10 min, elevated to 150° C. at 25° C./minute, held at 150° C. for 1 minute, elevated to 170° C. at 1° C./min, held at 170° C. for 2 minutes, elevated to 300° C. at 30° C./min, and then held at 300° C. for 10 minutes.

Figure 9:
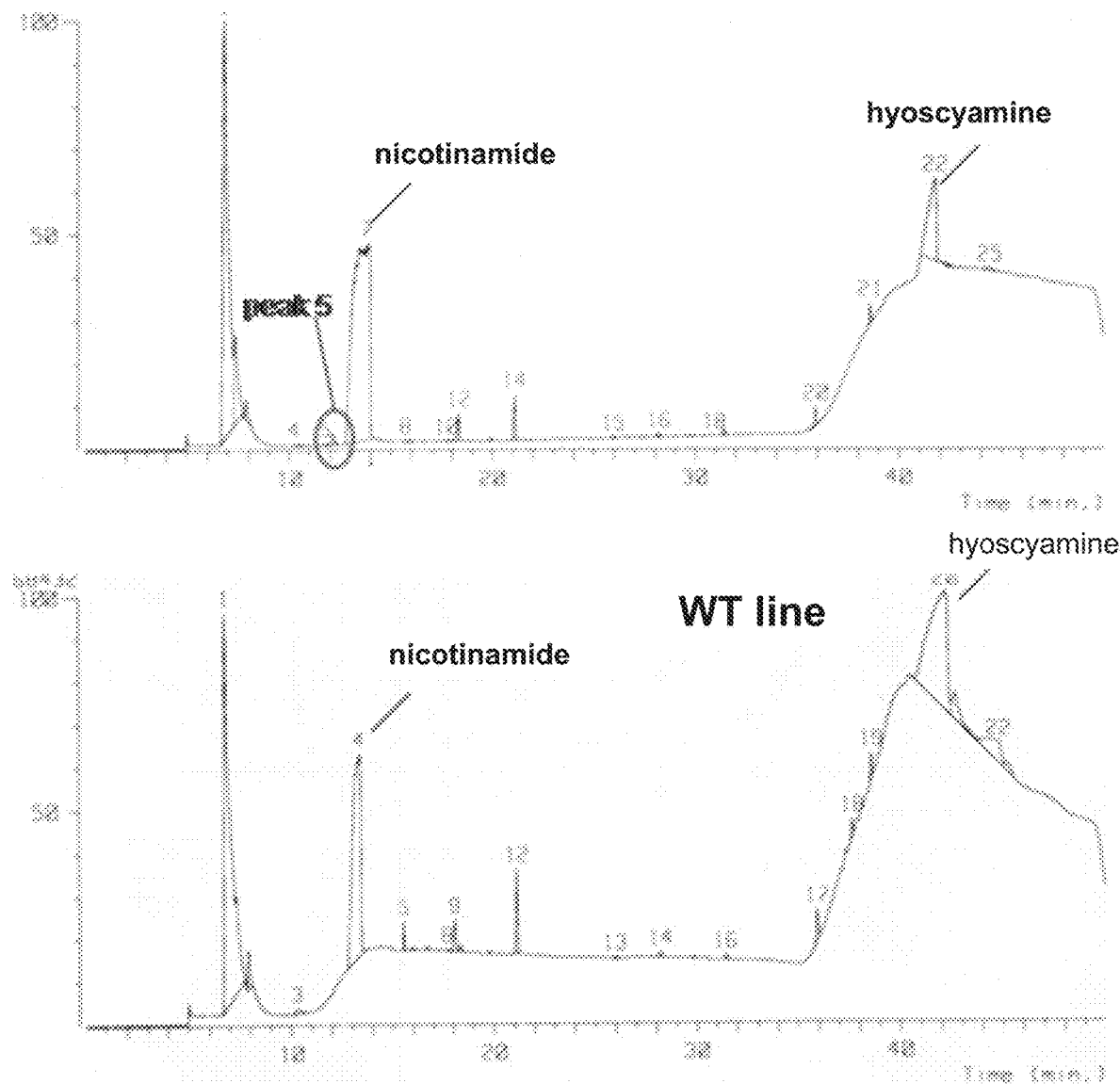
FIG. 9: Nicotine synthesis in transgenic *A. belladonna* hairy roots expressing NBB1 and A622
Figure 10:
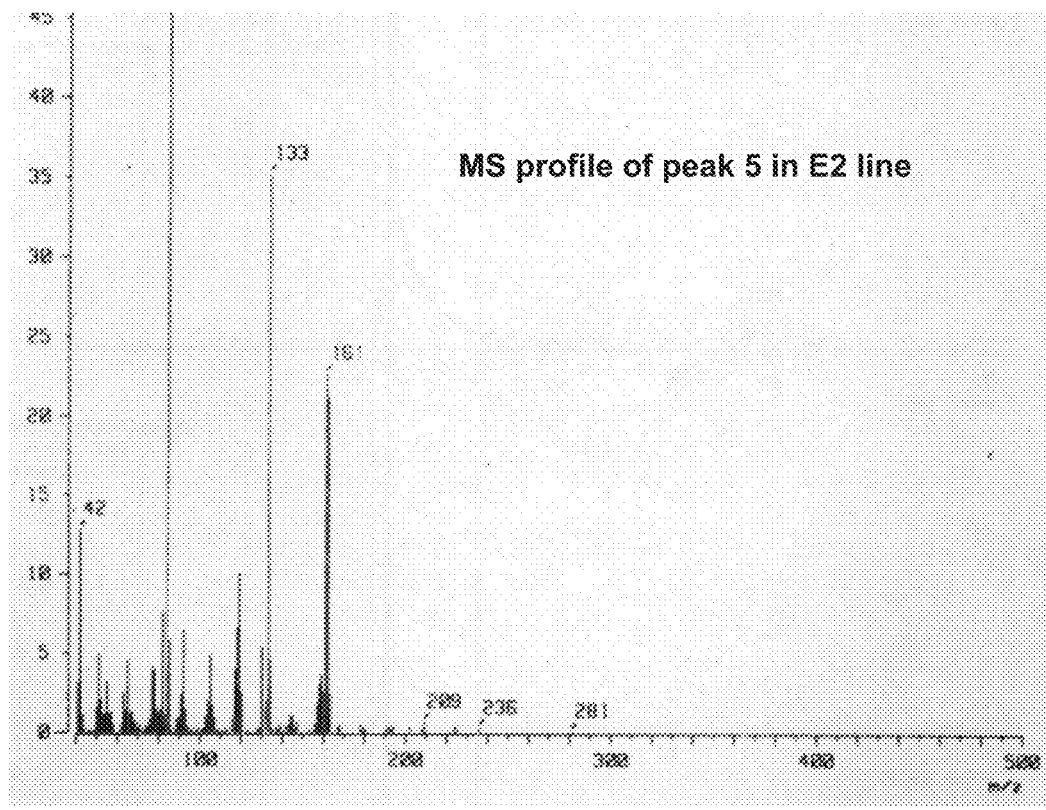
FIG. 10: MS profile of nicotine synthesized in *A. belladonna* hairy roots expressing A622 and NBB1
Figure 10:
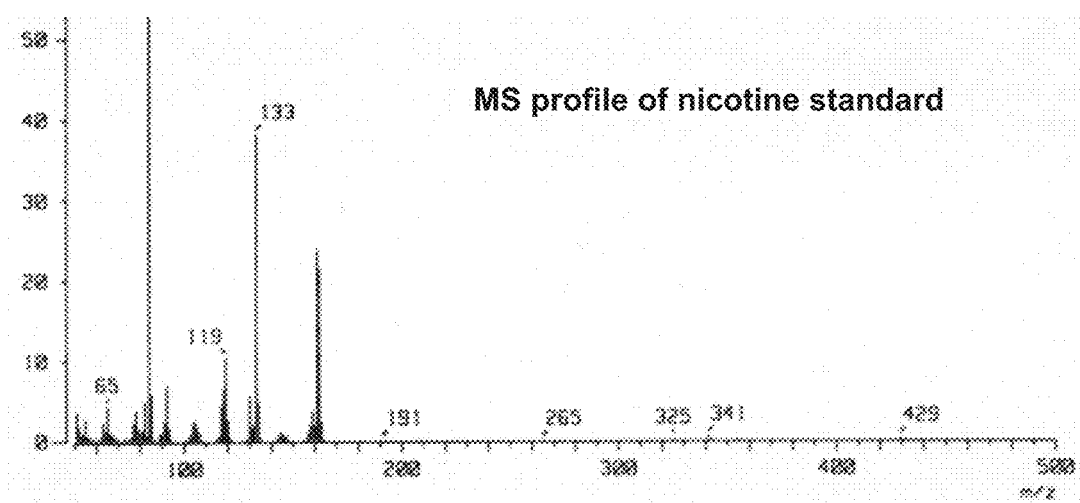

A small but distinct novel peak was detected (See peak 5 in FIG. 9). A peak corresponding to the peak 5 was not detectable in the WT line hairy roots. The compound of peak 5 showed an MS fragmentation profile identical to that of nicotine, as shown in FIG. 10. This demonstrated that expression of exogenous NBB1 and A622 are sufficient for nicotine formation in *A. belladonna* hairy roots.

Figure 11A:
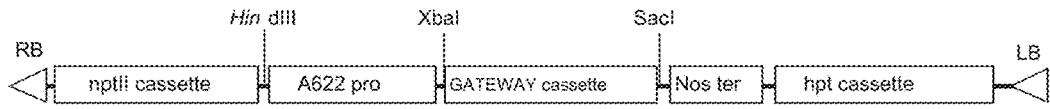
FIG. 11A: T-DNA region of pA622pro-DEST

Example 9: Increasing Nicotine Content by Expression of PMT Under Control of the A622 Promoter Description of pA622pro-DEST pA622pro-DEST has the NPTII gene expression cassette and the HPT gene expression cassette as selection markers. An A622 promoter of 1,407 bp was amplified using a vector containing the A622 promoter (Shoji et al., *Plant Mol. Biol.* 50, 427-440 (2002)) as the template and the A622 promoter-specific primers shown below, and digested with HindIII and XbaI. The resultant fragment was cloned between the HindIII and XbaI sites in pBI101H. The binary vector was converted into a GATEWAY destination vector after the GATEWAY cassette containing attR recombination sites flanking a ccdB gene and a chloramphenicol-resistance gene were cloned between the XbaI and SacI sites in the binary vector. See FIG. 11A.

```
A622 promoter-specific primers
A622pro-01F
                                    (SEQ ID NO: 23)
5' AAAAGCTTAGATCTCTCTTATGTTTCATG
HindIII site is underlined.

A622pro-02R
                                    (SEQ ID NO: 24)
5' TCTAGATTTACTCCTAGGGGAAGAAAAAAGTAGC
```

Preparation of PMT Overexpression Construct

An attB-PMT fragment was amplified using the tobacco PMT vector in which PMT ORF (NCBI accession number; D28506) was cloned in the BstXI site of pcDNAII (Invitrogen) (See SEQ ID NO: 12) as the template, the gene-specific primers below, and attB sequence adapter primers, as described above in Example 4. A GATEWAY entry clone pDONR221-PMT was created by a BP recombination reaction between the attB-PMT PCR product and pDONR221 (Invitrogen).

```
Gene-specific primers
PMT-attB1
                                    (SEQ ID NO: 25)
          5' AAAAAGCAGGCTCAAAAATGGAAGTCATATC PMT-attB2
                                    (SEQ ID NO: 26)
          5' AGAAAGCTGGGTTTAAGACTCGATCATACTTC
```

Figure 11B:
FIG. 11B: T-DNA region of pA622pro-PMTox

The PMT ORF was transferred from the pDONR221-PMT vector to the GATEWAY binary vector pA622pro-DEST by an LR reaction. The gene expression vector was referred to as pA622pro-PMTox. See FIG. 11B.

Production of Transgenic Tobacco Plants pA622pro-PMTox was transformed into *Agrobacterium tumefaciens* strain EHA105, which was used to transform wild-type K326 leaves. Transgenic T0 shoots were regenerated, and were transferred to the rooting medium. Several rooted transgenic plants were transferred to soil.

Alkaloid Analysis

Figure 12:
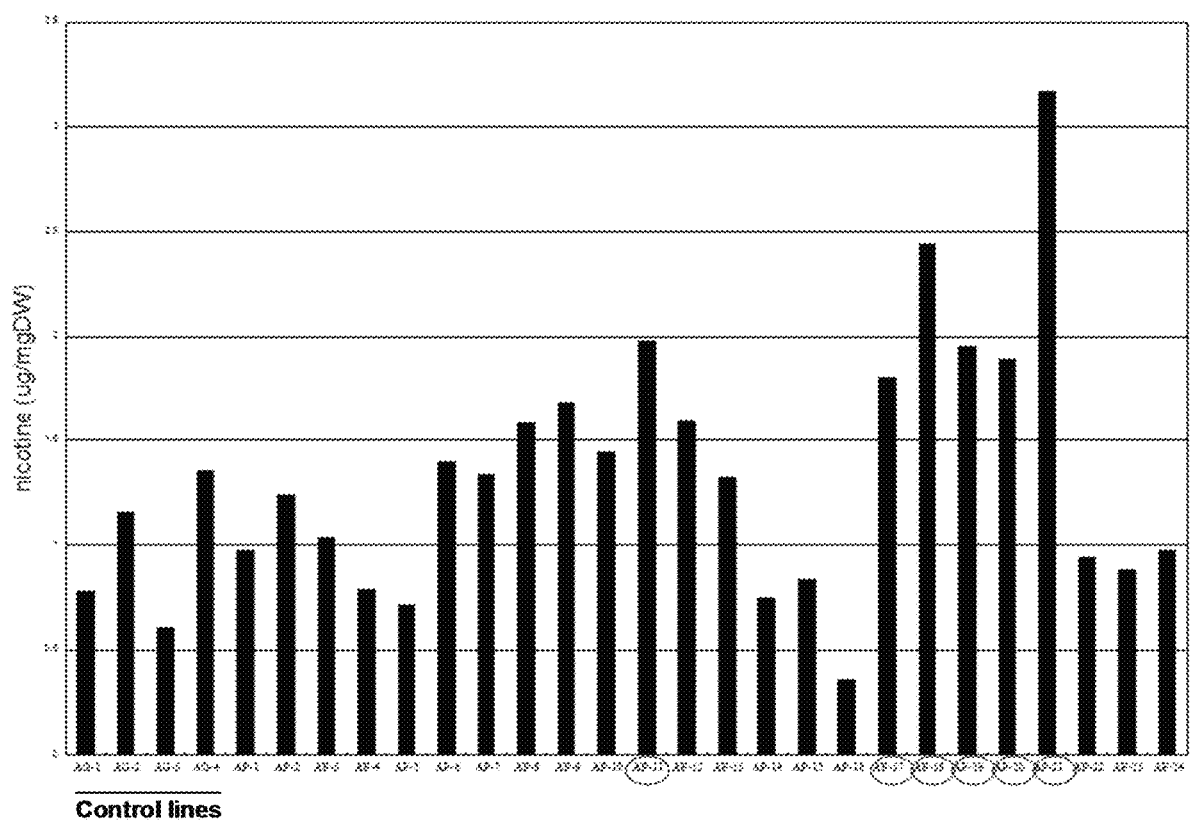
FIG. 12: Nicotine content in leaf of tobacco plants transformed with A622pro-PMTox (AP-1 to AP-24). AG-1 to AG-4 are control plants transformed with A622-GUS

Alkaloids were extracted from the transgenic tobacco leaves and analyzed, as described above in Example 4. The nicotine content in leaves of plants sampled 36 days after transfer to soil was analyzed. Several transgenic lines transformed with pA622pro-PMTox showed greater nicotine accumulation than the control lines, in which wild-type K326 plants were transformed with the AG-GUS cassette. See FIG. 12.

Figure 11C:
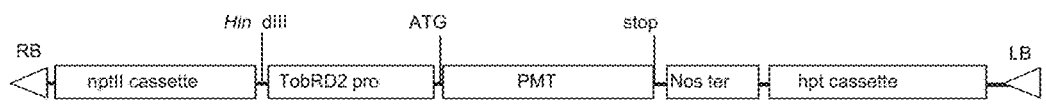
FIG. 11C: T-DNA region of pTobRD2-PMTox

Example 10: Increasing Nicotine Content by Expression of PMT Under Control of the TobRD2 Promoter Preparation of PMT Overexpression Construct The PMT ORF was transferred from the pDONR221-PMT vector to the GATEWAY binary vector pTobRD2-DEST (see FIG. 4A) by an LR reaction. The gene expression vector was referred to as pTobRD2-PMTox. See FIG. 11C.

Production of Transgenic Tobacco Plants pTobRD2-PMTox was transformed into *Agrobacterium tumefaciens* strain EHA105, which was used to transform wild-type K326 leaves. Transgenic T0 shoots were regenerated, and were transferred to the rooting medium. Several rooted transgenic plants were transferred to soil.

Alkaloid Analysis

Alkaloids were extracted from the transgenic tobacco leaves and analyzed, as described above in Example 4. The nicotine content in leaves of plants sampled 36 days after transfer to soil was analyzed. Several transgenic lines showed greater nicotine accumulation than the control lines, in which wild-type K326 plants were transformed with a TobRD2-GUS cassette. See FIG. 13.

Example 11: Increasing Nicotine Content by Expression of QPT Under Control of the A622 Promoter Preparation of QPT Overexpression Construct The QPT ORF fragment (SEQ ID NO: 11) was amplified using the pBJY6 vector (supplied from Dr. Kenzo Nakamura, Nagoya University, Japan) as the template and the gene-specific primers shown below. A GATEWAY entry clone pENTR-QPT was created by a TOPO cloning reaction.

```
QPT Gene-specific primers
QPT-F
                               (SEQ ID NO: 27)
       5' CACCATGTTTAGAGCTATTCC QPT-R
                               (SEQ ID NO: 28)
       5' TCATGCTCGTTTTGTACGCC
```

Figure 11D:
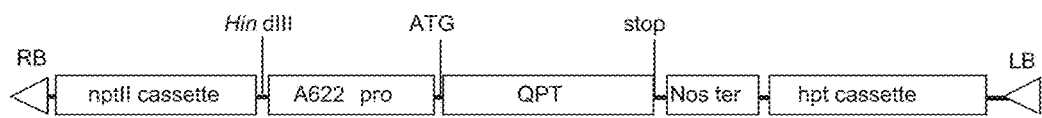
FIG. 11D: T-DNA region of pA622pro-QPTox

The QPT ORF was transferred from the pENTR-QPT vector to the GATEWAY binary vector pA622pro-DEST (see FIG. 11A) by an LR reaction. The gene expression vector was referred to as pA622pro-QPTox. See FIG. 11D.

Production of Transgenic Tobacco Plants pA622pro-QPTox was transformed into *Agrobacterium tumefaciens* strain EHA105, which was used to transform wild-type K326 leaves. Transgenic T0 shoots were regenerated, and were transferred to the rooting medium. Several rooted transgenic plants were transferred to soil.

Analyzing Alkaloids

Figure 14:
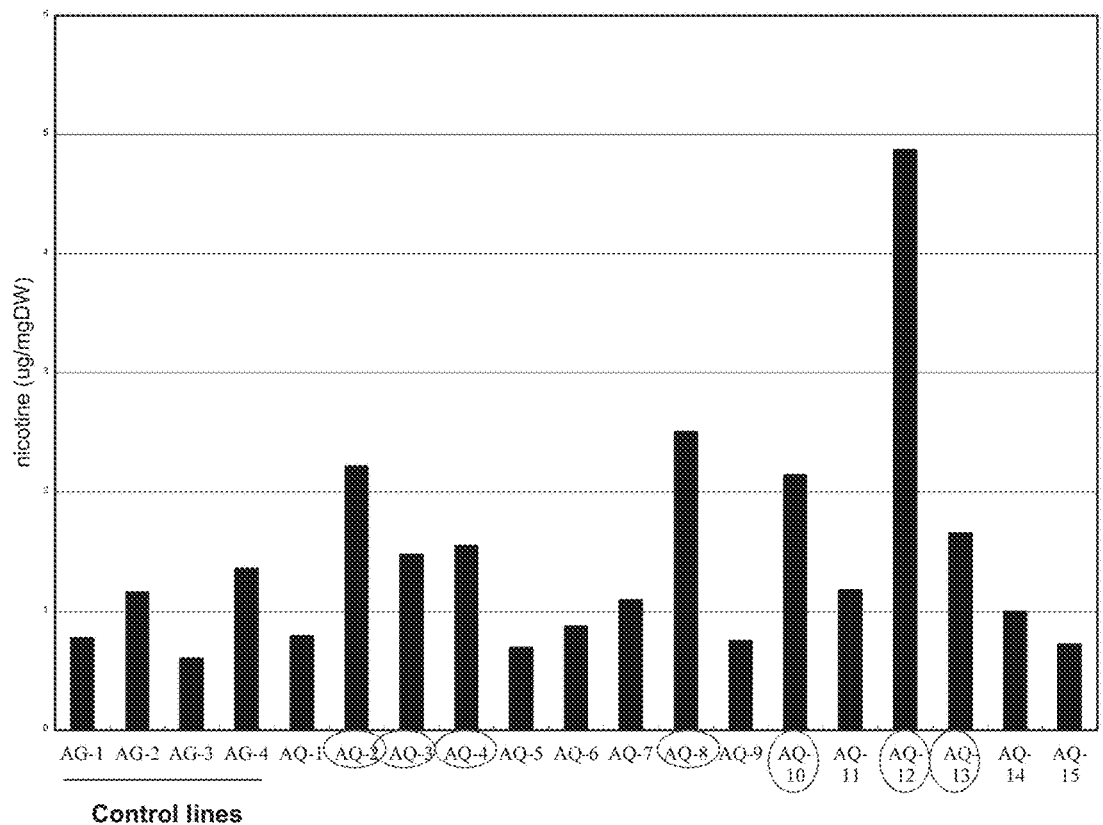
FIG. 14: Nicotine content in leaf of tobacco plants transformed with A622pro-QPTox (AQ-1 to AQ-15). AG-1 to AG-4 are control plants transformed with A622-GUS

Alkaloids were extracted from the transgenic tobacco leaves and analyzed, as described above in Example 4. The nicotine content in leaves of plants sampled 36 days after transfer to soil was analyzed. Several transgenic lines showed greater nicotine accumulation than the control lines, in which wild-type K326 plants were transformed with an A622-GUS cassette. See FIG. 14.

Figure 11E:
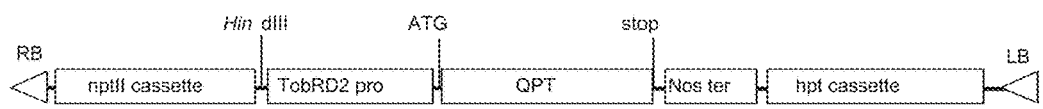
FIG. 11E: T-DNA region of pTobRD2-QPTox

Example 12: Increasing Nicotine Content by Expression of QPT Under Control of the TobRD2 Promoter Preparation of QPT Overexpression Construct The QPT ORF was transferred from the pDONR221-QPT vector to a GATEWAY binary vector pTobRD2-DEST (see FIG. 4A) by an LR reaction. The gene expression vector was referred to as pTobRD2-QPTox. See FIG. 11E.

Production of Transgenic Tobacco Plants pTobRD2-QPTox was transformed into *Agrobacterium tumefaciens* strain EHA105, which was used to transform wild-type K326 leaves. Transgenic T0 shoots were regenerated, and were transferred to the rooting medium. Several rooted transgenic plants were transferred to soil.

Analyzing Alkaloids

Figure 15:
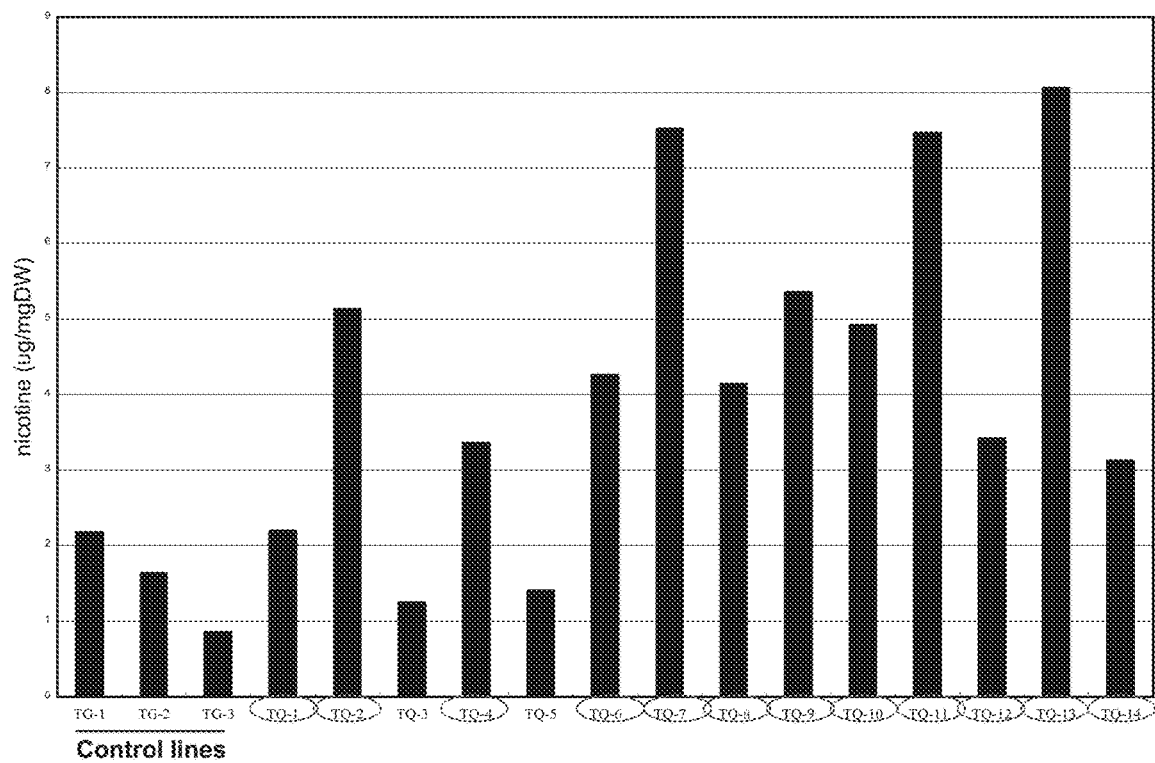
FIG. 15: Nicotine content in leaf of tobacco plants transformed with TobRD2-QPTox (TQ-1 to TQ-14). TG-1 to TG-3 are control plants transformed with TobRD2-GUS

Alkaloids were extracted from the transgenic tobacco leaves and analyzed, as described above in Example 4. The nicotine content in leaves of plants sampled 36 days after transfer to soil was analyzed. Several transgenic lines showed greater nicotine accumulation than the control lines, in which wild-type K326 plants were transformed with a TobRD2-GUS cassette. See FIG. 15.

Example 13: Increasing Nicotine Content by Expression of PMT and QPT Under Control of the A622 Promoter Description of pBI221-A622pro-DEST pBI221-A622pro-DEST was the basic vector for construction of multi-gene expression binary vector. An A622 promoter of 1,407 bp was amplified using the pUC19-A622profull-LUC vector as the template and the A622 promoter-specific primers, and digested with HindIII and XbaI. The resultant fragment was cloned between HindIII and XbaI sites in pBI221 (Clontech), which replaced the CaMV 35S promoter with the A622 promoter. The vector was converted into a GATEWAY destination vector after the GATEWAY cassette containing attR recombination sites flanking a ccdB gene and a chloramphenicol-resistance gene was cloned between the XbaI and SacI sites in the vector, which replaced the B-glucuronidase gene with the GATEWAY cassette. Then, an HindIII-EcoRI adapter was inserted into the EcoRI site at the 3' end of Nos terminator resulting in pBI221-A622pro-DEST.

Preparation of PMT-QPT Overexpression Construct

Figure 11F:
FIG. 11F: T-DNA region of pA622pro-PMTox-QPTox

In order to overexpress both PMT and QPT proteins, the A622pro-PMT expression cassette and the A622pro-QPT expression cassette were cloned in tandem in a binary vector. First, the PMT ORF was transferred from the pDONR221-PMT vector to the GATEWAY binary vector pBI221-A622pro-DEST by an LR reaction. The gene expression vector was referred to as pBI221-A622pro-PMT. The pBI221-A622pro-PMT was digested with HindIII, and then cloned into the HindIII site at the 5' end of A622 promoter of the pA622pro-QPTox vector. The resultant PMT-QPT expression vector was referred to as pA622pro-PMTox-QPTox. A diagram of the T-DNA region of pA622pro-PMTox-QPTox is shown in FIG. 11F.

Production of Transgenic Tobacco Plants pA622pro-PMTox-QPTox was transformed into *Agrobacterium tumefaciens* strain EHA105, which was used to transform wild-type K326 leaves. Transgenic T0 shoots were regenerated, and were transferred to the rooting medium. Several rooted transgenic plants were transferred to soil.

Procedure for Analysis of Alkaloid Levels

Alkaloids were extracted from the transgenic tobacco leaves and analyzed, as described above in Example 4. The nicotine content in leaves of plants sampled 36 days after transfer to soil was analyzed. Several lines transformed with A622pro-PMTox-QPTox showed greater nicotine accumulation than the control lines, in which wild-type K326 plants were transformed with an A622-GUS cassette. See FIG. 16.

Figure 11G:
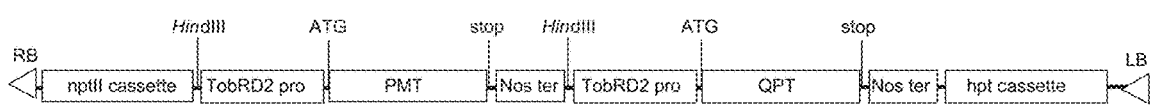
FIG. 11G: T-DNA region of pTobRD2-PMTox-QPTox

Example 14: Increasing Nicotine Content by Expression of PMT and QPT Under Control of the TobRD2 Promoter Preparation of PMT-QPT Overexpression Construct In order to overexpress both PMT and QPT proteins under control of the TobRD2, the TobRD2-PMT expression cassette and the TobRD2-QPT expression cassette were cloned in tandem in a binary vector. First, the PMT ORF was transferred from the pDONR221-PMT vector to a GATEWAY binary vector pBI221-TobRD2-DEST by an LR reaction. The gene expression vector was referred to as pBI221-TobRD2-PMT. The pBI221-TobRD2-PMT was digested with HindIII, and then cloned into the HindIII site at the 5' end of TobRD2 promoter in pTobRD2-QPTox. The resultant PMT-QPT expression vector was referred to as pTobRD2-PMTox-QPTox. See FIG. 11G.

Production of Transgenic Tobacco Plants pTobRD2-PMTox-QPTox was transformed into *Agrobacterium tumefaciens* strain EHA105, which was used to transform wild-type K326 leaves. Transgenic T0 shoots were regenerated, and were transferred to the rooting medium. Several rooted transgenic plants were transferred to soil.

Procedure for Analysis of Alkaloid Levels

Alkaloids were extracted from the transgenic tobacco leaves and analyzed, as described above in Example 4. The nicotine content in leaves of plants sampled 36 days after transfer to soil was analyzed. Several transgenic lines transformed with the TobRD2-PMTox-QPTox showed greater nicotine accumulation than the control lines, wild-type K326 plants transformed with a TobRD2-GUS cassette. See FIG. 17.

Example 15: Production of Nicotinic Alkaloids in *Arabidopsis* by Expression of NBB1 in Combination with Additional Alkaloid Biosynthetic Enzymes

*Arabidopsis* plants do not produce nicotinic alkaloids. However, a precursor of a number of nicotinic alkaloids, nicotinic acid, is a common metabolite. The effect of expressing both NBB1 and A622 together in *Arabidopsis* was tested. Because nicotine is an alkaloid of particular interest, expression of PMT was included to increase the availability of methylputrescine, a precursor of the pyrrolidine ring in nicotine.

Preparation of A622 Overexpression Construct

Tobacco A622 cDNA, which contains an introduced NcoI site at the first ATG (Hibi et al., 1994), was excised from pcDNAII (Invitrogen) as an NcoI-BamHI fragment and cloned into pRTL2 (Restrepo et al., *Plant Cell* 2:987-98 (1990)) under control of the CaMV35S promoter with a duplicated enhancer. This A622 overexpression cassette was excised with HindIII and cloned in a binary vector pGA482 (Amersham) to produce the A622 expression vector pGA-A622.

Production of Transgenic 35S A622 Plants

The binary vector pGA-A622 was introduced to *A. tumefaciens* strain LBA4404 by electroporation. *A. thaliana* plants (ecotype: Wassilewskija (WS)) were transformed by *A. tumefaciens* using a callus induction-plant regeneration method, basically as described by Akama et al., *Plant cell Reports* 12: 7-11 (1992). Kanamycin resistance (50 mg/L on Shoot-Induction medium) was used as a selection marker for the pGA-A622 transformation. Transgenic plants were regenerated from the callus, grown at 23° C. under 16 h light/8 h dark condition in a growth chamber.

Preparation of NBB1- and PMT-Overexpression Construct

Figure 18A:
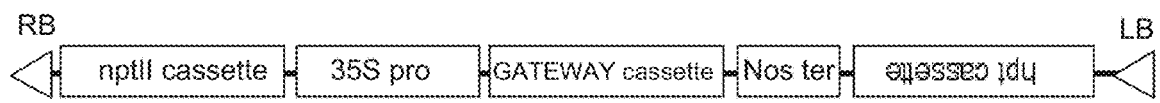
FIG. 18A: T-DNA region of pGWB2
Figure 18B:
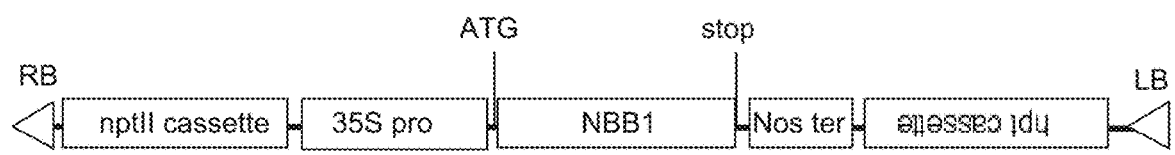
FIG. 18B: T-DNA region of p35S-NBB1
Figure 18C:
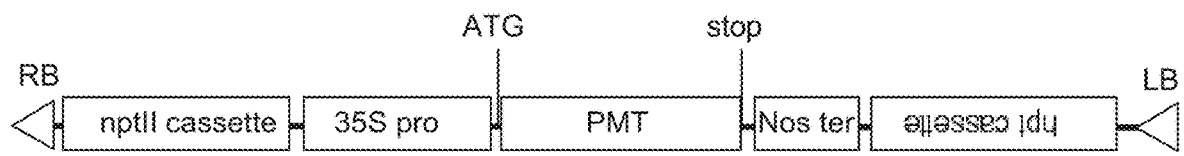
FIG. 18C: T-DNA region of p35S-NBB1

NBB1 ORF (SEQ ID NO: 9) was transferred from the pDONR221-NBB1-2 vector to a GATEWAY binary vector pGWB2 (see FIG. 18A) by LR reaction. The gene expression vector, in which NBB1 is linked to the CAMV 35S promoter, is referred to as p35S-NBB1. See FIG. 18B. Similarly, PMT ORF was transferred from the pDONR221-PMT vector to the pGWB2 by LR reaction. The gene expression vector is referred to as p35S-PMT See FIG. 18C.

Production of Transgenic 35S-A622-35S-NBB1 Plants, 35S-A622-35S-PMT Plants and 35S-A622-35S-NBB1-35S-PMT Plants The binary vectors p35S-NBB1 and p35S-PMT were introduced to *A. tumefaciens* strain EHA105 by electroporation. T1 generation plants carrying pGA-A622 were transformed by *A. tumefaciens* using a floral dip method, basically as described by Clough et al., *Plant J.* 16: 735-43 (1998). Hygromycin resistance (25 mg/L on Shoot-Induction medium) was used as a selection marker for the p35S-NBB1 and p35S-PMT transformations. Transgenic plants were grown at 23° C. under 16 h light/8 h dark condition in a growth chamber. Resultant transgenic plants were screened by genomic PCR using the 35S promoter primers and NBB1- or PMT-gene specific primers.

```
Primers for screening the 35S-A622-35S-NBB1 plants
35S-F
                                        (SEQ ID NO: 29)
             5' ACCCTTCCTCTATATAAGGAAG NBB1-1140
                                        (SEQ ID NO: 30)
             5' TGAGCCCAAGCTGTTTCAGAATCC Primers for screening the 35S-A622-35S-PMT plants
35S-F
                                        (SEQ ID NO: 31)
             5' ACCCTTCCTCTATATAAGGAAG PMT-01R
                                        (SEQ ID NO: 32)
             5' CGCTAAACTCTGAAAACCAGC
```

The PCR positive 35S-A622-35S-NBB1 plants and 35S-A622-35S-PMT plants were crossed to produce 35S-A622-35S-NBB1-35S-PMT plants. F1 progeny were screened by genomic PCR using each expression cassette specific primer pair.

Total proteins were extracted from the PCR-positive lines. Frozen roots were immediately homogenized in extraction buffer (100 mM Tris-HCl pH6.8, 4% SDS, 20% glycerol) containing 1 mM phenylmethyl sulfonyl fluoride and 200 mM dithiothreitol using mortar and pestle. After centrifugation of the homogenates, soluble proteins in the supernatant were separated by SDS-PAGE. Immunoblot analysis was performed using anti-A622 mouse serum for A622 protein detection and anti-NBB1 rabbit serum for NBB1 protein detection as described in Shoji et al., *Plant Mol. Biol.*

Figure 19:
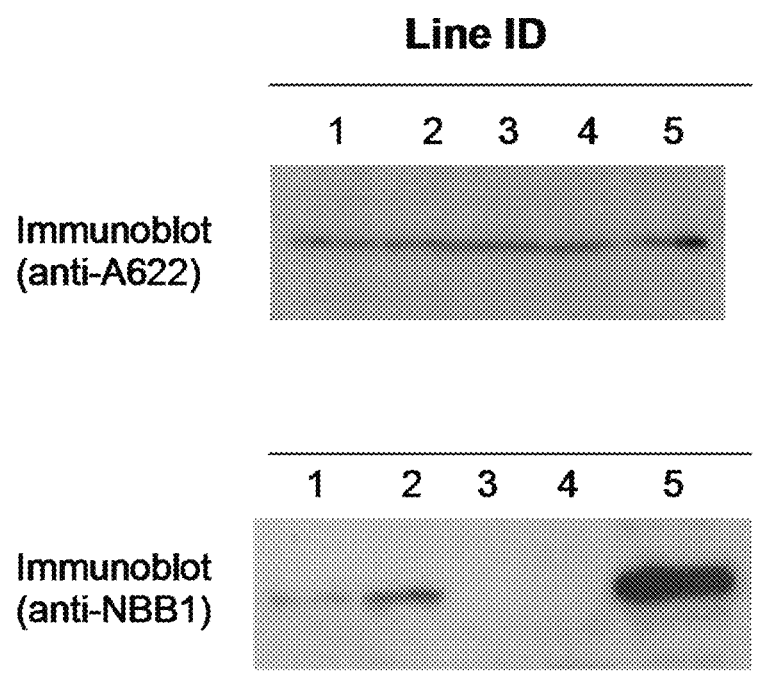
FIG. 19: Immunoblot analysis of *Arabidopsis thaliana* lines transformed with 35S-A622-35S-NBB1-35S-PMT cassettes.

50: 427-40 (2002). Transgenic lines expression were obtained that contain both A622 and NBB1 polypeptides. See FIG. 19.

Procedure for Analyzing Alkaloid Levels

Figure 20:
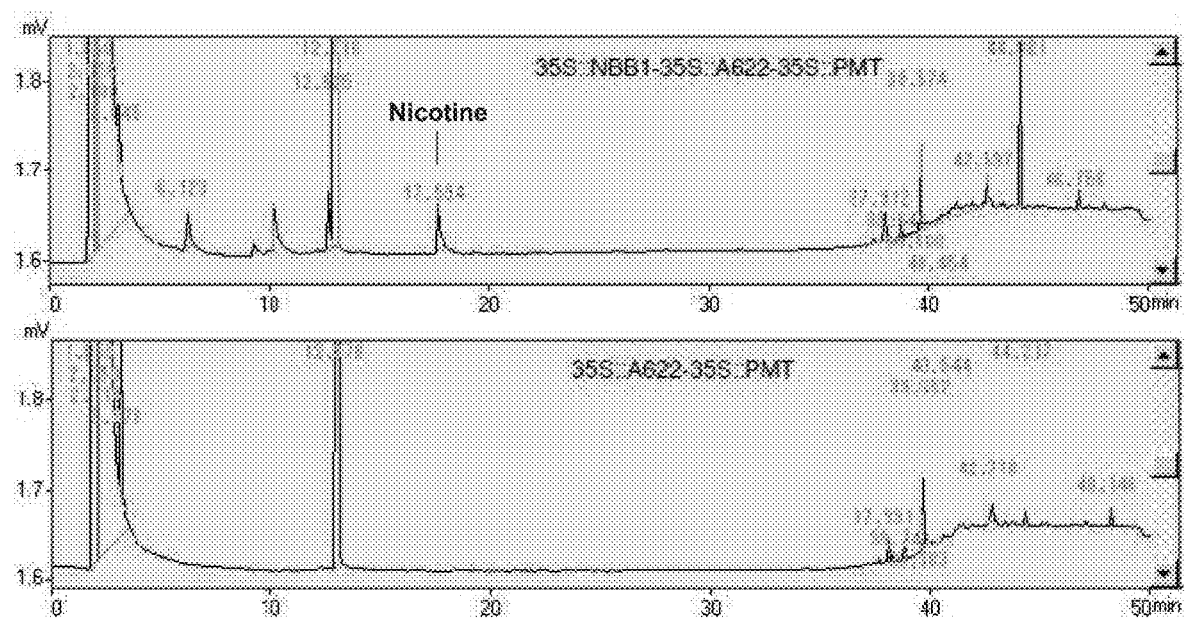
FIG. 20: Transgenic *Arabidopsis* co-expressing NBB1, A622, and PMT.

Transgenic lines expressing NBB1 and A622 were selected and used for the alkaloid analysis. Alkaloids were extracted from the transgenic tobacco leaves and analyzed, as described above in Example 4. As shown in FIG. 20, a new peak corresponding to the elution time of nicotine was found in the NBB1-A622-PMT line but not in the A622-PMT line. This shows that expression of NBB1 and A622 together is more effective than expression of A622 alone for production of nicotinic alkaloids in a plant that does not normally produce alkaloids.

Example 16: Expression of NBB1 and A622 in Non-Plant Cells

Figure 21A:
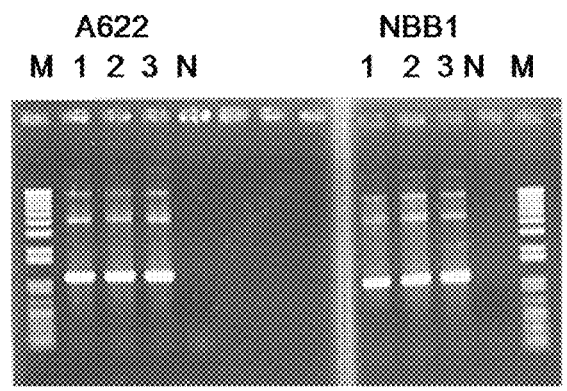
FIG. 21A: Confirmation of the presence of A622 and NBB1 in recombinant bacmids

The Bac-to-Bac Expression System (Invitrogen) insect cell-baculovirus expression system was used to express NBB1 and A622 proteins with 6×His tags (SEQ ID NO: 34) in insect cells. In order to make the expression clone, NBB1 and A622 ORFs (SEQ ID NO: 9 and 10, respectively) were transferred from respective DONR vectors (pDONR-NBB1-2, pDONR-A622) to the GATEWAY vector pDEST10 (Invitrogen) by LR reactions. Resultant expression clones were referred to as pDEST1O-NBB1 and pDEST10-A622.

pDEST10-NBB1 and pDEST10-A622 were transformed into MAX Efficiency DH10Bac Cells (Invitrogen), to recover the recombinant bacmid DNAs. PCR analysis using a gene specific primer and an M13 reverse primer was used to verify the presence of recombinant bacmids containing A622 and NBB1. See FIG. 21A.

Resultant recombinant bacmids containing respective gene expression cassettes were transfected to the insect cell Sf9 with Cellfectin (Invitrogen). The Sf9 cells were infected with the virus stocks in two rounds to amplify and scale-up the virus.

Figure 21B:
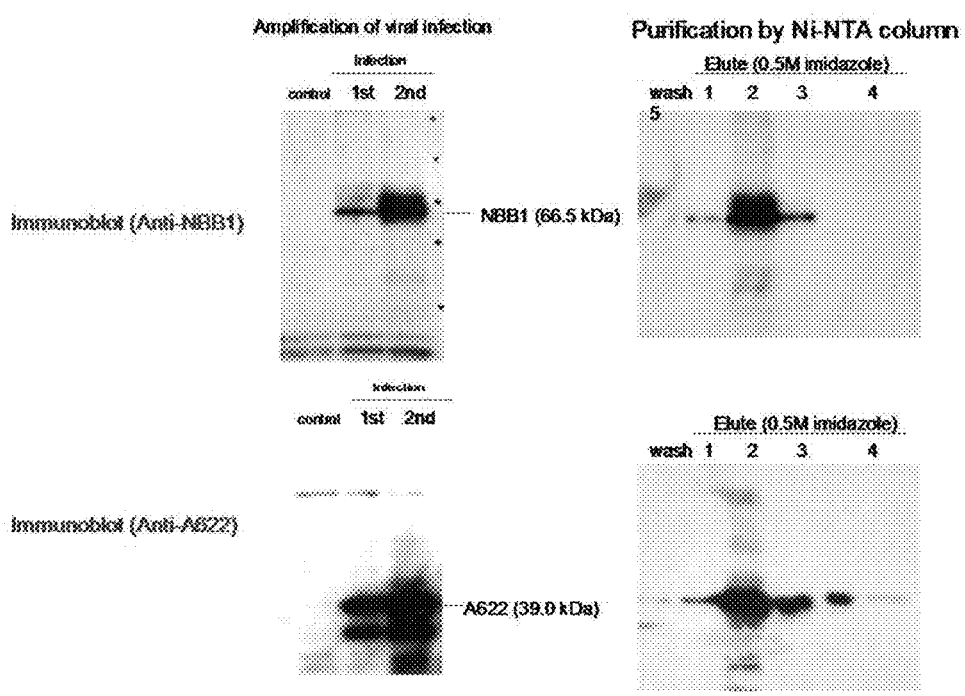
FIG. 21B: Detection of A622 and NBB1 in insect cell Sf9 cells and Ni-NTA column eluates

NBB1 and A622 were produced in the insect cell cultures, as shown by immunoblotting with anti-NBB1 and anti-A622 antisera. The recombinant proteins containing the 6×His tag were purified by adsorption on Ni-NTA columns followed by elution with 0.5 M imidazole. See FIG. 21B.

```
                              Sequence Listing

SEQ ID NO: 1
(NBB1 polynucleotide)
ACGCGGGGAGAAATACATACAACATGTTTCCGCTCATAATTCTGATCAGCTTTTCACTTGCTTCCTTGTCTGAAACTGCTACTGG
AGCTGTTACAAATCTTTCAGCCTGCTTAATCAACCACAATGTCCATAACTTCTCTATTTACCCCACAAGTAGAAATTACTTTAAC
TTGCTCCACTTCTCCCTTCAAAATCTTCGCTTTGCTGCACCTTTCATGCCGAAACCAACCTTCATTATCCTACCAAGCAGTAAGG
AGGAGCTCGTGAGCACCATTTTTTGTTGCAGAAAAGCATCTTATGAAATCAGAGTAAGGTGCGGCGGACACAGTTACGAAGGAAC
TTCTTACGTTTCCTTTGACGCTTCTCCATTCGTGATCGTTGACTTGATGAAATTAGACGACGTTTCAGTAGATTTGGATTCTGAA
ACAGCTTGGGCTCAGGGCGGCGCAACAATTGGCCAAATTTATTATGCCATTGCCAAGGTAAGTGACGTTCATGCATTTTCAGCAG
GTTCGGGACCAACAGTAGGATCTGGAGGTCATATTTCAGGTGGTGGATTTGGACTTTTATCTAGAAAATTCGGACTTGCTGCTGA
TAATGTCGTTGATGCTCTTCTTATTGATGCTGATGGACGGTTATTAGACCGAAAAGCCATGGGCGAAGACGTGTTTTGGGCAATC
AGAGGTGGCGGCGGTGGAAATTGGGGCATTGTTTATGCCTGGAAAATTCGATTACTCAAAGTGCCTAAAATCGTAACAACTTGTA
TGATCTATAGGCCTGGATCCAAACAATACGTGGCTCAAATACTTGAGAAATGGCAAATAGTTACTCCAAATTTGGTCGATGATTT
TACTCTAGGAGTACTGCTGAGACCTGCAGATCTACCCGCGGATATGAAATATGGTAATACTACTCCTATTGAAATATTTCCCCAA
TTCAATGCACTTTATTTGGGTCCAAAAACTGAAGTTCTTTCCATATCGAATGAGACATTTCCGGAGCTAGGCGTTAAGAATGATG
AGTGCAAGGAAATGACTTGGGTAGAGTCAGCACTTTTCTTCTCCGAATTAGCTGACGTTAACGGGAACTCGACTGGTGATATCTC
CCGTCTGAAAGAACGTTACATGGACGGAAAAGGTTTTTTCAAAGGCAAAACGGACTACGTGAAGAAGCCAGTTTCAATGGATGGG
ATGCTAACATTTCTTGTGGACTCGAGAAAAACCCGAAGGGATATCTTGTCTTTGATCCTTATGGCGGAGCCATGGACAAGATTA
GTGATCAAGCTATTGCTTTCCCTCATAGAAAAGGTAACCTTTTCGCGATTCAGTATCTAGCACAGTGGAATGAAGAGGACGATTA
CATGAGCGACGTTTACATGGAGTGGATAAGAGGATTTTACAATACAATGACGCCCTTTGTTTCAAGCTCGCCAAGGGGAGCTTAT
ATCAACTACTTGGATATGGATCTTGGAGTGAATATGGTCGACGACTACTTATTGCGAAATGCTAGTAGCAGTAGTCCTTCTTCCT
CTGTTGATGCTGTGGAGAGAGCTAGAGCGTGGGGTGAGATGTATTTCTTGCATAACTATGATAGGTTGGTTAAAGCTAAGACACA
AATTGATCCACTAAATGTTTTTCGACATGAACAGAGTATTCCTCCTATGCTTGGTTCAACGCAAGAGCACAAGTATAGCAGTGAA
TGAGATTTAAAATGTACTACCTTGAGAGAGATTCCGTTGTTAGTTTTCC SEQ ID NO: 1B
(NBB1 ORF sequence used for vector construction)
ATGTTTCCGCTCATAATTCTGATCAGCTTTTCACTTGCTTCCTTGTCTGAAACTGCTACTGGAGCTGTTACAAATCTTTCAGCCT
GCTTAATCAACCACAATGTCCATAACTTCTCTATTTACCCCACAAGTAGAAATTACTTTAACTTGCTCCACTTCTCCCTTCAAAA
TCTTCGCTTTGCTGCACCTTTCATGCCGAAACCAACCTTCATTATCCTACCAAGCAGTAAGGAGGAGCTCGTGAGCACCATTTTT
TGTTGCAGAAAAGCATCTTATGAAATCAGAGTAAGGTGCGGCGGACACAGTTACGAAGGAACTTCTTACGTTTCCTTTGACGCTT
CTCCATTCGTGATCGTTGACTTGATGAAATTAGACGACGTTTCAGTAGATTTGGATTCTGAAACAGCTTGGGCTCAGGGCGGCGC
AACAATTGGCCAAATTTATTATGCCATTGCCAAGGTAAGTGACGTTCATGCATTTTCAGCAGGTTCGGGACCAACAGTAGGATCT
GGAGGTCATATTTCAGGTGGTGGATTTGGACTTTTATCTAGAAAATTCGGACTTGCTGCTGATAATGTCGTTGATGCTCTTCTTA
TTGATGCTGATGGACGGTTATTAGACCGAAAAGCCATGGGCGAAGACGTGTTTTGGGCAATCAGAGGTGGCGGCGGTGGAAATTG
GGGCATTGTTTATGCCTGGAAAATTCGATTACTCAAAGTGCCTAAAATCGTAACAACTTGTATGATCTATAGGCCTGGATCCAAA
CAATACGTGGCTCAAATACTTGAGAAATGGCAAATAGTTACTCCAAATTTGGTCGATGATTTTACTCTAGGAGTACTGCTGAGAC
CTGCAGATCTACCCGCGGATATGAAATATGGTAATACTACTCCTATTGAAATATTTCCCCAATTCAATGCACTTTATTTGGGTCC
AAAAACTGAAGTTCTTTCCATATCGAATGAGACATTTCCGGAGCTAGGCGTTAAGAATGATGAGTGCAAGGAAATGACTTGGGTA
GAGTCAGCACTTTTCTTCTCCGAATTAGCTGACGTTAACGGGAACTCGACTGGTGATATCTCCCGTCTGAAAGAACGTTACATGG
ACGGAAAAGGTTTTTTCAAAGGCAAAACGGACTACGTGAAGAAGCCAGTTTCAATGGATGGGATGCTAACATTTCTTGTGGAACT
CGAGAAAAACCCGAAGGGATATCTTGTCTTTGATCCTTATGGCGGAGCCATGGACAAGATTAGTGATCAAGCTATTGCTTTCCCT
CATAGAAAAGGTAACCTTTTCGCGATTCAGTATCTAGCACAGTGGAATGAAGAGGACGATTACATGAGCGACGTTTACATGGAGT
GGATAAGAGGATTTTACAATACAATGACGCCCTTTGTTTCAAGCTCGCCAAGGGGAGCTTATATCAACTACTTGGATATGGATCT
TGGAGTGAATATGGTCGACGACTACTTATTGCGAAATGCTAGTAGCAGTAGTCCTTCTTCCTCTGTTGATGCTGTGGAGAGAGCT
AGAGCGTGGGGTGAGATGTATTTCTTGCATAACTATGATAGGTTGGTTAAAGCTAAGACACAAATTGATCCACTAAATGTTTTTC
GACATGAACAGAGTATTCCTCCTATGCTTGGTTCAACGCAAGAGCACAAGTATAGCAGTAATGA SEQ ID NO: 2
(NBB1 polypeptide)
MFPLIILISFSLASLSETATGAVTNLSACLINHNVHNFSIYPTSRNYFNLLHFSLQNLRFAAPFMPKPTFIILPSSKEELVSTIF
CCRKASYEIRVRCGGHSYEGTSYVSFDASPFVIVDLMKLDDVSVDLDSETAWAQGGATIGQIYYAIAKVSDVHAFSAGSGPTVGS
```

```
GGHISGGGFGLLSRKFGLAADNVVDALLIDADGRLLDRKAMGEDVFWAIRGGGGGNWGIVYAWKIRLLKVPKIVTTCMIYRPGSK
QYVAQILEKWQIVTPNLVDDFTLGVLLRPADLPADMKYGNTTPIEIFPQFNALYLGPKTEVLSISNETFPELGVKNDECKEMTWV
ESALFFSELADVNGNSTGDISRLKERYMDGKGFFKGKTDYVKKPVSMDGMLTFLVELEKNPKGYLVFDPYGGAMDKISDQAIAFP
HRKGNLFAIQYLAQWNEEDDYMSDVYMEWIRGFYNTMTPFVSSSPRGAYINYLDMDLGVNMVDDYLLRNASSSSPSSSVDAVERA
RAWGEMYFLHNYDRLVKAKTQIDPLNVFRHEQSIPPMLGSTQEHKYSSE

SEQ ID NO: 3
(A622 polynucleotide)
AAAAATCCGATTTAATTCCTAGTTTCTAGCCCCTCCACCTTAACCCGAAGCTACTTTTTTTCTTCCCCTAGGAGTAAAATGGTTG
TATCAGAGAAAAGCAAGATCTTAATAATTGGAGGCACAGGCTACATAGGAAAATACTTGGTGGAGACAAGTGCAAAATCTGGGCA
TCCAACTTTCGCTCTTATCAGAGAAAGCACACTCAAAAACCCCGAGAAATCAAAACTCATCGACACATTCAAGAGTTATGGGGTT
ACGCTACTTTTTGGAGATATATCCAATCAAGAGAGCTTACTCAAGGCAATCAAGCAAGTTGATGTGGTGATTTCCACTGTCGGAG
GACAGCAATTTACTGATCAAGTGAACATCATCAAAGCAATTAAAGAAGCTGGAAATATCAAGAGATTTCTTCCTTCAGAATTTGG
ATTTGATGTGGATCATGCTCGTCAATTGAACCAGCTGCATCACTCTTCGCTCTAAAGGTAAGAATCAGGAGGATGATAGAGGCA
GAAGGAATTCCATACACATATGTAATCTGCAATTGGTTTGCAGATTTCTTCTTGCCCAACTTGGGGCAGTTAGAGGCCAAAACCC
CTCCTAGAGACAAAGTTGTCATTTTTGGCGATGGAAATCCCAAAGCAATATATGTGAAGGAAGAAGACATAGCGACATACACTAT
CGAAGCAGTAGATGATCCACGGACATTGAATAAGACTCTTCACATGAGACCACCTGCCAATATTCTATCCTTCAACGAGATAGTG
TCCTTGTGGGAGGACAAAATTGGGAAGACCCTCGAGAAGTTATATCTATCAGAGGAAGATATTCTCCAGATTGTACAAGAGGGAC
CTCTGCCATTAAGGACTAATTTGGCCATATGCCATTCAGTTTTTGTTAATGGAGATTCTGCAAACTTTGAGGTTCAGCCTCCTAC
AGGTGTCGAAGCCACTGAGCTATATCCAAAAGTGAAATACACAACCGTCGACGAGTTCTACAACAAATTTGTCTAGTTTGTCGAT
ATCAATCTGCGGTGACTCTATCAAACTTGTTGTTTCTATGAATCTATTGAGTGTAATTGCAATAATTTTCGCTTCAGTGCTTTTG
CAACTGAAATGTACTAGCTAGTTGAACGCTAGCTAAATTCTTTACTGTTGTTTTCTATTTTTCGTCTTATTCCA SEQ ID NO: 3B
(A622 ORF sequence used for vector construction)
ATGGTTGTATCAGAGAAAAGCAAGATCTTAATAATTGGAGGCACAGGCTACATAGGAAAATACTTGGTGGAGACAAGTGCAAAAT
CTGGGCATCCAACTTTCGCTCTTATCAGAGAAAGCACACTCAAAAACCCCGAGAAATCAAAACTCATCGACACATTCAAGAGTTA
TGGGGTTACGCTACTTTTTGGAGATATATCCAATCAAGAGAGCTTACTCAAGGCAATCAAGCAAGTTGATGTGGTGATTTCCACT
GTCGGAGGACAGCAATTTACTGATCAAGTGAACATCATCAAAGCAATTAAAGAAGCTGGAAATATCAAGAGATTTCTTCCTTCAG
AATTTGGATTTGATGTGGATCATGCTCGTCAATTGAACCAGCTGCATCACTCTTCGCTCTAAAGGTAAGAATCAGGAGGATGAT
AGAGGCAGAAGGAATTCCATACACATATGTAATCTGCAATTGGTTTGCAGATTTCTTCTTGCCCAACTTGGGGCAGTTAGAGGCC
AAAACCCCTCCTAGAGACAAAGTTGTCATTTTTGGCGATGGAAATCCCAAAGCAATATATGTGAAGGAAGAAGACATAGCGACAT
ACACTATCGAAGCAGTAGATGATCCACGGACATTGAATAAGACTCTTCACATGAGACCACCTGCCAATATTCTATCCTTCAACGA
GATAGTGTCCTTGTGGGAGGACAAAATTGGGAAGACCCTCGAGAAGTTATATCTATCAGAGGAAGATATTCTCCAGATTGTACAA
GAGGGACCTCTGCCATTAAGGACTAATTTGGCCATATGCCATTCAGTTTTTGTTAATGGAGATTCTGCAAACTTTGAGGTTCAGC
CTCCTACAGGTGTCGAAGCCACTGAGCTATATCCAAAAGTGAAATACACAACCGTCGACGAGTTCTACAACAAATTTGTCTAG SEQ ID NO: 4
(A622 polypeptide)
MVVSEKSKILIIGGTGYIGKYLVETSAKSGHPTFALIRESTLKNPEKSKLIDTFKSYGVTLLFGDISNQESLLKAIKQVDVVIST
VGGQQFTDQVNIIKAIKEAGNIKRFLPSEFGFDVDHARAIEPAASLFALKVRIRRMIEAEGIPYTYVICNWFADFFLPNLGQLEA
KTPPRDKVVIFGDGNPKAIYVKEEDIATYTIEAVDDPRTLNKTLHMRPPANILSFNEIVSLWEDKIGKTLEKLYLSEEDILQIVQ
EGPLPLRTNLAICHSVFVNGDSANFEVQPPTGVEATELYPKVKYTTVDEFYNKFV SEQ ID NO: 5
(QPT polynucleotide)
CAAAAACTATTTTCCACAAAATTCATTTCACAACCCCCCCAAAAAAAACCATGTTTAGAGCTATTCCTTTCACTGCTACAGTGC
ATCCTTATGCAATTACAGCTCCAAGGTTGGTGGTGAAAATGTCAGCAATAGCCACCAAGAATACAAGAGTGGAGTCATTAGAGGT
GAAACCACCAGCACACCCAACTTATGATTTAAAGGAAGTTATGAAACTTGCACTCTCTGAAGATGCTGGGAATTTAGGAGATGTG
ACTTGTAAGGCGACAATTCCTCTTGATATGGAATCCGATGCTCATTTTCTAGCAAAGGAAGACGGGATCATAGCAGGAATTGCAC
TTGCTGAGATGATATTCGCGGAAGTTGATCCTTCATTAAAGGTGGAGTGGTATGTAAATGATGGCGATAAAGTTCATAAAGGCTT
GAAATTTGGCAAAGTACAAGGAAACGCTTACAACATTGTTATAGCTGAGAGGGTTGTTCTCAATTTTATGCAAAGAATGAGTGGA
ATAGCTACACTAACTAAGGAAATGGCAGATGCTGCACACCCTGCTTACATCTTGGAGACTAGGAAAACTGCTCCTGGATTACGTT
TGGTGGATAAATGGGCGGTATTGATCGGTGGGGGAAGAATCACAGAATGGGCTTATTTGATATGGTAATGATAAAAGACAATCA
CATATCTGCTGCTGGAGGTGTCGGCAAAGCTCTAAAATCTGTGGATCAGTATTTGGAGCAAAATAAACTTCAAATAGGGGTTGAG
GTTGAAACCAGGACAATTGAAGAAGTACGTGAGGTTCTAGACTATGCATCTCAAACAAAGACTTCGTTGACTAGGATAATGCTGG
ACAATATGGTTGTTCCATTATCTAACGGAGATATTGATGTATCCATGCTTAAGGAGGCTGTAGAATTGATCAATGGGAGGTTTGA
TACGGAGGCTTCAGGAAATGTTACCCTTGAAACAGTACACAAGATTGGACAAACTGGTGTTACCTACATTTCTAGTGGTGCCCTG
ACGCATTCCGTGAAAGCACTTGACATTTCCCTGAAGATCGATACAGAGCTCGCCCTTGAAGTTGGAAGGCGTACAAAACGAGCAT
GAGCGCCATTACTTCTGCTATAGGGTTGGAGTAAAAGCAGCTGAATAGCTGAAAGGTGCAAATAAGAATCATTTTACTAGTTGTC
AAACAAAAGATCCTTCACTGTGTAATCAAACAAAAAGATGTAAATTGCTGGAATATCTCAGATGGCTCTTTTCCAACCTTATTGC
TTGAGTTGGTAATTTCATTATAGCTTTGTTTTCATGTTTCATGGAATTTGTTACAATGAAAATACTTGATTTATAAGTTGGTGT
ATGTAAAATTCTGTGTTACTTCAAATATTTTGAGATGTT SEQ ID NO: 5B
(QPT ORF used for vector construction)
ATGTTTAGAGCTATTCCTTTCACTGCTACAGTGCATCCTTATGCAATTACAGCTCCAAGGTTGGTGGTGAAAATGTCAGCAATAG
CCACCAAGAATACAAGAGTGGAGTCATTAGAGGTGAAACCACCAGCACACCCAACTTATGATTTAAAGGAAGTTATGAAACTTGC
ACTCTCTGAAGATGCTGGGAATTTAGGAGATGTGACTTGTAAGGCGACAATTCCTCTTGATATGGAATCCGATGCTCATTTTCTA
GCAAAGGAAGACGGGATCATAGCAGGAATTGCACTTGCTGAGATGATATTCGCGGAAGTTGATCCTTCATTAAAGGTGGAGTGGT
ATGTAAATGATGGCGATAAAGTTCATAAAGGCTTGAAATTTGGCAAAGTACAAGGAAACGCTTACAACATTGTTATAGCTGAGA
GGGTTGTTCTCAATTTTATGCAAAGAATGAGTGGAATAGCTACACTAACTAAGGAAATGGCAGATGCTGCACACCCTGCTTACATC
TTGGAGACTAGGAAAACTGCTCCTGGATTACGTTTGGTGGATAAATGGGCGGTATTGATCGGTGGGGGAAGAATCACAGAATGG
GCTTATTTGATATGGTAATGATAAAAGACAATCACATATCTGCTGCTGGAGGTGTCGGCAAAGCTCTAAAATCTGTGGATCAGTA
TTTGGAGCAAAATAAACTTCAAATAGGGGTTGAGGTTGAAACCAGGACAATTGAAGAAGTACGTGAGGTTCTAGACTATGCATCT
CAAACAAAGACTTCGTTGACTAGGATAATGCTGGACAATATGGTTGTTCCATTATCTAACGGAGATATTGATGTATCCATGCTTA
AGGAGGCTGTAGAATTGATCAATGGGAGGTTTGATACGGAGGCTTCAGGAAATGTTACCCTTGAAACAGTACACAAGATTGGACA
```

```
AACTGGTGTTACCTACATTTCTAGTGGTGCCCTGACGCATTCCGTGAAAGCACTTGACATTTCCCTGAAGATCGATACAGAGCTC
GCCCTTGAAGATGGAAGGCGTACAAAACGAGCATGA
```

SEQ ID NO: 6
(QPTpolypeptide)
```
MFRAIPFTATVHPYAITAPRLVVKMSAIATKNTRVESLEVKPPAHPTYDLKEVMKLALSEDAGNLGDVTCKATIPLDMESDAHFL
AKEDGIIAGIALAEMIPAEVDPSLKVEWYVNDGDKVHKGLKFGKVQGNAYNIVIAERVVLNFMQRMSGIATLTKEMADAAHPAYI
LETRKTAPGLRLVDKWAVLIGGGKNHRMGLFDMVMIKDNHISAAGGVGKALKSVDQYLEQNKLQIGVEVETRTIEEVREVLDYAS
QTKTSLTRIMLDNMVVPLSNGDIDVSMLKEAVELINGRFDTEASGNVTLETVHKIGQTGVTYISSGALTHSVKALDISLKIDTEL
ALEVGRRTKRA
```

SEQ ID NO: 7
(PMT polynucleotide-full length cDNA as disclosed in NCBI No. D28506)
Hibi et al. Plant Cell (1994)
```
GGAAAATACAAACCATAATACTTTCTCTTCTTCAATTTGTTTAGTTTAATTTTGAAAATGGAAGTCATATCTACCAACACAAATG
GCTCTACCATCTTCAAGAATGGTGCCATTCCCATGAACGGCCACCAAAATGGCACTTCTGAACACCTCAACGGCTACCAGAATGG
CACTTCCAAACACCAAAACGGGCACCAGAATGGCACTTTCGAACATCGGAACGGCCACCAGAATGGGACATCCGAACAACAGAAC
GGGACAATCAGCCATGACAATGGCAACGAGCTACTGGGAAGCTCCGACTCTATTAAGCCTGGCTGGTTTTCAGAGTTTAGCGCAT
TATGGCCAGGTGAAGCATTCTCACTTAAGGTTGAGAAGTTACTATTCCAGGGGAAGTCTGATTACCAAGATGTCATGCTCTTTGA
GTCAGCAACTTATGGGAAGGTTCTGACTTTGGATGGAGCAATTCAACATACAGAGAATGGTGGATTTCCATACACTGAAATGATT
GTTCATCTACCACTTGGTTCCATCCCAAACCCAAAAAAGGTTTTGATCATCGGCGGAGGAATTGGTTTTACATTATTCGAAATGC
TTCGTTATCCTTCAATGAAAAAATTGACATTGTTGAGATCGATGACGTGGTAGTTGATGTATCCAGAAAATTTTTCCCTTATCT
GGCAGCTAATTTTAACGATCCTCGTGTAACCCTAGTTCTCGGAGATGGAGCTGCATTTGTAAAGGCTGCACAAGCGGGATATTAT
GATGCTATTATAGTGGACTCTTCTGATCCCATTGGTCCAGCAAAAGATTTGTTTGAGAGGCCATTCTTTGAGGCAGTAGCCAAAG
CCCTTAGGCCAGGAGGAGTTGTATGCACACAGGCTGAAAGCATTTGGCTTCATATGCATATTATTAAGCAAATCATTGCTAACTG
TCGTCAAGTCTTTAAGGGTTCTGTCAACTATGCTTGGACAACCGCTCCAACATATCCCACCGGTGTGATCGGTTATATGCTCTGC
TCTACTGAAGGGCCAGAAGTTGACTTCAAGAATCCAGTAAATCCAATTGACAAAGAGACAACTCAAGTCAAGTCCAAATTAGGAC
CTCTCAAGTTCTACAACTCTGATATTCACAAAGCAGCATTCATTTTACCATCTTTCGCCAGAAGTATGATCGAGTCTTAATCAAG
TGAATAATGAACACTGGTAGTACAATCATTGGACCAAGATCGAGTCTTAATCAAGTGAATAAATAAGTGAAATGCGACGTATTGT
AGGAGAATTCTGCAGTAATTATCATAATTTCCAATTCACAATCATTGTAAAATTCTTTCTCTGTGGTGTTTCGTACTTTAATATA
AATTTTCCTGCTGAAGTTTTGAATCG
```

SEQ ID NO: 7B
(PMT ORF used for vector construction)
```
ATGGAAGTCATATCTACCAACACAAATGGCTCTACCATCTTCAAGAATGGTGCCATTCCCATGAACGGCCACCAAAATGGCACTT
CTGAACACCTCAACGGCTACCAGAATGGCACTTCCAAACACCAAAACGGGCACCAGAATGGCACTTTCGAACATCGGAACGGCCA
CCAGAATGGGACATCCGAACAACAGAACGGGACAATCAGCCATGACAATGGCAACGAGCTACTGGGAAGCTCCGACTCTATTAAG
CCTGGCTGGTTTTCAGAGTTTAGCGCATTATGGCCAGGTGAAGCATTCTCACTTAAGGTTGAGAAGTTACTATTCCAGGGGAAGT
CTGATTACCAAGATGTCATGCTCTTTGAGTCAGCAACTTATGGGAAGGTTCTGACTTTGGATGGAGCAATTCAACATACAGAGAA
TGGTGGATTTCCATACACTGAAATGATTGTTCATCTACCACTTGGTTCCATCCCAAACCCAAAAAAGGTTTTGATCATCGGCGGA
GGAATTGGTTTTACATTATTCGAAATGCTTCGTTATCCTTCAATGAAAAATTGACATTGTTGAGATCGATGACGTGGTAGTTG
ATGTATCCAGAAAATTTTTCCCTTATCTGGCAGCTAATTTTAACGATCCTCGTGTAACCCTAGTTCTCGGAGATGGAGCTGCATT
TGTAAAGGCTGCACAAGCGGGATATTATGATGCTATTATAGTGGACTCTTCTGATCCCATTGGTCCAGCAAAAGATTTGTTTGAG
AGGCCATTCTTTGAGGCAGTAGCCAAAGCCCTTAGGCCAGGAGGAGTTGTATGCACACAGGCTGAAAGCATTTGGCTTCATATGC
ATATTATTAAGCAAATCATTGCTAACTGTCGTCAAGTCTTTAAGGGTTCTGTCAACTATGCTTGGACAACCGCTCCAACATATCC
CACCGGTGTGATCGGTTATATGCTCTGCTCTACTGAAGGGCCAGAAGTTGACTTCAAGAATCCAGTAAATCCAATTGACAAAGAG
ACAACTCAAGTCAAGTCCAAATTAGGACCTCTCAAGTTCTACAACTCTGATATTCACAAAGCAGCATTCATTTTACCATCTTTCG
CCAGAAGTATGATCGAGTCTTAA
```

SEQ ID NO: 8
(PMT polypeptide)
```
MEVISTNTNGSTIFKNGAIPMNGHQNGTSEHLNGYQNGTSKHQNGHQNGTFEHRNGHQNGTSEQQNGTISHDNGNELLGSSDSIK
PGWFSEFSALWPGEAFSLKVEKLLFQGKSDYQDVMLFESATYGKVLTLDGAIQHTENGGFPYTEMIVHLPLGSIPNPKKVLIIGG
GIGFTLFEMLRYPSIEKIDIVEIDDVVVDVSRKFFPYLAANFNDPRVTLVLGDGAAFVKAAQAGYYDAIIVDSSDPIGPAKDLFE
RPFFEAVAKALRPGGVVCTQAESIWLHMHIIKQIIANCRQVFKGSVNYAWTTAPTYPTGVIGYMLCSTEGPEVDFKNPVNPIDKE
TTQVKSKLGPLKFYNSDIHKAAFILPSFARSMIES
```

What is claimed is:

1. A method of producing a A662 enzyme and a NBB1 enzyme, the method comprising transforming a cell with an isolated nucleic molecule encoding A662 and NBB1 and growing the transformed cell under conditions such that the A662 enzyme and the NBB1 enzyme are produced,
   wherein the isolated nucleic acid molecule encoding A662 comprises at least one of:
   (a) the nucleotide sequence set forth in SEQ ID NO: 3; and
   (b) a nucleotide sequence that encodes a polypeptide having the amino acid sequence set forth in SEQ ID NO: 4 and
   wherein the isolated nucleic acid molecule encoding NBB1 comprises at least one of:
   (i) the nucleotide sequence set forth in SEQ ID NO: 1; and
   (ii) a nucleotide sequence that encodes a polypeptide having the amino acid sequence set forth in SEQ ID NO: 2.

2. The method according of claim 1, wherein the transformed cell is selected from the group consisting of bacteria, yeast, filamentous fungi, algae, green plants, insect, and mammalian cells.

3. The method according to claim 2, wherein the yeast cell is a *Saccharomyces cerivisae* or *Pichia pastoris* cell.

4. The method according to claim 2 wherein the filamentous fungi cell is an *Aspergillus* or *Trichoderma* cell.

5. The method according to claim 2, wherein the bacteria cell is an *Escherichia coli* cell.

6. The method according to claim 2, wherein the mammalian cell is a Chinese hamster ovary cell (CHO), a fertilized oocyte, or an embryonic stem cell.

7. The method according to claim 2, wherein the algae cell is a *Chlamydomonas reinhardtii* cell.

8. A method for increasing nicotine in a *Nicotiana* plant, the method comprising:
   (a) transforming a *Nicotiana* plant with a construct comprising, in the 5' to 3' direction, a promoter operably linked to a first heterologous nucleic acid encoding an enzyme that increases nicotine synthesis; wherein said first nucleic acid is an A622 gene and the A622 gene is overexpressed; wherein the construct further comprises in the 5' to 3' direction, a promoter operably linked to a second heterologous nucleic acid encoding an enzyme that increases nicotine synthesis; wherein the second nucleic acid is a NBB1 gene and the NBB1 gene is overexpressed;
   (b) regenerating transgenic *Nicotiana* plants from the transformed plant; and
   (c) selecting a transgenic *Nicotiana* plant having increased-nicotine content relative to a control plant.

9. A *Nicotiana* plant produced by the method of claim 8, wherein the plant overexpresses the A622 gene and the NBB1 gene and has increased nicotine relative to a control plant.

10. A product comprising the plant of claim 9, wherein the product is selected from the group consisting of a cigarette, a pharmaceutical, and a nutraceutical.

* * * * *